United States Patent
Hinuma et al.

(10) Patent No.: US 7,172,876 B2
(45) Date of Patent: Feb. 6, 2007

(54) METHOD OF SCREENING THERAPEUTIC AGENTS FOR NERVE DEGENERATION ASSOCIATED DISEASES

(75) Inventors: Shuji Hinuma, Ibaraki (JP); Ryo Fujii, Ibaraki (JP); Masataka Harada, Ibaraki (JP); Masaki Hosoya, Ibaraki (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 10/517,956

(22) PCT Filed: Jun. 12, 2003

(86) PCT No.: PCT/JP03/07500

§ 371 (c)(1),
(2), (4) Date: Dec. 13, 2004

(87) PCT Pub. No.: WO03/106683

PCT Pub. Date: Dec. 24, 2003

(65) Prior Publication Data

US 2005/0233326 A1  Oct. 20, 2005

(30) Foreign Application Priority Data

Jun. 14, 2002 (JP) ............................. 2002-173798
Jul. 15, 2002 (JP) ............................. 2002-205470

(51) Int. Cl.
*G01N 33/567* (2006.01)

(52) U.S. Cl. ...................... 435/7.21; 436/501; 530/350
(58) Field of Classification Search .................... None
See application file for complete search history.

(56) References Cited

FOREIGN PATENT DOCUMENTS

WO   WO-01/21787C A1   3/2001

OTHER PUBLICATIONS

Y. Le et al., "The Journal of Neuroscience", vol. 21, RC123, pp. 1-5, (2001).
H. Yazawa et al., "The FASEB Journal", vol. 15, pp. 2454-2462, (2001).
L. Bao et al., "Genomics", vol. 13, pp. 437-440 (1992).
A. Betten et al., "The Journal of Clinical Investigation", vol. 108, No. 8, pp. 1221-1228 (2001).
D. Yang et al., "Journal of Leukocyte Biology", vol. 72, pp. 598-607, (2002).

*Primary Examiner*—John D. Ulm
(74) *Attorney, Agent, or Firm*—David G. Conlin; Christine C. O'Day; Edwards Angell Palmer & Dodge, LLP

(57) ABSTRACT

By using a G protein-coupled receptor protein containing an amino acid sequence, which is the same or the substantially the same as an amino acid sequence represented by SEQ ID NO:1, SEQ ID NO:10, SEQ ID NO:12 or SEQ ID NO:14, or its salt together with humanin, a compound or its salt capable of changing the binding properties of the above receptor protein or its salt to humanin can be efficiently screened.

14 Claims, 3 Drawing Sheets

Fig. 3

| Sample | EC$_{50}$ Values (nM) | | |
|---|---|---|---|
| | hFPR1(No.14) | hFPRL1(No.8) | hFPRL2(No.17) |
| formyl-Humanin | 580 | 0.012 | 4.3 |
| mt-formyl-Humanin | 160 | 0.96 | 21 |
| mt-formyl-rattin | 180 | 0.030 | 160 |
| Humanin | 1600 | 3.6 | 3.0 |
| [Gly$^{14}$]Humanin | >10000 | 4.6 | 3.9 |
| W-Peptide | 0.14 | 0.027 | >10000 |
| β-Amyloid(1-42) | >10000 | 1200 | >10000 |

| Sample | EC$_{50}$ Values (nM) | |
|---|---|---|
| | mFPRL2(No.15) | rFPRL1(No.15) |
| formyl-Humanin | 0.17 | 0.19 |
| mt-formyl-Humanin | 11 | 12 |
| mt-formyl-rattin | 0.60 | 1.1 |
| Humanin | 52 | 25 |
| [Gly$^{14}$]Humanin | 67 | 43 |
| W-Peptide | 0.063 | 0.12 |
| β-Amyloid(1-42) | 170 | >10000 | ns

SEQUENCE LISTING

```
<160> NUMBER OF SEQ ID NOS: 24

<210> SEQ ID NO 1
<211> LENGTH: 351
<212> TYPE: PRT
<213> ORGANISM: Human

<400> SEQUENCE: 1

Met Glu Thr Asn Phe Ser Thr Pro Leu Asn Glu Tyr Glu Glu Val Ser
                 5                  10                  15

Tyr Glu Ser Ala Gly Tyr Thr Val Leu Arg Ile Leu Pro Leu Val Val
             20                  25                  30

Leu Gly Val Thr Phe Val Leu Gly Val Leu Gly Asn Gly Leu Val Ile
         35                  40                  45

Trp Val Ala Gly Phe Arg Met Thr Arg Thr Val Thr Thr Ile Cys Tyr
     50                  55                  60

Leu Asn Leu Ala Leu Ala Asp Phe Ser Phe Thr Ala Thr Leu Pro Phe
```

```
                65                  70                  75                  80
Leu Ile Val Ser Met Ala Met Gly Glu Lys Trp Pro Phe Gly Trp Phe
                    85                  90                  95

Leu Cys Lys Leu Ile His Ile Val Val Asp Ile Asn Leu Phe Gly Ser
                100                 105                 110

Val Phe Leu Ile Gly Phe Ile Ala Leu Asp Arg Cys Ile Cys Val Leu
                115                 120                 125

His Pro Val Trp Ala Gln Asn His Arg Thr Val Ser Leu Ala Met Lys
                130                 135                 140

Val Ile Val Gly Pro Trp Ile Leu Ala Leu Val Leu Thr Leu Pro Val
145                 150                 155                 160

Phe Leu Phe Leu Thr Thr Val Thr Ile Pro Asn Gly Asp Thr Tyr Cys
                165                 170                 175

Thr Phe Asn Phe Ala Ser Trp Gly Gly Thr Pro Glu Glu Arg Leu Lys
                180                 185                 190

Val Ala Ile Thr Met Leu Thr Ala Arg Gly Ile Ile Arg Phe Val Ile
                195                 200                 205

Gly Phe Ser Leu Pro Met Ser Ile Val Ala Ile Cys Tyr Gly Leu Ile
                210                 215                 220

Ala Ala Lys Ile His Lys Lys Gly Met Ile Lys Ser Ser Arg Pro Leu
225                 230                 235                 240

Arg Val Leu Thr Ala Val Val Ala Ser Phe Phe Ile Cys Trp Phe Pro
                245                 250                 255

Phe Gln Leu Val Ala Leu Leu Gly Thr Val Trp Leu Lys Glu Met Leu
                260                 265                 270

Phe Tyr Gly Lys Tyr Lys Ile Ile Asp Ile Leu Val Asn Pro Thr Ser
                275                 280                 285

Ser Leu Ala Phe Phe Asn Ser Cys Leu Asn Pro Met Leu Tyr Val Phe
                290                 295                 300

Val Gly Gln Asp Phe Arg Glu Arg Leu Ile His Ser Leu Pro Thr Ser
305                 310                 315                 320

Leu Glu Arg Ala Leu Ser Glu Asp Ser Ala Pro Thr Asn Asp Thr Ala
                325                 330                 335

Ala Asn Ser Ala Ser Pro Pro Ala Glu Thr Glu Leu Gln Ala Met
                340                 345                 350

<210> SEQ ID NO 2
<211> LENGTH: 1053
<212> TYPE: DNA
<213> ORGANISM: Human

<400> SEQUENCE: 2
atggaaacca acttctccac tcctctgaat gaatatgaag aagtgtccta tgagtctgct    60
ggctacactg ttctgcggat cctcccattg gtggtgcttg gggtcacctt tgtcctcggg   120
gtcctgggca atgggcttgt gatctgggtg gctggattcc ggatgacacg cacagtcacc   180
accatctgtt acctgaacct ggccctggct gactttcctt tcacggccac attaccattc   240
ctcattgtct ccatggccat gggagaaaaa tggccttttg ctggttcct gtgtaagtta   300 attcacatcg tggtggacat caacctcttt ggaagtgtct tcttgattgg tttcattgca   360
ctggaccgct gcatttgtgt cctgcatcca gtctgggccc agaaccaccg cactgtgagt   420
ctggccatga aggtgatcgt cggaccttgg attcttgctc tagtccttac cttgccagtt   480
ttcctctttt tgactacagt aactattcca aatggggaca catactgtac tttcaacttt   540
```

```
gcatcctggg gtggcacccc tgaggagagg ctgaaggtgg ccattaccat gctgacagcc      600
agagggatta tccggtttgt cattggcttt agcttgccga tgtccattgt tgccatctgc      660
tatgggctca ttgcagccaa gatccacaaa aagggcatga ttaaatccag ccgtcccta      720 cgggtcctca ctgctgtggt ggcttctttc ttcatctgtt ggtttcctt tcaactggtt       780 gcccttctgg gcaccgtctg gctcaaagag atgttgttct atggcaagta caaaatcatt      840
gacatcctgg ttaacccaac gagctccctg gccttcttca cagctgcct caaccccatg       900 ctttacgtct tgtgggcca agacttccga gagagactga tccactccct gcccaccagt       960
ctggagaggg ccctgtctga ggactcagcc ccaactaatg cacggctgc caattctgct       1020 tcacctcctg cagagactga gttacaggca atg                                   1053
```

<210> SEQ ID NO 3
<211> LENGTH: 24
<212> TYPE: PRT
<213> ORGANISM: Human

<400> SEQUENCE: 3

Met Ala Pro Arg Gly Phe Ser Cys Leu Leu Leu Leu Thr Ser Glu Ile
 1               5                  10                  15

Asp Leu Pro Val Lys Arg Arg Ala
            20          24

<210> SEQ ID NO 4
<211> LENGTH: 24
<212> TYPE: PRT
<213> ORGANISM: Human

<400> SEQUENCE: 4

Met Ala Pro Arg Gly Phe Ser Cys Leu Leu Leu Leu Thr Gly Glu Ile
 1               5                  10                  15

Asp Leu Pro Val Lys Arg Arg Ala
            20          24

<210> SEQ ID NO 5
<211> LENGTH: 24
<212> TYPE: PRT
<213> ORGANISM: Human

<400> SEQUENCE: 5

Met Ala Arg Arg Gly Phe Ser Cys Leu Leu Leu Ser Thr Thr Ala Thr
 1               5                  10                  15

Asp Leu Pro Val Lys Arg Arg Thr
            20

<210> SEQ ID NO 6
<211> LENGTH: 21
<212> TYPE: PRT
<213> ORGANISM: Human

<400> SEQUENCE: 6

Met Ala Pro Arg Gly Phe Ser Cys Leu Leu Leu Leu Thr Ser Glu Ile
 1               5                  10                  15

Asp Leu Pro Val Lys
            20  21

<210> SEQ ID NO 7
<211> LENGTH: 38
<212> TYPE: PRT
<213> ORGANISM: Rat

<400> SEQUENCE: 7

Met Ala Lys Arg Gly Phe Asn Cys Leu Leu Leu Ser Ile Ser Glu Ile
                5                   10                  15
Asp Leu Pro Val Lys Arg Leu Glu Ser Pro Asn Lys Thr Arg Arg Pro
            20                  25                  30
Tyr Gly Ala Ser Ile Tyr
        35          38

<210> SEQ ID NO 8
<211> LENGTH: 24
<212> TYPE: PRT
<213> ORGANISM: Rat

<400> SEQUENCE: 8

Met Ala Lys Arg Gly Phe Asn Cys Leu Leu Leu Ser Ile Ser Glu Ile
                5                   10                  15
Asp Leu Pro Val Lys Arg Leu Glu
            20          24

<210> SEQ ID NO 9
<211> LENGTH: 21
<212> TYPE: PRT
<213> ORGANISM: Rat

<400> SEQUENCE: 9

Met Ala Lys Arg Gly Phe Asn Cys Leu Leu Leu Ser Ile Ser Glu Ile
                5                   10                  15
Asp Leu Pro Val Lys
            20  21

<210> SEQ ID NO 10
<211> LENGTH: 351
<212> TYPE: PRT
<213> ORGANISM: Rat

<400> SEQUENCE: 10

Met Glu Ala Asn Tyr Ser Ile Pro Leu Asn Val Ser Glu Val Val Val
                5                   10                  15
Tyr Asp Ser Thr Ile Ser Arg Val Leu Trp Ile Leu Thr Met Val Val
            20                  25                  30
Leu Ser Ile Thr Phe Val Leu Gly Val Leu Gly Asn Gly Leu Val Ile
        35                  40                  45
Trp Val Ala Gly Phe Arg Met Val His Thr Val Thr Thr Thr Cys Phe
50                  55                  60
Leu Asn Leu Ala Leu Ala Asp Phe Ser Phe Thr Val Thr Leu Pro Phe
65                  70                  75                  80
Phe Val Ile Ser Ile Ala Met Lys Glu Lys Trp Pro Phe Gly Trp Phe
                85                  90                  95
Leu Cys Lys Leu Val His Ile Val Val Asp Ile Asn Leu Phe Gly Ser
            100                 105                 110
Val Phe Leu Ile Ala Leu Ile Ala Leu Asp Arg Cys Ile Cys Val Leu
        115                 120                 125
His Pro Val Trp Ala Gln Asn His Arg Thr Val Ser Leu Ala Arg Lys
    130                 135                 140
Val Val Val Gly Pro Trp Ile Leu Ala Leu Ile Leu Thr Leu Pro Ile
145                 150                 155                 160
Phe Ile Phe Met Thr Thr Val Arg Ile Pro Gly Gly Asn Val Tyr Cys

```
                    165                 170                 175
Thr Phe Asn Phe Ala Ser Trp Gly Asn Thr Ala Glu Glu Leu Leu Asn
                180                 185                 190
Ile Ala Asn Thr Phe Val Thr Val Arg Gly Ser Ile Arg Phe Ile Ile
            195                 200                 205
Gly Phe Ile Met Pro Met Ser Ile Val Ala Ile Cys Tyr Gly Leu Ile
        210                 215                 220
Ala Val Lys Ile His Arg Arg Ala Leu Val Asn Ser Ser Arg Pro Leu
225                 230                 235                 240
Arg Val Leu Thr Ala Val Val Ala Ser Phe Phe Ile Cys Trp Phe Pro
                245                 250                 255
Phe Gln Leu Val Ala Leu Leu Gly Thr Ile Trp Phe Lys Glu Ser Leu
                260                 265                 270
Phe Ser Gly Arg Tyr Lys Ile Leu Asp Met Trp Val His Pro Thr Ser
            275                 280                 285
Ser Leu Ala Tyr Phe Asn Ser Cys Leu Asn Pro Met Leu Tyr Ala Phe
        290                 295                 300
Met Gly Gln Asp Phe His Glu Arg Leu Ile His Ser Leu Pro Ser Ser
305                 310                 315                 320
Leu Glu Arg Ala Leu Ser Glu Asp Ser Gly Gln Thr Ser Asp Thr Gly
                325                 330                 335
Ile Ser Ser Ala Leu Pro Pro Val Asn Ile Asp Ile Lys Ala Ile
                340                 345                 350
```

<210> SEQ ID NO 11
<211> LENGTH: 1053
<212> TYPE: DNA
<213> ORGANISM: Rat

<400> SEQUENCE: 11

```
atggaagcca actattccat ccctctgaat gtatcagaag tggttgtcta tgattctacc      60
atctccagag ttttgtggat cctcacaatg gtggttctct ccatcacctt tgtcctgggt     120
gtgctgggta atggactagt gatctgggta gctggattcc ggatggtaca cactgtcacc     180
actacctgtt ttctgaatct agctttggct gacttctctt tcacagtgac tctaccattc     240
tttgtcatct caattgctat gaaagaaaaa tggccttttg gatggttcct gtgtaaatta     300
gttcacattg tagtagacat aaacctcttt ggaagtgtct tcctgattgc tttaattgcc     360
ttggaccgct gcatttgtgt cctgcatcca gtctgggctc agaaccaccg cactgtgagc     420
ctggctagga aggtggttgt tgggccctgg attttagctc tgattctcac tttgcccatt     480
tttattttca tgactacagt tagaattcct ggaggcaatg tgtactgtac attcaacttc     540
gcatcctggg gtaacactgc tgaagaacta ttgaacatag ctaacacttt tgtaacagtt     600
agagggagca tcaggttcat tattggcttc ataatgccta tgtccattgt tgccatctgc     660
tatggactca tcgctgtcaa gatccacaga agagcacttg ttaattccag ccgtccatta     720
agagtcctta cagcagttgt ggcttccttc tttatctgtt ggtttccctt tcaactggtg     780
gcccttttag gtacaatctg gtttaaagag tcattgttta gtggtcgtta caaaattctt     840
gacatgtggg ttcacccaac cagctcattg gcctacttca atagttgcct caatccaatg     900
ctctatgctt tcatgggcca ggactttcat gaaagactga ttcattccct gccttccagt     960
ctggagagag ccctgagtga ggactctggc caaaccagtg atacaggcat cagttctgct    1020
ttacctcctg taaacattga tataaaagca ata                                 1053
```

```
<210> SEQ ID NO 12
<211> LENGTH: 351
<212> TYPE: PRT
<213> ORGANISM: Mouse

<400> SEQUENCE: 12

Met Glu Ser Asn Tyr Ser Ile His Leu Asn Gly Ser Glu Val Val
                  5                  10                  15

Tyr Asp Ser Thr Ile Ser Arg Val Leu Trp Ile Leu Ser Met Val Val
                 20                  25                  30

Val Ser Ile Thr Phe Phe Leu Gly Val Leu Gly Asn Gly Leu Val Ile
                 35                  40                  45

Trp Val Ala Gly Phe Arg Met Pro His Thr Val Thr Thr Ile Trp Tyr
 50                  55                  60

Leu Asn Leu Ala Leu Ala Asp Phe Ser Phe Thr Ala Thr Leu Pro Phe
 65                  70                  75                  80

Leu Leu Val Glu Met Ala Met Lys Glu Lys Trp Pro Phe Gly Trp Phe
                 85                  90                  95

Leu Cys Lys Leu Val His Ile Val Val Asp Val Asn Leu Phe Gly Ser
                100                 105                 110

Val Phe Leu Ile Ala Leu Ile Ala Leu Asp Arg Cys Ile Cys Val Leu
                115                 120                 125

His Pro Val Trp Ala Gln Asn His Arg Thr Val Ser Leu Ala Arg Lys
                130                 135                 140

Val Val Val Gly Pro Trp Ile Phe Ala Leu Ile Leu Thr Leu Pro Ile
145                 150                 155                 160

Phe Ile Phe Leu Thr Thr Val Arg Ile Pro Gly Gly Asp Val Tyr Cys
                165                 170                 175

Thr Phe Asn Phe Gly Ser Trp Ala Gln Thr Asp Glu Glu Lys Leu Asn
                180                 185                 190

Thr Ala Ile Thr Phe Val Thr Thr Arg Gly Ile Ile Arg Phe Leu Ile
                195                 200                 205

Gly Phe Ser Met Pro Met Ser Ile Val Ala Val Cys Tyr Gly Leu Ile
210                 215                 220

Ala Val Lys Ile Asn Arg Arg Asn Leu Val Asn Ser Ser Arg Pro Leu
225                 230                 235                 240

Arg Val Leu Thr Ala Val Ala Ser Phe Ile Cys Trp Phe Pro
                245                 250                 255

Phe Gln Leu Val Ala Leu Leu Gly Thr Val Trp Phe Lys Glu Thr Leu
                260                 265                 270

Leu Ser Gly Ser Tyr Lys Ile Leu Asp Met Phe Val Asn Pro Thr Ser
                275                 280                 285

Ser Leu Ala Tyr Phe Asn Ser Cys Leu Asn Pro Met Leu Tyr Val Phe
                290                 295                 300

Met Gly Gln Asp Phe Arg Glu Arg Phe Ile His Ser Leu Pro Tyr Ser
305                 310                 315                 320

Leu Glu Arg Ala Leu Ser Glu Asp Ser Gly Gln Thr Ser Asp Ser Ser
                325                 330                 335

Thr Ser Ser Thr Ser Pro Pro Ala Asp Ile Glu Leu Lys Ala Pro
                340                 345                 350

<210> SEQ ID NO 13
<211> LENGTH: 1053
<212> TYPE: DNA
<213> ORGANISM: Mouse
```

<400> SEQUENCE: 13

```
atggaatcca actactccat ccatctgaat ggatcagaag tggtggttta tgattctacc      60
atctccagag ttctgtggat cctctcaatg gtggttgtct ccatcacttt cttccttggt     120
gtgctgggca atggactagt gatttgggta gctggattcc ggatgccaca cactgtcacc     180
actatctggt atctgaatct agcattggct gacttttctt tcacagcaac tctaccattc     240
cttcttgttg aaatggctat gaaagaaaaa tggccttttg gctggttcct gtgtaaatta     300
gttcacattg tggtagatgt aaacctgttt ggaagtgtct tcttgattgc tctcattgcc     360
ttggaccgct gcatttgtgt tctgcatcca gtctgggctc agaaccaccg cactgtgagc     420
ctggctagga aggtggttgt tgggccctgg attttgctc tgattctcac tttgcccatt      480
tttatttct tgactactgt tagaattcct ggaggagatg tgtattgtac attcaacttt     540
ggatcctggg ctcaaactga tgaagaaaag ttgaacacag ctatcacttt tgtaacaact     600
agagggatca tcaggttcct tattggtttc agcatgccca tgtcaattgt tgctgtttgc     660
tatggactca ttgctgtcaa gatcaacaga gaaaacttg ttaattccag ccgtcccttta     720
cgagtcctta cagcagttgt ggcttccttc tttatctgct ggtttcccttt tcagcttgtg    780
gccctttggg gcacagtctg gtttaaagag acattgctta gtggtagtta taaaattctt    840
gacatgtttg ttaacccaac aagctcattg gcttacttca atagttgtct caatccgatg    900
ctctatgttt tcatgggcca ggactttcgt gagagattta ttcattccct gccttatagt    960
cttgagagag ccctgagtga ggattctggt caaaccagtg attcaagcac cagttctact   1020
tcacctcctg cagacattga gttaaaggcc cca                                 1053
```

<210> SEQ ID NO 14
<211> LENGTH: 353
<212> TYPE: PRT
<213> ORGANISM: Human

<400> SEQUENCE: 14

```
Met Glu Thr Asn Phe Ser Ile Pro Leu Asn Glu Thr Glu Glu Val Leu
              5                  10                  15

Pro Glu Pro Ala Gly His Thr Val Leu Trp Ile Phe Ser Leu Leu Val
         20                  25                  30

His Gly Val Thr Phe Val Phe Gly Val Leu Gly Asn Gly Leu Val Ile
     35                  40                  45

Trp Val Ala Gly Phe Arg Met Thr Arg Thr Val Asn Thr Ile Cys Tyr
 50                  55                  60

Leu Asn Leu Ala Leu Ala Asp Phe Ser Phe Ser Ala Ile Leu Pro Phe
65                  70                  75                  80

Arg Met Val Ser Val Ala Met Arg Glu Lys Trp Pro Phe Ala Ser Phe
                 85                  90                  95

Leu Cys Lys Leu Val His Val Met Ile Asp Ile Asn Leu Phe Val Ser
            100                 105                 110

Val Tyr Leu Ile Thr Ile Ala Leu Asp Arg Cys Ile Cys Val Leu
        115                 120                 125

His Pro Ala Trp Ala Gln Asn His Arg Thr Val Ser Leu Ala Lys Arg
    130                 135                 140

Val Met Thr Gly Leu Trp Ile Phe Thr Ile Val Leu Thr Leu Pro Asn
145                 150                 155                 160

Phe Ile Phe Trp Thr Thr Ile Ser Thr Thr Asn Gly Asp Thr Tyr Cys
                165                 170                 175
```

Ile Phe Asn Phe Ala Phe Trp Gly Asp Thr Ala Val Glu Arg Leu Asn
                180                 185                 190

Val Phe Ile Thr Met Ala Lys Val Phe Leu Ile Leu His Phe Ile Ile
            195                 200                 205

Gly Phe Thr Val Pro Met Ser Ile Ile Thr Val Cys Tyr Gly Ile Ile
        210                 215                 220

Ala Ala Lys Ile His Arg Asn His Met Ile Lys Ser Ser Arg Pro Leu
225                 230                 235                 240

Arg Val Phe Ala Ala Val Val Ala Ser Phe Phe Ile Cys Trp Phe Pro
                245                 250                 255

Tyr Glu Leu Ile Gly Ile Leu Met Ala Val Trp Leu Lys Glu Met Leu
            260                 265                 270

Leu Asn Gly Lys Tyr Lys Ile Ile Leu Val Leu Ile Asn Pro Thr Ser
        275                 280                 285

Ser Leu Ala Phe Phe Asn Ser Cys Leu Asn Pro Ile Leu Tyr Val Phe
        290                 295                 300

Met Gly Arg Asn Phe Gln Glu Arg Leu Ile Arg Ser Leu Pro Thr Ser
305                 310                 315                 320

Leu Glu Arg Ala Leu Thr Glu Val Pro Asp Ser Ala Gln Thr Ser Asn
                325                 330                 335

Thr His Thr Ser Ala Ser Pro Pro Glu Glu Thr Glu Leu Gln Ala
            340                 345                 350

Met

<210> SEQ ID NO 15
<211> LENGTH: 1059
<212> TYPE: DNA
<213> ORGANISM: Human

<400> SEQUENCE: 15
atggaaacca acttctccat tcctctgaat gaaactgagg aggtgctccc tgagcctgct        60
ggccacaccg ttctgtggat cttctcattg ctagtccacg gagtcacctt tgtcttcggg       120
gtcctgggca atgggcttgt gatctgggtg gctggattcc ggatgacacg cacagtcaac       180
accatctgtt acctgaacct ggccctagct gacttctctt tcagtgccat cctaccattc       240
cgaatggtct cagtcgccat gagagaaaaa tggccttttg cgtcattcct atgtaagtta       300
gttcatgtta tgatagacat caacctgttt gtcagtgtct acctgatcac catcattgct       360
ctggaccgct gtatttgtgt cctgcatcca gcctgggccc agaaccatcg caccatgagt       420
ctggccaaga gggtgatgac gggactctgg attttcacca tagtccttac cttaccaaat       480
ttcatcttct ggactacaat aagtactacg aatgggaca catactgtat ttcaactttt       540
gcattctggg gtgacactgc tgtagagagg ttgaacgtgt tcattaccat ggccaaggtc       600
tttctgatcc tccacttcat tattggcttc acggtgccta tgtccatcat cacagtctgc       660
tatgggatca tcgctgccaa aattcacaga aaccacatga ttaaatccag ccgtccctta       720
cgtgtcttcg ctgctgtggt ggcttctttc ttcatctgtt ggttccctta tgaactaatt       780
ggcattctaa tggcagtctg gctcaaagag atgttgttaa atggcaaata caaatcatt        840 cttgtcctga ttaacccaac aagctccttg gccttttta acagctgcct caacccaatt       900
ctctacgtct ttatgggtcg taacttccaa gaaagactga ttcgctcttt gcccactagt       960
ttggagaggg ccctgactga ggtccctgac tcagcccaga ccagcaacac acacaccact      1020
tctgcttcac ctcctgagga gacggagtta caagcaatg                             1059

<210> SEQ ID NO 16
<211> LENGTH: 42
<212> TYPE: DNA
<213> ORGANISM: Artificial Sequence
<220> FEATURE:
<223> OTHER INFORMATION: Primer

<400> SEQUENCE: 16
aaacagtcga ccaccatgga atccaactac tccatccatc tg                    42

<210> SEQ ID NO 17
<211> LENGTH: 33
<212> TYPE: DNA
<213> ORGANISM: Artificial Sequence
<220> FEATURE:
<223> OTHER INFORMATION: Primer

<400> SEQUENCE: 17
ctttctagat catggggcct ttaactcaat gtc                              33

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
atctgggtag ctggattccg gatg                                        24

<210> SEQ ID NO 19
<211> LENGTH: 27
<212> TYPE: DNA
<213> ORGANISM: Artificial Sequence
<220> FEATURE:
<223> OTHER INFORMATION: Primer

<400> SEQUENCE: 19
tctttcatga aagtcctggc ccatgaa                                     27

<210> SEQ ID NO 20
<211> LENGTH: 24
<212> TYPE: DNA
<213> ORGANISM: Artificial Sequence
<220> FEATURE:
<223> OTHER INFORMATION: Primer

<400> SEQUENCE: 20
aggaattcta actgtagtca tgaa                                        24

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
acagttagag ggagcatcag gttc                                        24

<210> SEQ ID NO 22
<211> LENGTH: 43
<212> TYPE: DNA
<213> ORGANISM: Artificial Sequence
<220> FEATURE:

-continued

```
<223> OTHER INFORMATION: Primer

<400> SEQUENCE: 22
ataaagtcga ccaccatgga agccaactat tccatccctc tga          43

<210> SEQ ID NO 23
<211> LENGTH: 37
<212> TYPE: DNA
<213> ORGANISM: Artificial Sequence
<220> FEATURE:
<223> OTHER INFORMATION: Primer

<400> SEQUENCE: 23
aaatctagat catattgctt ttatatcaat gtttaca                 37

<210> SEQ ID NO 24
<211> LENGTH: 6
<212> TYPE: PRT
<213> ORGANISM: Artificial Sequence
<220> FEATURE:
<223> OTHER INFORMATION: Primer

<400> SEQUENCE: 24

Trp Lys Tyr Met Val Met
 1               5
```

METHOD OF SCREENING THERAPEUTIC AGENTS FOR NERVE DEGENERATION ASSOCIATED DISEASES

TECHNICAL FIELD

The present invention relates to novel applications of a G protein-coupled receptor protein (FPRL1 or FPRL2).

BACKGROUND ART

Physiological active substances such as various hormones and neurotransmitters regulate the biological function via specific receptor proteins present on cell membranes. Many of these receptor proteins are coupled with guanine nucleotide-binding protein (hereinafter sometimes simply referred to as G protein) and mediate the intracellular signal transduction via activation of G protein. These receptor proteins possess the common structure containing seven transmembrane domains and are thus collectively referred to as G protein-coupled receptors or seven-transmembrane receptors (7TMR).

G protein-coupled receptor proteins present on the cell surface of each functional cell and organ in the body, and play important physiological roles as the target of the molecules that regulate the functions of the cells and organs, e.g., hormones, neurotransmitters, physiologically active substances and the like. Receptors transmit signals to cells via binding with physiologically active substances, and the signals induce various reactions such as activation and inhibition of the cells.

To clarify the relationship between substances that regulate complex biological functions in various cells and organs, and their specific receptor proteins, in particular, G protein-coupled receptor proteins, would elucidate the functional mechanisms in various cells and organs in the body to provide a very important means for development of drugs closely associated with the functions.

For example, in various organs, their physiological functions are controlled in vivo through regulation by many hormones, hormone-like substances, neurotransmitters or physiologically active substances. In particular, physiologically active substances are found in numerous sites of the body and regulate the physiological functions through their corresponding receptor proteins. However, it is supposed that many unknown hormones, neurotransmitters or many other physiologically active substances still exist in the body and, as to their receptor proteins, many of these proteins have not yet been reported. In addition, it is still unknown if there are subtypes of known receptor proteins.

It is very important for development of drugs to clarify the relationship between substances that regulate elaborated functions in vivo and their specific receptor proteins. Furthermore, for efficient screening of agonists and antagonists to receptor proteins in development of drugs, it is required to clarify functional mechanisms of receptor protein genes expressed in vivo and express the genes in an appropriate expression system.

In recent years, random analysis of cDNA sequences has been actively studied as a means for analyzing genes expressed in vivo. The sequences of cDNA fragments thus obtained have been registered on and published to databases as Expressed Sequence Tag (EST). However, since many ESTs contain sequence information only, it is difficult to predict their functions from the information.

As one of orphan G protein-coupled receptor proteins, human FPRL1 is known (J. Biol. Chem. 267(11), 7637–7643 (1992)). Agonists of FPRL1 which have been reported include bacterium-derived fMLF, a partial peptide of HIV-derived gp41 or gp120, a partial peptide of prion, intrinsic substances such as Aβ42, a partial peptide of Annexin I and partial peptides of acute phase protein, hCAP18 and NADH dehydrogenase, and lipoxin A4 as lipid (Immunopharmacol. 2, 1–13, 2002).

Alzheimer's disease is a typical nerve degeneration disease involving progressive dementia and loss in recognition ability, and no effective therapy for this disease has been found. As a matter of course, Alzheimer's disease is the most important disease at present in the advent of an aging society, and development of therapeutic agents therefor has a significantly great meaning medically and economically.

Recently, Hashimoto et al. paid attention to the fact that there are fewer lesions in the occipital lobe of a patient with Alzheimer's disease, and by the "death trap" method (L. D' Adamio et al., Semin. Immunol., 9, 17–23, 1997), a gene inhibiting the apotosis of nerve cells into which a causative gene of familial Alzheimer's disease had been introduced was cloned from the occipital lobe (Proc. Natl. Acad. Sci. USA, 98, 6336–6341, 2001). This gene, named humanin (WO 01/21787), encodes a peptide consisting of 24 residues, and a synthetic humanin peptide inhibited not only death of nerve cells into which the familial Alzheimer's disease gene had been introduced, but also nerve apotosis induced by adding β-amyloid also supposed to cause Alzheimer's disease. Humanin is secreted outside of cells and considered to act on nerve cells to inhibit apotosis, but its receptor has not been revealed.

It is reported that Aβ42 is an agonist of FPRL1 and shows chemotaxis via FPRL1, and also that FPRL1 is accumulated in senile spots as a lesion characteristic of Alzheimer's disease. From these findings, the relationship between FPRL1 and inflammatory reaction observed in Alzheimer's disease is suggested (The Journal of Neuroscience, 2001, Vo. 21 RC123).

It is also reported that Aβ42 is incorporated via FPRL1 into macrophage cells thereby forming fibrin agglutination (amyloid-like deposition) (The FASEB Journal, Vol. 15, 2454–2462, November 2001).

Mouse FPRL2 is also known as one of orphan G protein-coupled receptor proteins (Genomics 13(2), 437–440 (1992)).

It is reported that although human FPRL2 is highly homologous to FPR1 that is a receptor of FMLF (formyl-Met-Leu-Phe), human FPRL2 does not react with fMLF. It is also reported that FPRL2 was recognized to be expressed in monocytes, but not recognized to be expressed in neutrophils in which expression of FPR1 and FPRL1 was recognized (Biochem. Biophys. Res. Commun., 201(1), 174–9, May 30, 1994).

It is reported that W-Peptide (Trp-Lys-Tyr-Met-Val-Met-NH$_2$) is an agonist of FPRL1 and FPRL2, and that FPRL2 is highly expressed in monocytes (J. Biol. Chem. 276(24), 21585–21593 (2001)).

It is reported that *Helicobacter pylori*-derived peptide Hp (2-20) is an agonist of FPRL2 and activates monocytes via FPRL1/FPRL2 (J. Clin. Invest., 108(8), 1221–8, October 2001).

It is reported that FPRL2 whose functions are maintained is expressed in one kind of antigen presenting cells, that is, dendritic cells (mature type, immature type) and considered to regulate trafficking of the dendritic cells (J. Leukoc. Biol., 72(3), 598–607, September 2002).

It is described that rat humanin has a protective activity on nerves (The FASEB Journal, Vol. 16, 1331–1333, August 2002).

Substances that inhibit binding between G protein-coupled proteins and physiologically active substances (i.e., ligands) and substances that bind and induce signals similar to those induced by physiologically active substances (i.e., ligands) have been used as pharmaceuticals, as antagonists and agonists specific to the receptors, that regulate the biological functions. Therefore, discovery and gene cloning (e.g., cDNA) of a novel G protein-coupled receptor that can be targeted for pharmaceutical development are very important means in search for a specific ligand, agonist, and antagonist of the novel G protein-coupled receptor.

However, not all G protein-coupled receptors have been discovered. There are unknown G protein-coupled receptors and many of these receptors in which the corresponding ligands are yet unidentified are called orphan receptors. Therefore, search and functional elucidation of a novel G protein-coupled receptor is awaited.

G protein-coupled receptors are useful in searching for a novel physiological active substance (i.e., ligand) using the signal transduction activity as the index and in search for agonists and antagonists of the receptor. Even if no physiological ligand is found, agonists and antagonist of the receptor may be prepared by analyzing the physiological action of the receptor through inactivation experiment of the receptor (knockout animal). Ligands, agonists, antagonists, etc. of the receptor are expected to be used as prophylactic/therapeutic and diagnostic agents for diseases associated with dysfunction of the G protein-coupled receptor.

Lowering or accentuation in functions of the G protein coupled receptor due to genetic aberration of the receptor in vivo causes some disorders in many cases. In this case, the G protein coupled receptor may be used not only for administration of antagonists or agonists of the receptor, but also for gene therapy by transfer of the receptor gene into the body (or some specific organs) or by introduction of the antisense nucleic acid of the receptor gene into the body (or the specific organ). In the gene therapy, information on the base sequence of the receptor gene is essentially required for investigating deletion or mutation in the gene. The receptor gene is also applicable as prophylactic/therapeutic and diagnostic agents for diseases associated with dysfunction of the receptor.

The present invention relates to determination of a ligand to an orphan G protein-coupled receptor protein FPRL1 or FPRL2 and use of FPRL1 or FPRL2 and its ligand humanin. That is, the object of the present invention is to provide a method of screening a compound (antagonist, agonist) or its salt that alters the binding property between humanin and FPRL1 or FPRL2, a kit for this screening, a compound (antagonist, agonist) or its salt that alters the binding property between humanin and FPRL1 or FPRL2, which is obtainable using the screening method or the screening kit, a pharmaceutical preparation comprising a compound (antagonist, agonist) or its salt that alters the binding property between humanin and FPRL1 or FPRL2 or a compound or its salt that alters the amount of FPRL1 or FPRL2 expressed, etc.

DISCLOSURE OF INVENTION

As a result of extensive investigation for solving the problem, the present inventors found that a ligand of FPRL1 and FPRL2 is humanin or its salt. As a result of further investigation on the basis of this finding, the present inventors arrived at the present invention.

That is, the present invention provides:

[1] a method of screening a compound or its salt that alters the binding property or signal transduction between (1) a G protein-coupled receptor protein comprising the same or substantially the same amino acid sequence as the amino acid sequence represented by SEQ ID NO: 1 (human FPRL1), SEQ ID NO: 10 (rat FPRL1), SEQ ID NO: 12 (mouse FPRL2) or SEQ ID NO: 14 (human FPRL2) or a salt thereof and (2) humanin or a salt thereof, which comprises using the receptor protein, a partial peptide thereof or a salt thereof and humanin or a salt thereof,

[2] the screening method according to the above-mentioned [1], wherein humanin is:

(1) a polypeptide comprising the same or substantially the same amino acid sequence as the amino acid sequence represented by SEQ ID NO: 3 or a salt thereof, (2) a peptide consisting of consecutive 6 to 20 amino acids in the same or substantially the same amino acid sequence as the amino acid sequence represented by SEQ ID NO: 3 or a salt thereof, or (3) a polypeptide comprising the same or substantially the same amino acid sequence as the amino acid sequence represented by SEQ ID NO: 7 or a salt thereof,

[3] the screening method according to the above-mentioned [1], wherein humanin is:

(1) a polypeptide or its salt consisting of a) the amino acid sequence represented by SEQ ID NO: 3, b) an amino acid sequence represented by SEQ ID NO: 3 wherein 1 to 10 amino acids are deleted, c) an amino acid sequence represented by SEQ ID NO: 3 to which 1 to 10 amino acids are added, d) an amino acid sequence represented by SEQ ID NO: 3 wherein 1 to 5 amino acids are substituted by other amino acids, or e) an amino acid sequence consisting of the above amino acid sequence with a combination of deletion, addition and substitution mentioned above, (2) a polypeptide or its salt consisting of a) the amino acid sequence represented by SEQ ID NO: 4, b) an amino acid sequence represented by SEQ ID NO: 4 wherein 1 to 10 amino acids are deleted, c) an amino acid sequence represented by SEQ ID NO: 4 to which 1 to 10 amino acids are added, d) an amino acid sequence represented by SEQ ID NO: 4 wherein 1 to 5 amino acids are substituted by other amino acids, or e) an amino acid sequence consisting of the above amino acid sequence with a combination of deletion, addition and substitution mentioned above, (3) a polypeptide or its salt consisting of a) the amino acid sequence represented by SEQ ID NO: 8, b) an amino acid sequence represented by SEQ ID NO: 8 wherein 1 to 10 amino acids are deleted, c) an amino acid sequence represented by SEQ ID NO: 8 to which 1 to 10 amino acids are added, d) an amino acid sequence represented by SEQ ID NO: 8 wherein 1 to 5 amino acids are substituted by other amino acids, or e) an amino acid sequence consisting of the above amino acid sequence with a combination of deletion, addition and substitution mentioned above, (4) a peptide wherein the number of amino acids is 6 to 20, or its salt, consisting of a) an amino acid sequence in positions 19 to 24, positions 5 to 24, positions 1 to 20, positions 5 to 20 or positions 5 to 21 in the amino acid sequence represented by SEQ ID NO: 3, SEQ ID NO: 4 or SEQ ID NO: 8, b) an amino acid sequence comprising the above amino acid sequence wherein 1 to 6 amino acids are deleted, c) an amino acid sequence comprising the above amino acid sequence wherein 1 to 6 amino acids are added, d) an amino acid sequence comprising the above amino acid sequence wherein 1 to 6 amino acids are substituted by other amino acids, and e) an amino acid sequence comprising the above amino acid sequence with a combination of deletion, addition and substitution mentioned above, provided that the peptide does not include a peptide consisting of an amino acid sequence in positions 19 to 24, positions 5 to 24, positions 1 to 20, positions 5 to 20 or positions 5 to 21 in the amino acid sequence represented by SEQ ID NO: 5, or (5) a polypeptide or its salt consisting of a) the amino acid sequence represented by SEQ ID NO: 7, b) an amino acid sequence represented by SEQ ID NO: 7 wherein 1 to 10 amino acids are deleted, c) an amino acid sequence represented by SEQ ID NO: 7 to which 1 to 10 amino acids are added, d) an amino acid sequence represented by SEQ ID NO: 7 wherein 1 to 10 amino acids are substituted by other amino acids, or e) an amino acid sequence consisting of the above amino acid sequence with a combination of deletion, addition and substitution mentioned above,

[4] the screening method according to the above-mentioned [1], wherein humanin is:

(1) a polypeptide consisting of the amino acid sequence represented by SEQ ID NO: 3 or a salt thereof, (2) a polypeptide consisting of the amino acid sequence represented by SEQ ID NO: 4 or a salt thereof, (3) a polypeptide consisting of the amino acid sequence represented by SEQ ID NO: 6 or a salt thereof, (4) a polypeptide consisting of the amino acid sequence represented by SEQ ID NO: 7 or a salt thereof, (5) a polypeptide consisting of the amino acid sequence represented by SEQ ID NO: 8 or a salt thereof, (6) a polypeptide consisting of the amino acid sequence represented by SEQ ID NO: 9 or a salt thereof, or (7) a peptide or its salt consisting of a) an amino acid sequence in positions 19 to 24, positions 5 to 24, positions 1 to 20, positions 5 to 20 or positions 5 to 21 in the amino acid sequence represented by SEQ ID NO: 3, SEQ ID NO: 4 or SEQ ID NO: 8,

[5] the screening method according to the above-mentioned [1], wherein the amino group of an N-terminus methionine residue of humanin is formylated,

[6] the screening method according to the above-mentioned [1], wherein humanin is a polypeptide, or its salt, consisting of the amino acid sequence represented by SEQ ID NO: 3, SEQ ID NO: 4, SEQ ID NO: 6, SEQ ID NO: 7, SEQ ID NO: 8 or SEQ ID NO: 9, wherein the amino group of an N-terminal methionine residue thereof is formylated,

[7] a kit for screening a compound or its salt that alters the binding property or signal transduction between (1) a G protein-coupled receptor protein comprising the same or substantially the same amino acid sequence as the amino acid sequence represented by SEQ ID NO: 1, SEQ ID NO: 10, SEQ ID NO: 12 or SEQ ID NO: 14 or a salt thereof and (2) humanin or a salt thereof, which comprises the receptor protein, a partial peptide thereof or a salt thereof and humanin or a salt thereof,

[8] a compound or its salt that alters the binding property or signal transduction between humanin or a salt thereof and a G protein-coupled receptor protein comprising the same or substantially the same amino acid sequence as the amino acid sequence represented by SEQ ID NO: 1, SEQ ID NO: 10, SEQ ID NO: 12 or SEQ ID NO: 14 or a salt thereof, which is obtainable using the screening method according to the above-mentioned [1] or the screening kit according to the above-mentioned [7],

[9] the compound according to the above-mentioned [8], which is an agonist,

[10] the compound according to the above-mentioned [8], which is an antagonist,

[11] a pharmaceutical preparation comprising a compound or its salt that alters the binding property or signal transduction between humanin or a salt thereof and a G protein-coupled receptor protein comprising the same or substantially the same amino acid sequence as the amino acid sequence represented by SEQ ID NO: 1, SEQ ID NO: 10, SEQ ID NO: 12 or SEQ ID NO: 14 or a salt thereof,

[12] a prophylactic/therapeutic agent for nerve degeneration diseases or brain function disorders, which comprises an agonist to a G protein-coupled receptor protein comprising the same or substantially the same amino acid sequence as the amino acid sequence represented by SEQ ID NO: 1, SEQ ID NO: 10, SEQ ID NO: 12 or SEQ ID NO: 14 or to a salt thereof.

[13] the prophylactic/therapeutic agent according to the above-mentioned [12], which is a prophylactic/therapeutic agent for Alzheimer's disease, Parkinson's disease, Down's syndrome, amyotrophic lateral sclerosis, prion disease, Creutzfeldt-Jakob disease, Huntington's disease, diabetic neuropathy, multiple sclerosis, cerebral infarction, cerebral hemorrhage, subarachnoid hemorrhage, ischemic cerebral disease, epidural hematoma or subdural hematoma,

[14] an apotosis inhibitor comprising an agonist to a G protein-coupled receptor protein comprising the same or substantially the same amino acid sequence as the amino acid sequence represented by SEQ ID NO: 1, SEQ ID NO: 10, SEQ ID NO: 12 or SEQ ID NO: 14 or to a salt thereof,

[15] a prophylactic/therapeutic agent for nerve degeneration diseases or brain function disorders, which comprises a G protein-coupled receptor protein comprising the same or substantially the same amino acid sequence as the amino acid sequence represented by SEQ ID NO: 1, SEQ ID NO: 10 or SEQ ID NO: 14, or a partial salt thereof or a salt thereof,

[16] the prophylactic/therapeutic agent according to the above-mentioned [15], which is a prophylactic/therapeutic agent for Alzheimer's disease, Parkinson's disease, Down's syndrome, amyotrophic lateral sclerosis, prion disease, Creutzfeldt-Jakob disease, Huntington's disease, diabetic neuropathy, multiple sclerosis, cerebral infarction, cerebral hemorrhage, subarachnoid hemorrhage, ischemic cerebral disease, epidural hematoma or subdural hematoma,

[17] an apotosis inhibitor comprising a G protein-coupled receptor protein comprising the same or substantially the same amino acid sequence as the amino acid sequence represented by SEQ ID NO: 1, SEQ ID NO: 10, SEQ ID NO: 12 or SEQ ID NO: 14, or a partial peptide thereof or a salt thereof.

18. A prophylactic/therapeutic agent for nerve degeneration diseases or brain function disorders, which comprises a polynucleotide comprising a polynucleotide encoding a G protein-coupled receptor protein comprising the same or substantially the same amino acid sequence as the amino acid sequence represented by SEQ ID NO: 1, SEQ ID NO: 10, SEQ ID NO: 12 or SEQ ID NO: 14 or a partial peptide thereof,

[19] the prophylactic/therapeutic agent according to the above-mentioned [18], which is a prophylactic/therapeutic agent for Alzheimer's disease, Parkinson's disease, Down's syndrome, amyotrophic lateral sclerosis, prion disease, Creutzfeldt-Jakob disease, Huntington's disease, diabetic neuropathy, multiple sclerosis, cerebral infarction, cerebral hemorrhage, subarachnoid hemorrhage, ischemic cerebral disease, epidural hematoma or subdural hematoma,

[20] an apotosis inhibitor comprising a polynucleotide comprising a polynucleotide encoding a G protein-coupled receptor protein comprising the same or substantially the same amino acid sequence as the amino acid sequence represented by SEQ ID NO: 1, SEQ ID NO: 10, SEQ ID NO: 12 or SEQ ID NO: 14 or a partial peptide thereof,

[21] a diagnostic agent for diseases involving nerve degeneration, which comprises a polynucleotide comprising a polynucleotide encoding a G protein-coupled receptor protein comprising the same or substantially the same amino acid sequence as the amino acid sequence represented by SEQ ID NO: 1, SEQ ID NO: 10, SEQ ID NO: 12 or SEQ ID NO: 14 or a partial peptide thereof,

[22] the diagnostic agent according to the above-mentioned [21], which is a diagnostic agent for Alzheimer's disease, Parkinson's disease, Down's syndrome, amyotrophic lateral sclerosis, prion disease, Creutzfeldt-Jakob disease, Huntington's disease, diabetic neuropathy, multiple sclerosis, cerebral infarction, cerebral hemorrhage, subarachnoid hemorrhage, ischemic cerebral disease, epidural hematoma or subdural hematoma,

[23] a diagnostic agent for diseases involving nerve degeneration, which comprises an antibody to a G protein-coupled receptor protein comprising the same or substantially the same amino acid sequence as the amino acid sequence represented by SEQ ID NO: 1, SEQ ID NO: 10, SEQ ID NO: 12 or SEQ ID NO: 14, or to a partial peptide thereof or to a salt thereof,

[24] the diagnostic agent according to the above-mentioned [23], which is a diagnostic agent for Alzheimer's disease, Parkinson's disease, Down's syndrome, amyotrophic lateral sclerosis, prion disease, Creutzfeldt-Jakob disease, Huntington's disease, diabetic neuropathy, multiple sclerosis, cerebral infarction, cerebral hemorrhage, subarachnoid hemorrhage, ischemic cerebral disease, epidural hematoma or subdural hematoma.

[25] a method of screening a compound or its salt preventing and treating nerve degeneration diseases or brain function disorders by increasing the expression level of a G protein-coupled receptor protein comprising the same or substantially the same amino acid sequence as the amino acid sequence represented by SEQ ID NO: 1, SEQ ID NO: 10, SEQ ID NO: 12 or SEQ ID NO: 14, which comprises using a polynucleotide comprising a polynucleotide encoding the G protein-coupled receptor protein or a partial peptide thereof.

[26] a kit for screening a compound or its salt preventing and treating nerve degeneration diseases or brain function disorders by increasing the expression level of a G protein-coupled receptor protein comprising the same or substantially the same amino acid sequence as the amino acid sequence represented by SEQ ID NO: 1, SEQ ID NO: 10, SEQ ID NO: 12 or SEQ ID NO: 14, which comprises a polynucleotide comprising a polynucleotide encoding the G protein-coupled receptor protein or a partial peptide thereof,

[27] a compound or its salt preventing and treating nerve degeneration diseases or brain function disorders by increasing the expression level of a G protein-coupled receptor protein comprising the same or substantially the same amino acid sequence as the amino acid sequence represented by SEQ ID NO: 1 or a partial peptide thereof, which is obtainable using the screening method according to the above-mentioned [25] or the screening kit according to the above-mentioned [26],

[28] a prophylactic/therapeutic agent for nerve degeneration diseases or brain function disorders, which comprises a compound or its salt increasing the expression level of a G protein-coupled receptor protein comprising the same or substantially the same amino acid sequence as the amino acid sequence represented by SEQ ID NO: 1, SEQ ID NO: 10, SEQ ID NO: 12 or SEQ ID NO: 14, or a partial peptide thereof,

[29] the prophylactic/therapeutic agent according to the above-mentioned [28], which is a prophylactic/therapeutic agent for Alzheimer's disease, Parkinson's disease, Down's syndrome, amyotrophic lateral sclerosis, prion disease, Creutzfeldt-Jakob disease, Huntington's disease, diabetic neuropathy, multiple sclerosis, cerebral infarction, cerebral hemorrhage, subarachnoid hemorrhage, ischemic cerebral disease, epidural hematoma or subdural hematoma,

[30] a method of screening a compound or its salt inhibiting apotosis by increasing the expression level of a G protein-coupled receptor protein comprising the same or substantially the same amino acid sequence as the amino acid sequence represented by SEQ ID NO: 1, SEQ ID NO: 10, SEQ ID NO: 12 or SEQ ID NO: 14, which comprises using a polynucleotide comprising a polynucleotide encoding the G protein-coupled receptor protein or a partial peptide thereof.

[31] a kit for screening a compound or its salt inhibiting apotosis by increasing the expression level of a G protein-coupled receptor protein comprising the same or substantially the same amino acid sequence as the amino acid sequence represented by SEQ ID NO: 1, SEQ ID NO: 10, SEQ ID NO: 12 or SEQ ID NO: 14, which comprises a polynucleotide comprising a polynucleotide encoding the G protein-coupled receptor protein or a partial peptide thereof,

[32] a compound or its salt inhibiting apotosis by increasing the expression level of a G protein-coupled receptor protein comprising the same or substantially the same amino acid sequence as the amino acid sequence represented by SEQ ID NO: 1, SEQ ID NO: 10, SEQ ID NO: 12 or SEQ ID NO: 14 or a partial peptide thereof, which is obtainable using the screening method according to the above-mentioned [30] or the screening kit according to the above-mentioned [31],

[33] an apotosis inhibitor comprising a compound or its salt increasing the expression level of a G protein-coupled receptor protein comprising the same or substantially the same amino acid sequence as the amino acid sequence represented by SEQ ID NO: 1, SEQ ID NO: 10, SEQ ID NO: 12 or SEQ ID NO: 14 or a partial peptide thereof,

[34] a method of screening an agonist or antagonist to a G protein-coupled receptor protein comprising the same or substantially the same amino acid sequence as the amino acid sequence represented by SEQ ID NO: 1, SEQ ID NO: 10, SEQ ID NO: 12 or SEQ ID NO: 14 or to a salt thereof, which comprises using a compound or its salt that alters the binding property or signal transduction between (1) the G protein-coupled receptor protein, a partial peptide or a salt thereof and (2) humanin or a salt thereof,

[35] a method of screening an agonist to a G protein-coupled receptor protein comprising the same or substantially the same amino acid sequence as the amino acid sequence represented by SEQ ID NO: 1, SEQ ID NO: 10 or SEQ ID NO: 12 or to a salt thereof, which comprises measuring an inhibitory activity on intracellular cAMP formation upon bringing a test compound into contact with cells containing the receptor protein,

[36] a method (i) for prevention/treatment of nerve degeneration diseases or brain function disorders, a method (ii) for prevention/treatment of Alzheimer's disease, Parkinson's disease, Down's syndrome, amyotrophic lateral sclerosis, prion disease, Creutzfeldt-Jakob disease, Huntington's disease, diabetic neuropathy, multiple sclerosis, cerebral infarction, cerebral hemorrhage, subarachnoid hemorrhage, ischemic cerebral disease, epidural hematoma or subdural hematoma, or a method (iii) for inhibiting apotosis, which comprises administering into a mammal an effective amount of (1) a G protein-coupled receptor protein comprising the same or substantially the same amino acid sequence as the amino acid sequence represented by SEQ ID NO: 1, SEQ ID NO: 10, SEQ ID NO: 12 or SEQ ID NO: 14, or a partial peptide thereof or a salt thereof, (2) a polynucleotide comprising a polynucleotide encoding a G protein-coupled receptor protein comprising the same or substantially the same amino acid sequence as the amino acid sequence represented by SEQ ID NO: 1, SEQ ID NO: 10, SEQ ID NO: 12 or SEQ ID NO: 14 or a partial peptide thereof, or (3) an agonist to a G protein-coupled receptor protein comprising the same or substantially the same amino acid sequence as the amino acid sequence represented by SEQ ID NO: 1, SEQ ID NO: 10, SEQ ID NO: 12 or SEQ ID NO: 14 or to a salt thereof,

[37] use of (1) a G protein-coupled receptor protein comprising the same or substantially the same amino acid sequence as the amino acid sequence represented by SEQ ID NO: 1, SEQ ID NO: 10, SEQ ID NO: 12 or SEQ ID NO: 14, or a partial peptide thereof or a salt thereof, (2) a polynucleotide comprising a polynucleotide encoding a G protein-coupled receptor protein comprising the same or substantially the same amino acid sequence as the amino acid sequence represented by SEQ ID NO: 1, SEQ ID NO: 10, SEQ ID NO: 12 or SEQ ID NO: 14 or a partial peptide thereof, or (3) an agonist to a G protein-coupled receptor protein comprising the same or substantially the same amino acid sequence as the amino acid sequence represented by SEQ ID NO: 1, SEQ ID NO: 10, SEQ ID NO: 12 or SEQ ID NO: 14 in order to produce (i) a prophylactic/therapeutic agent for nerve degeneration diseases or brain function disorders, (ii) a prophylactic/therapeutic agent for Alzheimer's disease, Parkinson's disease, Down's syndrome, amyotrophic lateral sclerosis, prion disease, Creutzfeldt-Jakob disease, Huntington's disease, diabetic neuropathy, multiple sclerosis, cerebral infarction, cerebral hemorrhage, subarachnoid hemorrhage, ischemic cerebral diseases, epidural hematoma or subdural hematoma, or (iii) an apotosis inhibitor,

[38] humanin having an N-terminal methionine residue whose amino group is formylated, or a salt thereof,

[39] the humanin according to the above-mentioned [38] or its salt, which is a polypeptide, or its salt, consisting of the amino acid sequence having an N-terminal methionine residue whose amino group is formylated, which is represented by SEQ ID NO: 3, SEQ ID NO: 4, SEQ ID NO: 6, SEQ ID NO: 7, SEQ ID NO: 8 or SEQ ID NO: 9,

[40] a polypeptide or its salt consisting of the amino acid sequence represented by SEQ ID NO: 6 (human humanin (1-21)) or SEQ ID NO: 9 (rat humanin (1-21)),

[41] a pharmaceutical preparation comprising the humanin or its salt according to the above-mentioned [38] or the polypeptide or its salt according to the above-mentioned [40],

[42] the pharmaceutical preparation according to the above-mentioned [41], which is a prophylactic/therapeutic agent for nerve degeneration diseases or brain function disorders,

[43] the pharmaceutical preparation according to the above-mentioned [41], which is a prophylactic/therapeutic agent for Alzheimer's disease, Parkinson's disease, Down's syndrome, amyotrophic lateral sclerosis, prion disease, Creutzfeldt-Jakob disease, Huntington's disease, diabetic neuropathy, multiple sclerosis, cerebral infarction, cerebral hemorrhage, subarachnoid hemorrhage, ischemic cerebral disease, epidural hematoma or subdural hematoma,

[44] the pharmaceutical preparation according to the above-mentioned [41], which is an apotosis inhibitor,

[45] a method (i) for prevention/treatment of nerve degeneration diseases or brain function disorders, a method (ii) for prevention/treatment of Alzheimer's disease, Parkinson's disease, Down's syndrome, amyotrophic lateral sclerosis, prion disease, Creutzfeldt-Jakob disease, Huntington's disease, diabetic neuropathy, multiple sclerosis, cerebral infarction, cerebral hemorrhage, subarachnoid hemorrhage, ischemic cerebral disease, epidural hematoma or subdural hematoma, or a method (iii) for inhibiting apotosis, which comprises administering into a mammal an effective amount of the humanin or its salt according to the above-mentioned [38 or the polypeptide or its salt according to the above-mentioned [40], and

[46] use of the humanin or its salt according to the above-mentioned [38] or the polypeptide or its salt according to the above-mentioned [40] in order to produce (i) a prophylactic/therapeutic agent for nerve degeneration diseases or brain function disorders, (ii) a prophylactic/therapeutic agent for Alzheimer's disease, Parkinson's disease, Down's syndrome, amyotrophic lateral sclerosis, prion disease, Creutzfeldt-Jakob disease, Huntington's disease, diabetic neuropathy, multiple sclerosis, cerebral infarction, cerebral hemorrhage, subarachnoid hemorrhage, ischemic cerebral diseases, epidural hematoma or subdural hematoma, or (iii) an apotosis inhibitor.

Further, the present invention provides:

[47] the screening method according to the above-mentioned [1], which comprises comparing the case (i) where a G protein-coupled receptor protein comprising the same or substantially the same amino acid sequence as the amino acid sequence represented by SEQ ID NO: 1, SEQ ID NO: 10, SEQ ID NO: 12 or SEQ ID NO: 14 (hereinafter abbreviated as FPRL1/FPRL2), a partial peptide thereof or a salt thereof is brought into contact with humanin or a salt thereof and the case (ii) where FPRL1/FPRL2, a partial peptide or a salt thereof is contacted with humanin or a salt thereof and a test compound,

[48] the screening method according to the above-mentioned [1], which comprises measuring and comparing the amount of labeled humanin or a salt thereof bound to FPRL1/FPRL2, a partial peptide thereof or a salt thereof between the case (i) where labeled humanin or a salt thereof is brought into contact with FPRL1/FPRL2, a partial peptide or a salt thereof and the case (ii) where labeled humanin or a salt thereof and a test sample are brought into contact with FPRL1/FPRL2, a partial peptide or a salt thereof,

[49] the screening method according to the above-mentioned [1], which comprises measuring and comparing the amount of labeled humanin or a salt thereof bound to cells containing FPRL1/FPRL2 between the case (i) where labeled humanin or a salt thereof is brought into contact with the cells and the case (ii) where labeled humanin or a salt thereof and a test compound are brought into contact with the cells,

[50] the screening method according to the above-mentioned [1], which comprises measuring and comparing the amount of labeled humanin or a salt thereof bound to a cell membrane fraction containing FPRL1/FPRL2 between the case (i) where labeled humanin or a salt thereof is brought into contact with the cell membrane fraction and the case (ii) where labeled humanin or a salt thereof and a test compound are brought into contact with the cell membrane fraction,

[51] the screening method according to the above-mentioned [1], which comprises measuring and comparing the amount of labeled humanin or a salt thereof bound to FPRL1/FPRL2 between the case (i) where labeled humanin or a salt thereof is brought into contact with FPRL1/FPRL2 expressed on a cell membrane of a cultured transformant transformed with a recombinant vector comprising DNA comprising DNA encoding FPRL1/FPRL2 and the case (ii) labeled humanin or a salt thereof and a test compound are brought into contact with FPRL1/FPRL2 expressed on a cell membrane of the transformant,

[52] the screening method according to the above-mentioned [1], which comprises measuring and comparing the FPRL1/FPRL2-mediated cell-stimulating activity between the case (1) where a compound or its salt that activates FPRL1/FPRL2 is brought into contact with cells containing FPRL1/FPRL2 and the case (2) where a compound or its salt that activates FPRL1/FPRL2, and a test compound, are brought into contact with cells containing FPRL1/FPRL2,

[53] the screening method according to the above-mentioned [1], which comprises measuring and comparing the FPRL1/FPRL2-mediated cell-stimulating activity between the case where a compound or its salt that activates FPRL1 or FPRL2 is brought into contact with FPRL1/FPRL2 expressed on a cell membrane of a cultured transformant transformed with a recombinant vector comprising DNA comprising DNA encoding FPRL1/FPRL2 and the case where a compound or its salt that activates FPRL1 or FPRL2, and a test compound, are brought into contact with FPRL1/FPRL2 expressed on a cell membrane of the transformant,

[54] the screening method according to the above-mentioned [52] or [53], wherein the compound that activates FPRL1 or FPRL2 is humanin,

[55] the screening kit according to the above-mentioned [7], which comprises cells containing FPRL1 or FPRL2 or a cell membrane fraction of the cells, and

[56] the screening kit according to the above-mentioned [7], which comprises FPRL1/FPRL2 expressed on a cell membrane induced by culturing a transformant transformed with a recombinant vector comprising DNA comprising DNA encoding FPRL1/FPRL2

BRIEF DESCRIPTION OF THE DRAWINGS

FIG. 3 shows EC$_{50}$ values (nM) determined by measuring the amount of intracellular cAMP upon reacting various ligands with CHO cells expressing each receptor protein. Sample refers to a ligand sample used. Formyl-Humanin refers to human humanin (1-24) consisting of the amino acid sequence represented by SEQ ID NO: 3 wherein Met of the N-terminus thereof is formylated. mt-formyl-Humanin refers to human humanin (1-21) consisting of the amino acid sequence represented by SEQ ID NO: 6, wherein Met at the N-terminus thereof is formylated. mt-formyl-rattin refers to rat humanin (1-21) consisting of the amino acid sequence represented by SEQ ID NO: 9, wherein Met at the N-terminus thereof is formylated. Humanin refers to human humanin (1-24) consisting of the amino acid sequence represented by SEQ ID NO: 3. [Gly$^{14}$] Humanin refers to [Gly$^{14}$]-human humanin (1-24) consisting of the amino acid sequence represented by SEQ ID NO: 4. W-Peptide refers to Trp-Lys-Tyr-Met-Val-dMet-NH$_2$ (SEQ ID NO: 24). dMet is a D form of Met. β-Amyloid (1-42) refers to β-amyloid (1-42). hFPR1 refers to human-derived FPRL. hFPRL1 refers to human-derived FPRL1. hFPRL2 refers to human-derived FPRL2. mFPRL2 refers to mouse-derived FPRL2 (FPRL1). rFPRL1 refers to rat-derived FPRL1. >10000 means 10000 nM or more.

BEST MODE FOR CARRYING OUT THE INVENTION

Figure 1:
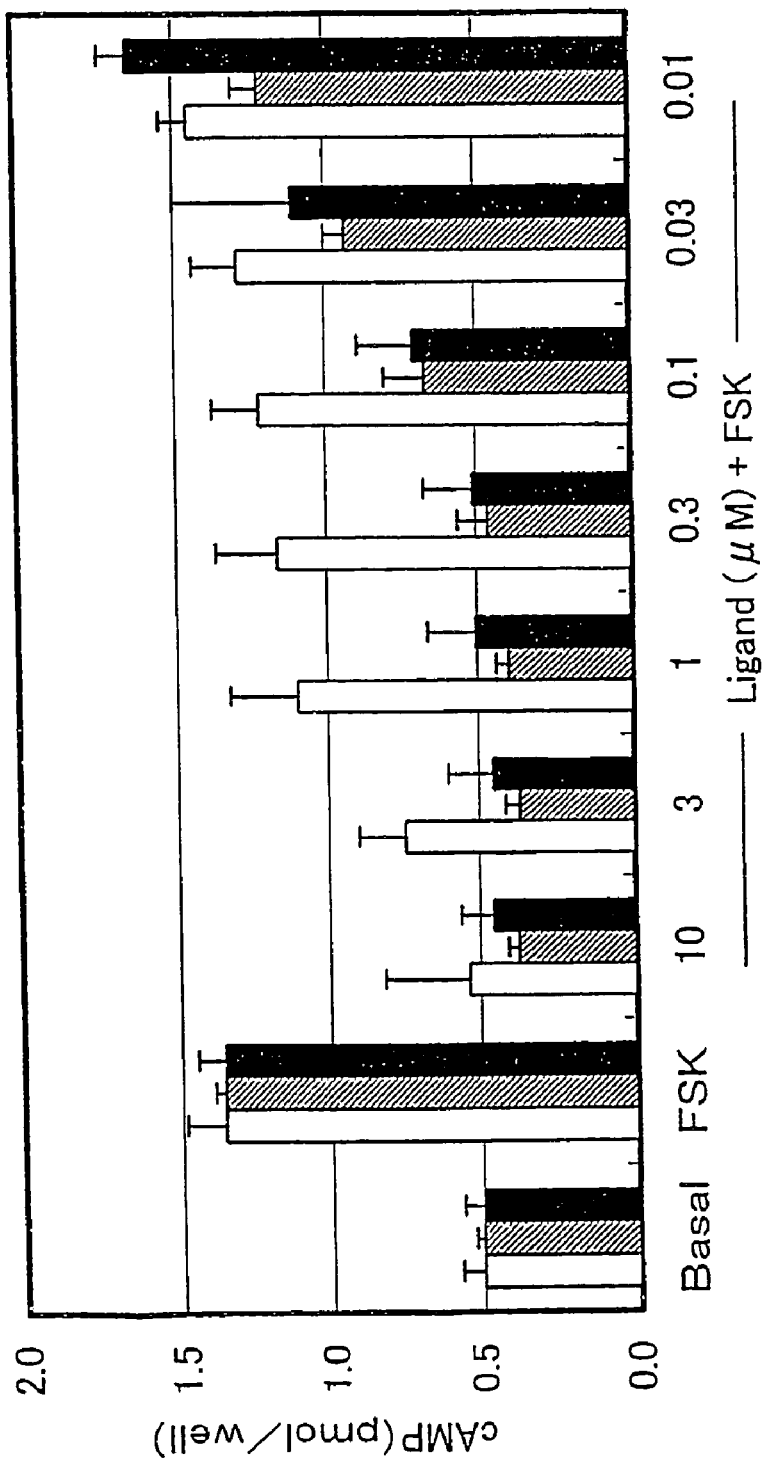
FIG. 1 shows the dose dependence of the activity of a ligand specific to CHO cells expressing FPRL1-GFP receptor by measuring an amount of intracellular cAMP. The amount of intracellular cAMP is compared after the cells were incubated in the state (Basal) not stimulated with forskolin or in the presence of 1 μM forskolin and fMLF, humanin or [Gly$^{14}$] humanin at a predetermined concentration shown in the graph. The white column shows the case where fMLF was added. The shaded column shows the case where human humanin (1-24) consisting of the amino acid sequence represented by SEQ ID NO: 3 was added. The black column shows the case where [Gly$^{14}$]-human humanin (1-24) consisting of the amino acid sequence represented by SEQ ID NO: 4 was added. Basal shows the case where forskolin (FSK) and the ligand were not added. FSK shows the case where forskolin was added. Ligand (μM)+FSK shows the case where each ligand and forskolin were added. The number on the abscissa shows the concentration (μM) of each ligand. cAMP (pmol/well) on the ordinate shows the amount of intracellular cAMP (pmol/well).

FPRL1 used in the present invention is a receptor protein comprising the same or substantially the same amino acid sequence as the amino acid sequence represented by SEQ ID NO: 1, SEQ ID NO: 10 or SEQ ID NO: 12.

FPRL2 used in the present invention is a receptor protein comprising the same or substantially the same amino acid sequence as the amino acid sequence represented by SEQ ID NO: 14.

FPRL1 or FPRL2 may be any protein derived from any cells (e.g., retina cells, liver cells, splenocytes, nerve cells, glial cells, β cells of pancreas, bone marrow cells, mesangial cells, Langerhans' cells, epidermic cells, epithelial cells, endothelial cells, fibroblasts, fibrocytes, myocytes, fat cells, immune cells (e.g., macrophage, T cells, B cells, natural killer cells, mast cells, neutrophil, basophil, eosinophil, monocyte), megakaryocyte, synovial cells, chondrocytes, bone cells, osteoblasts, osteoclasts, mammary gland cells, hepatocytes or interstitial cells, the corresponding precursor cells, stem cells, cancer cells, etc.), hemocyte type cells, or any tissues where such cells are present, e.g., brain or any region of the brain (e.g., olfactory bulb, amygdaloid nucleus, basal ganglia, hippocampus, thalamus, hypothalamus, subthalamic nucleus, cerebral cortex, medulla oblongata, cerebellum, occipital pole, frontal lobe, temporal lobe, putamen, caudate nucleus, corpus callosum, substantia nigra), spinal cord, hypophysis, stomach, pancreas, kidney, liver, gonad, thyroid, gall-bladder, bone marrow, adrenal gland skin, muscle, lung, gastrointestinal tract (e.g., large intestine and small intestine), blood vessel, heart, thymus, spleen, submandibular gland, peripheral blood, peripheral blood cells, prostate, testis, ovary, placenta, uterus, bone, joint, skeletal muscle, etc. from human and other mammals (e.g., guinea pigs, rats, mice, rabbits, swine, sheep, bovine, monkeys, etc.). The receptor protein may also be a synthetic protein.

Substantially the same amino acid sequence as that represented by SEQ ID NO: 1, SEQ ID NO: 10 or SEQ ID NO: 12 includes, for example, an amino acid sequence having at least about 85% homology, preferably at least about 90% homology and more preferably at least about 95% homology to the amino acid sequence represented by SEQ ID NO: 1, SEQ ID NO: 10 or SEQ ID NO: 12.

The protein of the present invention comprising substantially the same amino acid sequence as that represented by SEQ ID NO: 1, SEQ ID NO: 10 or SEQ ID NO: 12 includes, for example, a protein having an amino acid sequence comprising substantially the same amino acid sequence as that represented by SEQ ID NO: 1, SEQ ID NO: 10 or SEQ ID NO: 12 and having a substantially equivalent activity to that of FPRL1 consisting of the amino acid sequence represented by SEQ ID NO: 1, SEQ ID NO: 10 or SEQ ID NO: 12.

Substantially the same amino acid sequence as that represented by SEQ ID NO: 14 includes, for example, an amino acid sequence having at least about 85% homology, preferably at least about 90% homology and more preferably at least about 95% homology to the amino acid sequence represented by SEQ ID NO: 14.

The protein of the present invention comprising substantially the same amino acid sequence as that represented by SEQ ID NO: 14 includes, for example, a protein having an amino acid sequence comprising substantially the same amino acid sequence as that represented by SEQ ID NO: 14 and having a substantially equivalent activity to that of FPRL2 consisting of an amino acid sequence represented by SEQ ID NO: 14.

The homology among the amino acid sequences can be calculated using homology calculation algorism NCBI BLAST (National Center for Biotechnology Information Basic Local Alignment Search Tool) under the following conditions: expected value=10; gap is allowable; matrix=BLOSUM62; filtering=OFF.

Examples of the substantially equivalent activity include a ligand binding activity, a signal transduction activity, etc. The term "substantially equivalent" is used to mean that the nature of the activity is the same. Therefore, although it is preferred that activities such as the ligand binding and signal transduction activities, etc. be equivalent (e.g., about 0.01- to about 100-fold, preferably about 0.5- to about 20-fold, more preferably about 0.5- to about 2-fold), quantitative factors such as a level of the activity, a molecular weight of the protein, etc. may differ.

The activities such as ligand binding and signal transduction activities or the like can be determined according to a publicly known method with some modifications, for example, by the ligand determination methods or the screening methods that will be later described.

As FPRL1, proteins comprising the following amino acid sequences will be used:

a) amino acid sequences represented by SEQ ID NO: 1, SEQ ID NO: 10 or SEQ ID NO: 12, wherein 1 or more amino acids (preferably about 1 to 30 amino acids, more preferably about 1 to 10 amino acids, still more preferably several amino acids (1 to 5 amino acids)) are deleted, b) amino acid sequences represented by SEQ ID NO: 1, SEQ ID NO: 10 or SEQ ID NO: 12 to which 1 or more amino acids (preferably about 1 to 30 amino acids, more preferably about 1 to 10 amino acids, still more preferably several amino acids (1 to 5 amino acids)) are added, c) amino acid sequences represented by SEQ ID NO: 1, SEQ ID NO: 10 or SEQ ID NO: 12, wherein 1 or more amino acids (preferably about 1 to 30 amino acids, more preferably about 1 to 10 amino acids, still more preferably several amino acids (1 to 5 amino acids)) are substituted by other amino acids, and d) proteins consisting of a combination of the amino acid sequences described in the above.

As FPRL2, proteins comprising the following amino acid sequences will be used:

a) amino acid sequences represented by SEQ ID NO: 14, wherein 1 or more amino acids (preferably about 1 to 30 amino acids, more preferably about 1 to 10 amino acids, still more preferably several amino acids (1 to 5 amino acids)) are deleted, b) amino acid sequences represented by SEQ ID NO: 14 to which 1 or more amino acids (preferably about 1 to 30 amino acids, more preferably about 1 to 10 amino acids, still more preferably several amino acids (1 to 5 amino acids)) are added, c) amino acid sequences represented by SEQ ID NO: 14, wherein 1 or more amino acids (preferably about 1 to 30 amino acids, more preferably about 1 to 10 amino acids, still more preferably several amino acids (1 to 5 amino acids)) are substituted by other amino acids, and d) proteins consisting of a combination of the amino acid sequences described in the above.

Throughout the present specification, FPRL1 or FPRL2 is represented in accordance with the conventional way of describing peptides, that is, the N-terminus (amino terminus) at the left hand and the C-terminus (carboxyl terminus) at the right hand. In FPRL1 including FPRL1 comprising the amino acid sequence represented by SEQ ID NO: 1, the C-terminus is usually in the form of a carboxyl group (—COOH) or a carboxylate (—COO$^-$) but may be in the form of an amide (—CONH$_2$) or an ester (—COOR).

Examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl group such as a phenyl-$C_{1-2}$-alkyl group, e.g., benzyl, phenethyl, etc., or an α-naphthyl-$C_{1-2}$-alkyl group such as α-naphthylmethyl, etc.; and the like. In addition, pivaloyloxymethyl or the like, which is used widely as an ester for oral administration, may also be used.

When FPRL1 or FPRL2 has a carboxyl group (or a carboxylate) at a position other than the C-terminus, it may be amidated or esterified, and such an amide or ester is also included within FPRL1 or FPRL2 of the present invention. The ester group may be the same group as that described with respect to the C-terminus described above.

Furthermore, examples of FPRL1 or FPRL2 include variants of the above proteins, wherein the amino group at the N-terminal methionine residue of the protein supra is protected with a protecting group (for example, a $C_{1-6}$ acyl group such as a $C_{2-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{2-6}$ alkanoyl group, e.g., formyl group, acetyl group, etc.), or conjugated proteins such as glycoproteins bound to sugar chains.

Specific examples of FPRL1 of the present invention which can be used include, for example, human-derived FPRL1 consisting of the amino acid sequence represented by SEQ ID NO: 1, rat-derived FPRL1 consisting of the amino acid sequence represented by SEQ ID NO: 10, mouse-derived FPRL2 consisting of the amino acid sequence represented by SEQ ID NO: 12, etc. The human-derived FPRL1 is a known protein described in J. Biol. Chem. 267(11), 7637–7643 (1992). The mouse-derived FPRL2 is a known protein described in J. Immunol. 169, 3363–3369 (2002).

Specific examples of FPRL2 of the present invention which can be used include, for example, human-derived FPRL2 consisting of the amino acid sequence represented by SEQ ID NO: 14, etc. The human-derived FPRL2 is a known protein described in Genomics 13(2), 437–440 (1992).

Partial peptides of FPRL1 or FPRL2 (hereinafter sometimes simply referred to as the partial peptide of the present invention) may be any partial peptides of FPRL1 or FPRL2 described above, and for example, those having a site exposed to the outside of a cell membrane and having a receptor binding activity substantially equivalent to that of FPRL1 or FPRL2 can be used.

Specifically, the partial peptide of FPRL1 having the amino acid sequence represented by SEQ ID NO: 1, SEQ ID NO: 10 or SEQ ID NO: 12 or the partial peptide of FPRL2 having the amino acid sequence represented by SEQ ID NO: 14 is a peptide containing the parts analyzed to be extracellular domains (hydrophilic domains) in hydrophobic plotting analysis. A peptide containing a hydrophobic domain in part can be used as well. In addition, the peptide may contain each domain separately or plural domains together.

In the receptor protein of the present invention, preferred partial peptides are those having at least 20, preferably at least 50, and more preferably at least 100 amino acids, in the amino acid sequence which constitutes the receptor protein of the present invention.

The term "substantially the same amino acid sequence" refers to an amino acid sequence having at least about 85% homology, preferably at least about 90% homology, more preferably at least about 95% homology, to the amino acid sequences mentioned therein.

The homology among the amino acid sequences can be calculated using homology calculation algorism NCBI BLAST (National Center for Biotechnology Information Basic Local Alignment Search Tool) under the following conditions: expected value=10; gap is allowable; matrix=BLOSUM62; filtering=OFF.

Herein, the term "activity substantially equivalent" refers to the same meaning as defined above. The "substantially equivalent receptor activity" can be assayed in the same manner as given above.

The partial peptide of the present invention includes partial peptides of the amino acid sequence described above, wherein 1 or more amino acids (preferably about 1 to 10 amino acids, more preferably several (1 to 5) amino acids) may be deleted; to which 1 or more amino acids (preferably about 1 to 20 amino acids, more preferably about 1 to 10 amino acids, still more preferably several (1 to 5) amino acids) may be added; or, in which 1 or more amino acids (preferably about 1 to 10 amino acids, more preferably several amino acids, still more preferably about 1 to 5 amino acids) may be substituted by other amino acids.

In the partial peptide of the present invention, the C-terminus is normally a carboxyl group (—COOH) or carboxylate (—COO⁻) but the C-terminus may be in the form of an amide (—CONH$_2$) or an ester (—COOR) (R means the same significance as described above). When the partial peptide of the present invention has carboxyl group (or carboxylate) apart from the C-terminus, a peptide which carboxyl group is amidated or esterified is also included in the partial peptide of the present invention. As the ester, for example, an ester of the C-terminus described above is used.

As in FPRL1 or FPRL2 described above, the partial peptide of the present invention further includes those in which the amino group of the N-terminal methionine residue is protected by a protecting group, those in which the N-terminal residue is cleaved in vivo and the produced glutamine residue is pyroglutaminated, those in which substituents on the side chains of amino acids in the molecule are protected by appropriate protecting groups, conjugated peptides such as so-called glycoproteins, to which sugar chains are bound, and the like.

For salts of FPRL1 or FPRL2 or the partial peptide of the present invention, preferred are salts with physiologically acceptable acids, especially physiologically acceptable acid addition salts. Examples of the salts include salts with, for example, inorganic acids (e.g., hydrochloric acid, phosphoric acid, hydrobromic acid, sulfuric acid); salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

FPRL1 of the present invention or salts thereof may be manufactured by a publicly known method used to purify a receptor protein from human and other mammalian cells or tissues described above, or by culturing a transformant that contains the DNA encoding the receptor protein of the present invention, as will be later described. Furthermore, the receptor protein or its salts may also be manufactured by the methods for synthesizing proteins or by modifications thereof, which will also be described hereinafter.

Where FPRL1 or its salts are manufactured from human or other mammalian tissues or cells, human or other mammalian tissues or cells are homogenized, then extracted with an acid or the like, and the extract obtained is isolated and purified by a combination of chromatography techniques such as reverse phase chromatography, ion exchange chromatography, and the like.

To synthesize the receptor protein of the present invention, its partial peptide, or salts or amides thereof according to the present invention, commercially available resins that are used for protein synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmehtylphenyl acetamidomethyl resin, polyacrylamide resin, 4-(2',4'-dimethoxyphenyl-hydroxymethyl)phenoxy resin, 4-(2',4'-dimethoxyphenyl-Fmoc-aminoethyl) phenoxy resin, etc. Using these resins, amino acids in which α-amino groups and functional groups on the side chains are appropriately protected are condensed on the resin in the order of the sequence of the objective protein according to various condensation methods publicly known in the art. At the end of the reaction, the receptor protein is cut out from the resin and at the same time, the protecting groups are removed. Then, intramolecular disulfide bond-forming reaction is performed in a highly diluted solution to obtain the objective protein or peptide, or amides thereof.

For condensation of the protected amino acids described above, a variety of activation reagents for protein synthesis may be used, and carbodiimides are particularly preferable. Examples of such carbodiimides include DCC, N,N'-diisopropylcarbodiimide, N-ethyl-N'-(3-dimethylaminoprolyl) carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be chosen from solvents known to be usable for protein condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to protein binding reactions and is usually selected in the range of approximately −20° C. to 50° C. The activated amino acid derivatives are used generally in an excess of 1.5 to 4 times. The condensation is examined by a test using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole.

Examples of the protecting groups used to protect the amino groups of the starting compounds include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower alkanoyl group, such as acetyl group, an aroyl group such as benzoyl group, and a group derived from carbonic acid such as benzyloxycarbonyl group, ethoxycarbonyl group, etc. Examples of a group appropriately used for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br-Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting compounds include the corresponding acid anhydrides, azides, activated esters (esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)). As the activated amino acids, in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethane-sulfonic acid or trifluoroacetic acid, or a mixture solution of these acids; a treatment with a base such as diisopropylethylamine, triethylamine, piperidine or piperazine; and reduction with sodium in liquid ammonia. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol or 1,2-ethanedithiol. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol or 1,4-butanedithiol, as well as by a treatment with an alkali such as a dilute sodium hydroxide solution and dilute ammonia.

Protection of functional groups that should not be involved in the reaction of the starting materials, protecting groups, elimination of the protecting groups and activation of functional groups involved in the reaction may be appropriately selected from publicly known groups and publicly known means.

In another method for obtaining the amides of the protein, for example, the α-carboxyl group of the carboxy terminal amino acid is first protected by amidation; the peptide (protein) chain is then extended from the amino group side to a desired length. Thereafter, a protein in which only the protecting group of the N-terminal α-amino group in the peptide chain has been eliminated from the protein and a protein in which only the protecting group of the C-terminal carboxyl group has been eliminated are prepared. The two proteins are condensed in a mixture of the solvents described above. The details of the condensation reaction are the same as described above. After the protected protein obtained by the condensation is purified, all the protecting groups are eliminated by the method described above to give the desired crude protein. This crude protein is purified by various known purification means. Lyophilization of the major fraction gives the amide of the desired protein.

To prepare the esterified protein, for example, the α-carboxyl group of the carboxy terminal amino acid is condensed with a desired alcohol to prepare the amino acid ester, which is followed by procedure similar to the preparation of the amidated protein above to give the ester form of the desired protein.

The partial peptide or its salts in FPRL1 of the present invention can be manufactured by publicly known methods for peptide synthesis, or by cleaving FPRL1 of the present invention with an appropriate peptidase. For the methods for peptide synthesis, for example, either solid phase synthesis or liquid phase synthesis may be used. That is, the partial peptide or amino acids that can construct FPRL1 of the present invention are condensed with the remaining part. Where the product contains protecting groups, these protecting groups are removed to give the desired peptide. Publicly known methods for condensation and elimination of the protecting groups are described in (i)–(v) below.

(i) M. Bodanszky & M. A. Ondetti: Peptide Synthesis, Interscience Publishers, New York (1966)

(ii) Schroeder & Luebke: The Peptide, Academic Press, New York (1965)

(iii) Nobuo Izumiya, et al.: *Peptide Gosei-no-Kiso to Jikken* (Basics and experiments of peptide synthesis), published by Maruzen Co. (1975)

(iv) Haruaki Yajima & Shunpei Sakakibara: *Seikagaku Jikken Koza* (Biochemical Experiment) 1, *Tanpakushitsu no Kagaku* (Chemistry of Proteins) IV, 205 (1977)

(v) Haruaki Yajima, ed.: *Zoku Iyakuhin no Kaihatsu* (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography and recrystallization to give the partial peptide of the present invention. When the partial peptide obtained by the above methods is in a free form, the peptide can be converted into an appropriate salt by a publicly known method; when the partial peptide is obtained in a salt form, it can be converted into a free form by a publicly known method.

FPRL2 of the present invention, partial peptides thereof or salts thereof can also be manufactured by the same methods as described above.

The polynucleotide encoding FPRL1 or FPRL2 of the present invention may be any polynucleotide so long as it comprises the nucleotide sequence (DNA or RNA, preferably DNA) encoding FPRL1 or FPRL2 of the present invention described above. Such a polynucleotide may also be any one of DNA encoding FPRL1 or FPRL2 of the present invention, RNA such as mRNA, etc., and may be double-stranded or single-stranded. Where the polynucleotide is double-stranded, it may be double-stranded DNA, double-stranded RNA or DNA:RNA hybrid. Where the polynucleotide is single-stranded, it may be a sense strand (i.e., a coding strand) or an antisense strand (i.e., a noncoding strand).

Using the polynucleotide encoding FPRL1 or FPRL2 of the present invention, mRNA of FPRL1 or FPRL2 of the present invention can be quantified by, for example, the publicly known method published in separate volume of Jikken Igaku 15 (7) "New PCR and its application" (1997), or by its modifications.

The DNA encoding FPRL1 or FPRL2 of the present invention may be any of genomic DNA, genomic DNA library, cDNA derived from the cells and tissues described above, cDNA library derived from the cells and tissues described above, and synthetic DNA. The vector to be used for the library may be any of bacteriophage, plasmid, cosmid and phagemid. The DNA may also be directly amplified by reverse transcriptase polymerase chain reaction (hereinafter abbreviated as RT-PCR) using the total RNA or mRNA fraction prepared from the cells and tissues described above.

Specifically, the DNA encoding FPRL1 of the present invention may be, for example, DNA comprising the nucleotide sequence represented by SEQ ID NO: 2, SEQ ID NO: 11 or SEQ ID NO: 13, or DNA having a nucleotide sequence hybridizable to the nucleotide sequence represented by SEQ ID NO: 2, SEQ ID NO: 11 or SEQ ID NO: 13, under highly stringent conditions and encoding a receptor protein having the activities substantially equivalent to those (e.g., a ligand binding activity, a signal transduction activity, etc.) of FPRL1 consisting of the amino acid sequence represented by SEQ ID NO: 1, SEQ ID NO: 10 or SEQ ID NO: 12.

Specific examples of the DNA hybridizable to the nucleotide sequence represented by SEQ ID NO: 2, SEQ ID NO: 11 or SEQ ID NO: 13 include, for example, DNA comprising a nucleotide sequence having at least about 85% homology, preferably at least about 90% homology and more preferably at least about 95% homology to the nucleotide sequence represented by SEQ ID NO: 2, SEQ ID NO: 11 or SEQ ID NO: 13.

The DNA encoding FPRL2 of the present invention may be, for example, DNA having the nucleotide sequence represented by SEQ ID NO: 15, or DNA having a nucleotide sequence hybridizable to the nucleotide sequence represented by SEQ ID NO: 15, under highly stringent conditions and encoding a receptor protein having the activities substantially equivalent to those (e.g., a ligand binding activity, a signal transduction activity, etc.) of FPRL2 consisting of the amino acid sequence represented by SEQ ID NO: 14.

Specific examples of the DNA hybridizable to the nucleotide sequence represented by SEQ ID NO: 15 include DNA containing a nucleotide sequence having at least about 85% homology, preferably at least about 90% homology and more preferably at least about 95% homology to the nucleotide sequence represented by SEQ ID NO: 15.

The homology among the nucleotide sequences can be calculated using homology calculation algorism NCBI BLAST (National Center for Biotechnology Information Basic Local Alignment Search Tool) under the following conditions: expected value=10; gap is allowable; filtering=ON; match score=1; mismatch score=−3.

The hybridization can be carried out by publicly known methods or by modifications of these methods, for example, according to the method described in Molecular Cloning, 2nd (J. Sambrook et al., Cold Spring Harbor Lab. Press, 1989). A commercially available library may also be used according to the instructions of the attached manufacturer's protocol. Preferably, the hybridization can be carried out under highly stringent conditions.

The highly stringent conditions used herein are, for example, those in a sodium concentration at about 19 mM to about 40 mM, preferably about 19 mM to about 20 mM at a temperature of about 50° C. to about 70° C., preferably about 60° C. to about 65° C. In particular, hybridization conditions in a sodium concentration of about 19 mM at a temperature of about 65° C. are most preferred.

More specifically, DNA comprising the nucleotide sequence represented by SEQ ID NO: 2 or the like is used as the DNA encoding human FPRL1 consisting of the amino acid sequence represented by SEQ ID NO: 1. DNA comprising the nucleotide sequence represented by SEQ ID NO: 11 or the like is used as the DNA encoding rat FPRL1 consisting of the amino acid sequence represented by SEQ ID NO: 10. DNA comprising the nucleotide sequence represented by SEQ ID NO: 13 or the like is used as the DNA encoding mouse FPRL2 consisting of the amino acid sequence represented by SEQ ID NO: 12. DNA comprising the nucleotide sequence represented by SEQ ID NO: 15 or the like is used as the DNA encoding human FPRL2 consisting of the amino acid sequence represented by SEQ ID NO: 14.

The polynucleotide comprising a part of the nucleotide sequence of the DNA encoding FPRL1 or FPRL2 of the present invention or a part of the nucleotide sequence complementary to the DNA is used to refer to not only the DNA encoding the partial peptide of the present invention described below but also to RNA.

According to the present invention, the antisense polynucleotide (nucleic acid) that can inhibit replication or expression of the FPRL1 gene or FPRL2 gene can be designed and synthesized based on the nucleotide sequence information of the cloned or determined DNA encoding FPRL1 or FPRL2. Such a polynucleotide (nucleic acid) is hybridizable to RNA of the FPRL1 gene or FPRL2 gene to inhibit the synthesis or function of the RNA or is capable of modulating/controlling the expression of the FPRL1 gene or FPRL2 gene via interaction with RNA associated with FPRL1 or RNA associated with FPRL2. Polynucleotides complementary to the selected sequences of RNA associated with FPRL1 or RNA associated with FPRL2 and polynucleotides specifically hybridizable to RNA associated with FPRL1 or RNA associated with FPRL2 are useful in modulating/controlling the in vivo and in vitro expression of the FPRL1 gene or FPRL2 gene, and are useful for the treatment or diagnosis of diseases, etc. The term "corresponding" is used to refer to homologous to or complementary to a particular sequence of the nucleotide including the gene, nucleotide sequence or nucleic acid. The term "corresponding" between nucleotides, nucleotide sequences or nucleic acids and peptides (proteins) usually refer to amino acids of a peptide (protein) under the order derived from the sequence of nucleotides (nucleic acids) or their complements. In the FPRL1 gene or FPRL2 gene, the 5' end hairpin loop, 5' end 6-base-pair repeats, 5' end untranslated region, polypeptide translation initiation codon, protein coding region, ORF translation termination codon, 3' end untranslated region, 3' end palindrome region, and 3' end hairpin loop, may be selected as preferred target regions, though any other region in the FPRL1 gene or FPRL2 gene may be selected as a target.

The relationship between the targeted nucleic acids and the polynucleotides complementary to, and hybridizable to, at least a part of the target region, can be denoted to be "antisense" to the polynucleotides in the target region. Examples of the antisense polynucleotides include polydeoxyribonucleotides containing 2-deoxy-D-ribose, polyribonucleotides containing D-ribose, any other type of polynucleotides which are N-glycosides of a purine or pyrimidine base, or other polymers containing non-nucleotide backbones (e.g., commercially available protein nucleic acids and synthetic sequence-specific nucleic acid polymers) or other polymers containing nonstandard linkages (provided that the polymers contain nucleotides having such a configuration that allows base pairing or base stacking, as is found in DNA or RNA), etc. The antisense polynucleotides may be double-stranded DNA, single-stranded DNA, double-stranded RNA, single-stranded RNA or a DNA:RNA hybrid, and may further include unmodified polynucleotides (or unmodified oligonucleotides), those with publicly known types of modifications, for example, those with labels known in the art, those with caps, methylated polynucleotides, those with substitution of one or more naturally occurring nucleotides by their analogue, those with intramolecular modifications of nucleotides such as those with uncharged linkages (e.g., methyl phosphonates, phosphotriesters, phosphoramidates, carbamates, etc.) and those with charged linkages or sulfur-containing linkages (e.g., phosphorothioates, phosphorodithioates, etc.), those having side chain groups such as proteins (nucleases, nuclease inhibitors, toxins, antibodies, signal peptides, poly-L-lysine, etc.), saccharides (e.g., monosaccharides, etc.), those with intercalators (e.g., acridine, psoralen, etc.), those containing chelators (e.g., metals, radioactive metals, boron, oxidative metals, etc.), those containing alkylating agents, those with modified linkages (e.g., α anomeric nucleic acids, etc.), and the like. Herein the terms "nucleoside". "nucleotide" and "nucleic acid" are used to refer to moieties that contain not only the purine and pyrimidine bases, but also other heterocyclic bases, which have been modified. Such modifications may include methylated purines and pyrimidines, acylated purines and pyrimidines and other heterocyclic rings. Modified nucleotides and modified nucleotides also include modifications on the sugar moiety, wherein, for example, one or more hydroxyl groups may optionally be substituted with a halogen atom(s), an aliphatic group(s), etc., or may be converted into the corresponding functional groups such as ethers, amines, or the like.

The antisense polynucleotide (nucleic acid) of the present invention is RNA, DNA or a modified nucleic acid (RNA, DNA). Specific examples of the modified nucleic acid include, but are not limited to, sulfur and thiophosphate derivatives of nucleic acids and those resistant to degradation of polynucleoside amides or oligonucleoside amides. The antisense nucleic acids of the present invention can be modified preferably based on the following design, that is, by increasing the intracellular stability of the antisense nucleic acid, increasing the cell permeability of the antisense nucleic acid, increasing the affinity of the nucleic acid to the targeted sense strand to a higher level, or minimizing the toxicity, if any, of the antisense nucleic acid.

Many of such modifications are known in the art, as disclosed in J. Kawakami, et al., Pharm. Tech. Japan, Vol. 8, p. 247, 1992; Vol. 8, p. 395, 1992; S. T. Crooke, et al. ed., Antisense Research and Applications, CRC Press, 1993; etc.

The antisense nucleic acids of the present invention may contain altered or modified sugars, bases or linkages, may also be provided in a specialized form such as liposomes or microspheres, may be applied to gene therapy, or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be attached to the polynucleotide at the 3' or 5' ends thereof and may also be attached thereto through a base, sugar, or intramolecular nucleoside linkage. Other moieties may be capping groups specifically placed at the 3' or 5' ends of the nucleic acid to prevent degradation by nucleases such as exonuclease, RNase, etc. Such capping groups include, but are not limited to, hydroxyl protecting groups known in the art, including glycols such as polyethylene glycol, tetraethylene glycol and the like.

The inhibitory action of the antisense nucleic acid can be examined using the transformant of the present invention, the gene expression system of the present invention in vivo and in vitro, or a translation system of G protein conjugated receptor protein in vivo and in vitro. The nucleic acid itself can be applied to cells by a variety of publicly known methods.

The DNA encoding the partial peptide of FPRL1 of the present invention may be any DNA insofar as it comprises the nucleotide sequence encoding the partial peptide of FPRL1 of the present invention described above. The DNA may be any of genomic DNA, genomic DNA library, cDNA derived from the cells and tissues described above, cDNA library derived from the cells and tissues described above, and synthetic DNA. The vector to be used for the library may be any of bacteriophage, plasmid, cosmid and phagemid. The DNA may also be directly amplified by reverse transcriptase polymerase chain reaction (hereinafter abbreviated as RT-PCR) using the total RNA or mRNA fraction prepared from the cells and tissues described above.

Specifically, the DNA encoding the partial peptide of FPRL1 of the present invention may be, for example, (1) DNA having a partial nucleotide sequence of DNA having the nucleotide sequence represented by SEQ ID NO: 2, SEQ ID NO: 11 or SEQ ID NO: 13, or (2) DNA having a nucleotide sequence hybridizable to the nucleotide sequence represented by SEQ ID NO: 2, SEQ ID NO: 11 or SEQ ID NO: 13, under highly stringent conditions and having a partial nucleotide sequence of DNA encoding a receptor protein having the activities substantially equivalent to those (e.g., a ligand binding activity, a signal transduction activity, etc.) of FPRL1 consisting of the amino acid sequence represented by SEQ ID NO: 1, SEQ ID NO: 10 or SEQ ID NO: 12.

The DNA hybridizable to the nucleotide sequence represented by SEQ ID NO: 2, SEQ ID NO: 11 or SEQ ID NO: 13 may be, for example, DNA containing a nucleotide sequence having at least about 85% homology, preferably at least about 90% homology and more preferably at least about 95% homology to the nucleotide sequence represented by SEQ ID NO: 2, SEQ ID NO: 11 or SEQ ID NO: 13.

The DNA encoding the partial peptide of FPRL2 of the present invention may be, for example, (1) DNA having a partial nucleotide sequence of DNA having the nucleotide sequence represented by SEQ ID NO: 15, or (2) DNA having a nucleotide sequence hybridizable to the nucleotide sequence represented by SEQ ID NO: 15 under highly stringent conditions and having a partial nucleotide sequence of DNA encoding a receptor protein having the activities substantially equivalent to those (e.g., a ligand binding activity, a signal transduction activity, etc.) of FPRL2 consisting of the amino acid sequence represented by SEQ ID NO: 14.

Specific examples of the DNA hybridizable to the nucleotide sequence represented by SEQ ID NO: 15 include DNA containing a nucleotide sequence having at least about 85% homology, preferably at least about 90% homology and more preferably at least about 95% homology to the nucleotide sequence represented by SEQ ID NO: 15.

The homology among the nucleotide sequences can be calculated using homology calculation algorism NCBI BLAST (National Center for Biotechnology Information Basic Local Alignment Search Tool) under the following conditions: expected value=10; gap is allowable; filtering=ON; match score=1; mismatch score=−3.

The hybridization can be carried out by publicly known methods or by modifications of these methods, for example, according to the method described in Molecular Cloning, 2nd (J. Sambrook et al., Cold Spring Harbor Lab. Press, 1989). A commercially available library may also be used according to the instructions of the attached manufacturer's protocol. Preferably, the hybridization can be carried out under highly stringent conditions.

The highly stringent conditions used herein are, for example, those in a sodium concentration at about 19 mM to about 40 mM, preferably about 19 mM to about 20 mM at a temperature of about 50° C. to about 70° C., preferably about 60° C. to about 65° C. In particular, hybridization conditions in a sodium concentration of about 19 mM at a temperature of about 65° C. are most preferred.

For cloning of the DNA that completely encodes FPRL1 of the present invention or its partial peptide (hereinafter sometimes collectively referred to as FPRL1 of the present invention) or FPRL2 of the present invention or its partial peptide (hereinafter sometimes collectively referred to as FPRL2 of the present invention), the DNA may be either amplified by PCR using synthetic DNA primers containing a part of the nucleotide sequence of FPRL1 or FPRL2 of the present invention, or the DNA inserted into an appropriate vector can be selected by hybridization with a labeled DNA fragment or synthetic DNA that encodes a part or entire region of FPRL1 or FPRL2 of the present invention. The hybridization can be carried out, for example, according to the method described in Molecular Cloning, 2nd, J. Sambrook et al., Cold Spring Harbor Lab. Press, 1989. The hybridization may also be performed using commercially available library in accordance with the protocol described in the attached instructions.

Conversion of the nucleotide sequence of the DNA can be effected by publicly known methods such as the ODA-LA PCR method, the gapped duplex method or the Kunkel method or its modification by using a publicly known kit available as Mutan™-super Express Km or Mutan™-K (both manufactured by Takara Shuzo Co., Ltd.).

The cloned DNA encoding FPRL1 or FPRL2 can be used as it is, depending upon purpose or if desired after digestion with a restriction enzyme or after addition of a linker thereto. The DNA may have ATG as a translation initiation codon at the 5' end thereof and may further have TAA, TGA or TAG as a translation termination codon at the 3' end thereof. These translation initiation and termination codons may also be added by using an appropriate synthetic DNA adapter.

The expression vector for FPRL1 or FPRL2 of the present invention can be manufactured, for example, by (a) excising the desired DNA fragment from the DNA encoding FPRL1 or FPRL2 of the present invention, and then (b) ligating the DNA fragment with an appropriate expression vector downstream from a promoter in the vector. Examples of the vector include plasmids derived form *E. coli* (e.g., pBR322, pBR325, pUC12, pUC13), plasmids derived from *Bacillus* subtilis (e.g., pUBI10, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNAI/Neo, etc.

The promoter used in the present invention may be any promoter if it matches well with a host to be used for gene expression. In the case of using animal cells as the host, examples of the promoter include SRα promoter, SV40 promoter, LTR promoter, CMV promoter, HSV-TK promoter, etc.

Among them, CMV (cytomegalovirus) promoter or SRα promoter is preferably used. Where the host is bacteria of the genus *Escherichia*, preferred examples of the promoter include trp promoter, lac promoter, recA promoter, $\lambda P_L$ promoter, lpp promoter etc. In the case of using bacteria of the genus *Bacillus* as the host, preferred example of the promoter are SPO1 promoter, SPO2 promoter and penP promoter. When yeast is used as the host, preferred examples of the promoter are PHO5 promoter, PGK promoter, GAP promoter and ADH promoter. When insect cells are used as the host, preferred examples of the promoter include polyhedrin prompter and P10 promoter.

In addition to the foregoing examples, the expression vector may further optionally contain an enhancer, a splicing signal, a polyA addition signal, a selection marker, SV40 replication origin (hereinafter sometimes abbreviated as SV40ori) etc. Examples of the selection marker include dihydrofolate reductase (hereinafter sometimes abbreviated as dhfr) gene [methotrexate (MTX) resistance], ampicillin resistant gene (hereinafter sometimes abbreviated as $Amp^r$), neomycin resistant gene (hereinafter sometimes abbreviated as $Neo^r$, G418 resistance), etc. In particular, when dhfr gene is used as the selection marker in dhfr gene-deficient Chinese hamster's cells, selection can also be made on thymidine free media.

If necessary and desired, a signal sequence that matches with a host is added to the N-terminus of the receptor protein of the present invention. Examples of the signal sequence that can be used are Pho A signal sequence, OmpA signal sequence, etc. in the case of using bacteria of the genus *Escherichia* as the host; α-amylase signal sequence, subtilisin signal sequence, etc. in the case of using bacteria of the genus *Bacillus* as the host; MFα signal sequence, SUC2 signal sequence, etc. in the case of using yeast as the host; and insulin signal sequence, α-interferon signal sequence, antibody molecule signal sequence, etc. in the case of using animal cells as the host, respectively.

Using the vector comprising the DNA encoding FPRL1 or FPRL2 of the present invention thus constructed, transformants can be manufactured.

Examples of the host, which may be employed, are bacteria belonging to the genus *Escherichia*, bacteria belonging to the genus *Bacillus*, yeast, insect cells, insects and animal cells, etc.

Specific examples of the bacteria belonging to the genus *Escherichia* include *Escherichia coli* K12 DH1 (Proc. Natl. Acad. Sci. U.S.A., 60, 160 (1968)), JM103 (Nucleic Acids Research, 9, 309 (1981)), JA221 (Journal of Molecular Biology, 120, 517 (1978)), HB101 (Journal of Molecular Biology, 41, 459 (1969)), C600 (Genetics, 39, 440 (1954)), etc.

Examples of the bacteria belonging to the genus *Bacillus* include *Bacillus subtilis* MI114 (Gene, 24, 255 (1983)), 207-21 (Journal of Biochemistry, 95, 87 (1984)), etc.

Examples of yeast include *Saccharomyces cereviseae* AH22, AH22R⁻, NA87-11A, DKD-5D, 20B-12, *Schizosaccharomyces pombe* NCYC1913, NCYC2036, *Pichia pastoris*, etc.

Examples of insect cells include, for the virus AcNPV, *Spodoptera frugiperda* cells (Sf cells), MG1 cells derived from mid-intestine of *Trichoplusia ni*, High Five™ cells derived from egg of *Trichoplusia ni*, cells derived from *Mamestra brassicae*, cells derived from *Estigmena acrea*, etc.; and for the virus BmNPV, *Bombyx mori* N cells (BmN cells), etc. are used. Examples of the Sfcell which can be used are Sf9 cells (ATCC CRL1711) and Sf21 cells (both cells are described in Vaughn, J. L. et al., In Vivo, 13, 213–217 (1977).

As the insect, for example, a larva of *Bombyx mori* can be used (Maeda, et al., Nature, 315, 592 (1985)).

Examples of animal cells include monkey cells COS-7, Vero, Chinese hamster cells CHO (hereinafter referred to as CHO cells), dhfr gene deficient Chinese hamster cells CHO (hereinafter simply referred to as CHO(dhfr⁻) cell), mouse L cells, mouse AtT-20, mouse myeloma cells, rat GH3, human FL cells, etc.

Bacteria belonging to the genus *Escherichia* can be transformed, for example, by the method described in Proc. Natl. Acad. Sci. U.S.A., 69, 2110 (1972) or Gene, 17, 107 (1982).

Bacteria belonging to the genus *Bacillus* can be transformed, for example, by the method described in Molecular & General Genetics. 168, 111 (1979).

Yeast can be transformed, for example, by the method described in Methods in Enzymology, 194, 182–187 (1991), Proc. Natl. Acad. Sci. U.S.A., 75, 1929 (1978), etc.

Insect cells or insects can be transformed, for example, according to the method described in Bio/Technology, 6, 47–55 (1988), etc.

Animal cells can be transformed, for example, according to the method described in Saibo Kogaku (Cell Engineering), extra issue 8, Shin Saibo Kogaku Jikken Protocol (New Cell Engineering Experimental Protocol), 263–267 (1995), published by Shujunsha, or Virology, 52, 456 (1973).

Thus, the transformant transformed with the expression vector comprising the DNA encoding FPRL1 or FPRL2 can be obtained.

Where the host is bacteria belonging to the genus *Escherichia* or the genus *Bacillus*, the transformant can be appropriately incubated in a liquid medium which contains materials required for growth of the transformant such as carbon sources, nitrogen sources, inorganic materials, and so on. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the inorganic materials are calcium chloride, sodium dihydrogenphosphate, magnesium chloride, etc. In addition, yeast extract, vitamins, growth promoting factors etc. may also be added to the medium. Preferably, pH of the medium is adjusted to about 5 to about 8.

A preferred example of the medium for incubation of the bacteria belonging to the genus *Escherichia* is M9 medium supplemented with glucose and Casamino acids (Miller, Journal of Experiments in Molecular Genetics, 431–433, Cold Spring Harbor Laboratory, New York, 1972). If necessary and desired, a chemical such as 3β-indolylacrylic acid can be added to the medium to activate the promoter efficiently.

Where the bacteria belonging to the genus *Escherichia* are used as the host, the transformant is usually cultivated at about 15° C. to about 43° C. for about 3 hours to about 24 hours. If necessary and desired, the culture may be aerated or agitated.

Where the bacteria belonging to the genus *Bacillus* are used as the host, the transformant is cultivated generally at about 30° C. to about 40° C. for about 6 hours to about 24 hours. If necessary and desired, the culture can be aerated or agitated.

Where yeast is used as the host, the transformant is cultivated, for example, in Burkholder's minimal medium (Bostian, K. L. et al., Proc. Natl. Acad. Sci. U.S.A., 77, 4505 (1980)) or in SD medium supplemented with 0.5% Casamino acids (Bitter, G. A. et al., Proc. Natl. Acad. Sci. U.S.A. 81, 5330 (1984)). Preferably, pH of the medium is adjusted to about 5 to about 8. In general, the transformant is cultivated at about 20° C. to about 35° C. for about 24 hours to about 72 hours. If necessary and desired, the culture can be aerated or agitated.

Where insect cells or insects are used as the host, the transformant is cultivated in, for example, Grace's Insect Medium (Grace, T. C. C., Nature, 195, 788 (1962)) to which an appropriate additive such as inactivated 10% bovine serum is added. Preferably, pH of the medium is adjusted to about 6.2 to about 6.4. Normally, the transformant is cultivated at about 27° C. for about 3 days to about 5 days and, if necessary and desired, the culture can be aerated or agitated.

Where animal cells are employed as the host, the transformant is cultivated in, for example, MEM medium containing about 5% to about 20% fetal bovine serum (Science, 122, 501(1952)), DMEM medium (Virology, 8, 396 (1959)), RPMI 1640 medium (The Journal of the American Medical Association, 199, 519 (1967)), 199 medium (Proceeding of the Society for the Biological Medicine, 73, 1(1950)), etc. Preferably, pH of the medium is adjusted to about 6 to about 8. The transformant is usually cultivated at about 30° C. to about 40° C. for about 15 hours to about 60 hours and, if necessary and desired, the culture can be aerated or agitated.

As described above, FPRL1 or FPRL2 of the present invention can be produced in the cell, in the cell membrane or out of the cell of the transformant.

FPRL1 or FPRL2 of the present invention can be separated and purified from the culture described above by the following procedures.

When FPRL1 or FPRL2 of the present invention is extracted from the culture or cells after cultivation, the transformants or cells are collected by a publicly known method and suspended in an appropriate buffer. The transformants or cells are then disrupted by publicly known methods such as ultrasonication, treatment with lysozyme and/or freeze-thaw cycling, followed by centrifugation, filtration, etc. Thus, the crude extract of FPRL1 or FPRL2 of the present invention can be obtained. The buffer used for the procedures may contain a protein modifier such as urea or guanidine hydrochloride, or a surfactant such as Triton X-100™, etc. When FPRL1 or FPRL2 is secreted in the culture, the supernatant after completion of the cultivation can be separated from the transformants or cells to collect the supernatant by a publicly known method.

FPRL1 or FPRL2 contained in the supernatant or the extract thus obtained can be purified by appropriately combining the publicly known methods for separation and purification. Such publicly known methods for separation and purification include a method utilizing difference in solubility such as salting out, solvent precipitation, etc.; a method utilizing mainly difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

When FPRL1 or FPRL2 thus obtained is in a free form, it can be converted into the salt by publicly known methods or modifications thereof. On the other hand, when FPRL1 or FPRL2 is obtained in the form of a salt, it can be converted into the free form or in the form of a different salt by publicly known methods or modifications thereof.

FPRL1 or FPRL2 produced by the recombinant can be treated, prior to or after the purification, with an appropriate protein modifying enzyme so that FPRL1 or FPRL2 can be appropriately modified to partially remove a polypeptide. Examples of the protein-modifying enzyme include trypsin, chymotrypsin, arginyl endopeptidase, protein kinase, glycosidase or the like.

The activity of the thus produced FPRL1 or FPRL2 of the present invention or salts thereof can be determined by a test binding to a labeled ligand (humanin), by an enzyme immunoassay using a specific antibody, or the like.

Antibodies to FPRL1 or FPRL2 of the present invention may be any of polyclonal antibodies and monoclonal antibodies as long as they are capable of recognizing FPRL1 or FPRL2 of the present invention.

The antibodies to FPRL1 or FPRL2 of the present invention may be manufactured by publicly known methods for manufacturing antibodies or antisera, using as antigens FPRL1 or FPRL2 of the present invention.

[Preparation of Monoclonal Antibody]

(a) Preparation of Monoclonal Antibody-Producing Cells

FPRL1 or FPRL2 of the present invention is administered to mammals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once in every two to six weeks and 2 to 10 times in total. Examples of the mammals used are monkeys, rabbits, dogs, guinea pigs, mice, rats, sheep and goats, with mice and rats being preferred.

In the preparation of monoclonal antibody-producing cells, warm-blooded animals, e.g., mice, immunized with an antigen wherein the antibody titer is noted are selected, then the spleen or lymph node is collected after 2 to 5 days from the final immunization and antibody-producing cells contained therein are fused with myeloma cells from an animal of the same or different species to give monoclonal antibody-producing hybridomas. Measurement of the antibody titer in antisera may be made, for example, by reacting a labeled form of the receptor protein, which will be described later, with the antiserum followed by assaying the binding activity of the labeling agent bound to the antibody. The fusion may be operated, for example, by the known Koehler and Milstein method (Nature, 256, 495, 1975). Examples of the fusion accelerator are polyethylene glycol (PEG), Sendai virus, etc., among which PEG is preferably employed.

Examples of the myeloma cells used include NS-1, P3U1, SP2/0 etc., among which P3U1 is particularly preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by incubation at about 20 to about 40° C., preferably at about 30 to about 37° C. for about 1 to about 10 minutes, efficient cell fusion can be carried out.

Various methods can be used for screening of a monoclonal antibody-producing hybridoma. Examples of such methods include a method which comprises adding the supernatant of hybridoma to a solid phase (e.g., microplate) adsorbed with the receptor protein as an antigen directly or together with a carrier, adding an anti-immunoglobulin antibody (when mouse cells are used for the cell fusion, anti-mouse immunoglobulin antibody is used) labeled with a radioactive substance or an enzyme, or Protein A and detecting the monoclonal antibody bound to the solid phase, and a method which comprises adding the supernatant of hybridoma to a solid phase adsorbed with an anti-immunoglobulin antibody or Protein A, adding the receptor protein labeled with a radioactive substance or an enzyme and detecting the monoclonal antibody bound to the solid phase.

The monoclonal antibody can be selected by publicly known methods or by modifications of these methods. In general, the selection can be effected in a medium for animal cells supplemented with HAT (hypoxanthine, aminopterin and thymidine). Any selection and growth medium can be employed as far as the hybridoma can grow therein. For example, RPMI 1640 medium containing 1% to 20%, preferably 10% to 20% fetal bovine serum, GIT medium (Wako Pure Chemical Industries, Ltd.) containing 1% to 10% fetal bovine serum, a serum-free medium for cultivation of a hybridoma (SFM-101, Nissui Seiyaku Co., Ltd.) and the like can be used for the selection and growth medium. The cultivation is carried out generally at 20° C. to 40° C., preferably at about 37° C., for 5 days to 3 weeks, preferably 1 to 2 weeks. The cultivation can be conducted normally in 5% $CO_2$. The antibody titer of the culture supernatant of hybridomas can be determined as in the assay for the antibody titer in antisera described above.

(b) Purification of Monoclonal Antibody

Separation and purification of a monoclonal antibody can be carried out by methods applied to conventional separation and purification of immunoglobulins, as in the conventional methods for separation and purification of polyclonal antibodies [e.g., salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A, Protein G. etc. and dissociating the binding to obtain the antibody].

[Preparation of Polyclonal Antibody]

The polyclonal antibody of the present invention can be manufactured by publicly known methods or modifications thereof. For example, an immunogen (antigen such as FPRL1 or FPRL2) itself or a complex prepared from the immunogen and a carrier protein is used to immunize a mammal in a manner similar to the method described above for the manufacture of monoclonal antibodies. The product containing the antibody to FPRL1 or FPRL2 of the present invention is collected from the immunized animal followed by separation and purification of the antibody.

In the complex of an immunogen and a carrier protein used to immunize a mammal, the type of carrier protein and the mixing ratio of a carrier to hapten may be any type and in any ratio, as long as the antibody is efficiently produced against the hapten immunized by crosslinking to the carrier. For example, bovine serum albumin, bovine thyroglobulins, keyhole limpet hemocyanin or the like is coupled to hapten in a carrier-to-hapten weight ratio of approximately 0.1 to 20, preferably about 1 to about 5.

A variety of condensing agents can be used for the coupling of a carrier to hapten. Glutaraldehyde, carbodiimide, maleimide-activated ester, activated ester reagents containing thiol group or dithiopyridyl group, etc. are used for the coupling.

The condensation product is administered to warm-blooded animals either solely or together with carriers or diluents to the site in which the antibody can be produce by the administration. In order to potentiate the antibody productivity upon the administration, complete Freund's adjuvant or incomplete Freund's adjuvant may be administered. The administration is usually made once approximately in every 2 to 6 weeks and about 3 to about 10 times in total.

The polyclonal antibody can be collected from the blood, ascites, etc., preferably from the blood of mammals immunized by the method described above.

The polyclonal antibody titer in antiserum can be assayed by the same procedure as that for the determination of serum antibody titer described above. The separation and purification of the polyclonal antibody can be carried out according to the method for the separation and purification of immunoglobulins performed as applied to the separation and purification of monoclonal antibodies described hereinabove.

The ligand to FPRL1 or FPRL2 of the present invention is humanin or its salt.

As humanin, (1) a polypeptide comprising the same or substantially the same amino acid sequence as the amino acid sequence represented by SEQ ID NO: 3 or (2) a polypeptide comprising the same or substantially the same amino acid sequence as the amino acid sequence represented by SEQ ID NO: 7 is used.

Humanin may be any polypeptide derived from any cells (e.g., liver cells, splenocytes, nerve cells, glial cells, β cells of pancreas, bone marrow cells, mesangial cells, Langerhans' cells, epidermic cells, epithelial cells, endothelial cells, fibroblasts, fibrocytes, myocytes, fat cells, immune cells (e.g., macrophage, T cells, B cells, natural killer cells, mast cells, neutrophil, basophil, eosinophil, monocyte), megakaryocyte, synovial cells, chondrocytes, bone cells, osteoblasts, osteoclasts, mammary gland cells or interstitial cells, the corresponding precursor cells, stem cells, cancer cells, etc.), or any tissues where such cells are present, e.g., brain or any region of the brain (e.g., olfactory bulb, amygdaloid nucleus, basal ganglia, hippocampus, thalamus, hypothalamus, cerebral cortex, medulla oblongata and cerebellum), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, cartilage, joint, skeletal muscle, etc. from human and non-human mammals (e.g., guinea pigs, rats, mice, chickens, rabbits, swine, sheep, bovine, monkeys, etc.). Humanin may also be a synthetic polypeptide.

The term "substantially equivalent" means that the polypeptide referred to is substantially equivalent in respect of the activities of humanin, for example physiological properties such as apotosis inhibitory action (for example, inhibitory action on apotosis accompanying various diseases) and cellular viability maintaining action, or prophylactic/therapeutic activity (action) on nerve degeneration diseases, cancers, immune disorders, infection diseases, alimentary diseases, circulatory diseases, endocrine diseases etc. Insofar as the substitution, deletion, addition or insertion of amino acids does not bring about a significant change in the physiological properties or chemical properties of the polypeptide, the polypeptide subjected to such substitution, deletion, addition or insertion is substantially the same as the peptide not having such substitution, deletion, addition or insertion. Substantially equivalent substituting amino acids in the amino acid sequence can be selected from amino acids in the class to which the amino acids to be substituted belong.

Nonpolar (hydrophobic) amino acids include alanine, leucine, isoleucine, valine, proline, phenylalanine, tryptophan, methionine etc. Polar (neutral) amino acids include glycine, serine, threonine, cysteine, tyrosine, asparagine, glutamine etc. Positively charged (basic) amino acids include arginine, lysine, histidine etc. Negatively charged (acidic) amino acids include aspartic acid, glutamic acid etc.

The amino acid sequence having substantially the same amino acid sequence as the amino acid sequence represented by SEQ ID NO: 3 is not particularly limited insofar as a polypeptide having the amino acid sequence has the activity (property) substantially equivalent to that of humanin consisting of the amino acid sequence represented by SEQ ID NO: 3, and examples of the above amino acid sequence include an amino acid sequence having at least about 60% homology, preferably at least about 80% homology, more preferably at least about 85% homology, still more preferably at least about 90% homology, most preferably at least about 95% homology, to the amino acid sequence represented by SEQ ID NO: 3.

The amino acid sequence having substantially the same amino acid sequence as the amino acid sequence represented by SEQ ID NO: 7 is not particularly limited insofar as a polypeptide having the amino acid sequence has a substantially equivalent activity (property) to that of humanin consisting of the amino acid sequence represented by SEQ ID NO: 7, and examples of the above amino acid sequence include an amino acid sequence having at least about 60% homology, preferably at least about 80% homology, more preferably at least about 85% homology, still more preferably at least about 90% homology, most preferably at least about 95% homology, to the amino acid sequence represented by SEQ ID NO: 7.

The homology among the amino acid sequences can be calculated using homology calculation algorism NCBI BLAST (National Center for Biotechnology Information Basic Local Alignment Search Tool) under the following conditions: expected value=10; gap is allowable; matrix=BLOSUM62; filtering=OFF.

The substantially equivalent activity (property) means that the polypeptide referred to is qualitatively equivalent to humanin comprising the amino acid sequence represented by, for example, SEQ ID NO: 3 or SEQ ID NO: 4 in respect of physiological properties such as apotosis inhibitory action (for example, inhibitory action on apotosis accompanying various diseases) and cellular viability maintaining action, or prophylactic/therapeutic activity (action) on nerve degeneration diseases, cancers, immune disorders, infection diseases, alimentary diseases, circulatory diseases, endocrine diseases etc.

Specific examples of humanin comprising substantially the same amino acid sequence as the amino acid sequence represented by SEQ ID NO: 3 include a) amino acid sequences represented by SEQ ID NO: 3, SEQ ID NO: 4 or SEQ ID NO: 8, wherein 1 or more amino acids (for example approximately 1 to 10 amino acids, preferably approximately 1 to 6 amino acids, more preferably approximately 1 to 3 amino acids, still more preferably 1 or 2 amino acids) are deleted, b) amino acid sequences represented by SEQ ID NO: 3, SEQ ID NO: 4 or SEQ ID NO: 8 to which 1 or more amino acids (for example approximately 1 to 10 amino acids, preferably approximately 1 to 6 amino acids, more preferably approximately 1 to 3 amino acids, still more preferably 1 or 2 amino acids) are added, c) amino acid sequences represented by SEQ ID NO: 3, SEQ ID NO: 4 or SEQ ID NO: 8, wherein 1 or more amino acids (for example approximately 1 to 5 amino acids, preferably approximately 1 to 3 amino acids, more preferably 1 or 2 amino acids) are substituted by other amino acids, and d) polypeptides consisting of a combination of the amino acid sequences described in the above, but do not include a polypeptide consisting of the amino acid sequence represented by SEQ ID NO: 5 and a polypeptide consisting of an amino acid sequence in positions 1 to 21 in the amino acid sequence represented by SEQ ID NO: 5.

Specific examples of humanin comprising substantially the same amino acid sequence as the amino acid sequence represented by SEQ ID NO: 7 include a) an amino acid sequence represented by SEQ ID NO: 7, wherein 1 or more amino acids (for example approximately 1 to 10 amino acids, preferably approximately 1 to 6 amino acids, more preferably approximately 1 to 3 amino acids, still more preferably 1 or 2 amino acids) are deleted, b) an amino acid sequence represented by SEQ ID NO: 7 to which 1 or more amino acids (for example approximately 1 to 10 amino acids, preferably approximately 1 to 6 amino acids, more preferably approximately 1 to 3 amino acids, still more preferably 1 or 2 amino acids) are added, c) an amino acid sequence represented by SEQ ID NO: 7, wherein 1 or more amino acids (for example approximately 1 to 10 amino acids, preferably approximately 1 to 6 amino acids, more preferably approximately 1 to 3 amino acids, still more preferably 1 or 2 amino acids) are substituted by other amino acids, and d) polypeptides consisting of a combination of the amino acid sequences described in the above.

When the amino acid sequence has undergone insertion, deletion or substitution as described above, the position of the insertion, deletion or substitution is not particularly limited.

Specific examples of humanin include:
(1) human humanin (1-24) consisting of the amino acid sequence represented by SEQ ID NO: 3,
(2) [Gly$^{14}$]-humanin (1-24) consisting of the amino acid sequence represented by SEQ ID NO: 4,
(3) human humanin (1-21) consisting of the amino acid sequence represented by SEQ ID NO: 6,
(4) rat human humanin (1-38) consisting of the amino acid sequence represented by SEQ ID NO: 7,
(5) rat humanin (1-24) consisting of the amino acid sequence represented by SEQ ID NO: 8, and
(6) rat humanin (1-21) consisting of the amino acid sequence represented by SEQ ID NO: 9.

Humanin may be a partial peptide of the polypeptide described above. As the partial peptide of humanin, any partial peptide described above can be used so long as it is a partial peptide of humanin described above, and for example, a partial peptide having the activity substantially equivalent to that of humanin ("activity substantially equivalent" has the same meaning as defined above) is preferably used.

Specifically, the partial peptide of humanin is a partial peptide of a polypeptide comprising the same or substantially the same amino acid sequence as the amino acid sequence represented by SEQ ID NO: 3 or SEQ ID NO: 7, preferably a partial peptide comprising a sequence of consecutive approximately 6 to 20 amino acids, preferably approximately 6 to 15 amino acids, more preferably approximately 6 to 10 amino acids, in the same or substantially the same amino acid sequence as the amino acid sequence represented by SEQ ID NO: 3.

The "substantially the same" has the same meaning as described above in humanin.

More specific examples of the partial peptide of humanin include a) a peptide comprising an amino acid sequence of approximately 6 to 20 amino acids, preferably approximately 6 to 15 amino acids, more preferably approximately 6 to 10 amino acids, in the amino acid sequence represented by SEQ ID NO: 3, SEQ ID NO: 4 or SEQ ID NO: 8, b) amino acid sequences comprising the above amino acid sequence wherein 1 or more amino acids (for example, approximately 1 to 6 amino acids, preferably approximately 1 to 3 amino acids, more preferably 1 or 2 amino acids) are deleted, c) amino acid sequences comprising the above amino acid sequence to which 1 or more amino acids (for example, approximately 1 to 6 amino acids, preferably approximately 1 to 3 amino acids, more preferably 1 or 2 amino acids) are added, d) amino acid sequences comprising the above amino acid sequence wherein 1 or more amino acids (for example, approximately 1 to 6 amino acids, preferably approximately 1 to 3 amino acids, more preferably 1 or 2 amino acids) are substituted by other amino acids, and e) partial peptides consisting of the above sequences with a combination of deletion, addition and substitution, among which use is made of a peptide consisting of an amino acid sequence of approximately 6 to 20 amino acids, preferably approximately 6 to 15 amino acids, still more preferably approximately 6 to 10 amino acids, from the N-terminus of the amino acid sequence represented by SEQ ID NO: 3, SEQ ID NO: 4 or SEQ ID NO: 8.

When the amino acid sequence has undergone insertion, deletion or substitution as described above, the position of the insertion, deletion or substitution is not particularly limited. However, the above substitution does not include the substitution of amino acid at position 3, 12, 14, 15, 16 or 24 in the amino acid sequence represented by SEQ ID NO: 3 or SEQ ID NO: 4.

Specific examples of the partial peptide of humanin include, for example, partial peptides consisting of the following amino acid sequences a) to d) respectively wherein the number of amino acids is approximately 6 to 20, preferably approximately 6 to 15, more preferably approximately 6 to 10: a) an amino acid sequence in positions 19 to 24, positions 5 to 24, positions 1 to 20, positions 5 to 20 or positions 5 to 21 in the amino acid sequence represented by SEQ ID NO: 3, SEQ ID NO: 4 or SEQ ID NO: 8, b) an amino acid sequence comprising the above amino acid sequence wherein 1 or more amino acids (for example, about 1 to 6 amino acids, preferably about 1 to 3 amino acids, more preferably 1 to 2 amino acids) are deleted, c) an amino acid sequence comprising the above amino acid sequence wherein 1 or more amino acids (for example, about 1 to 6 amino acids, preferably about 1 to 3 amino acids, more preferably 1 to 2 amino acids) are added, d) an amino acid sequence comprising the above amino acid sequence wherein 1 or more amino acids (for example, about 1 to 6 amino acids, preferably about 1 to 3 amino acids, more preferably 1 to 2 amino acids) are substituted by other amino acids, and e) an amino acid sequence comprising the above amino acid sequence with a combination of deletion, addition and substitution mentioned above. However, the above substitution does not include the substitution of amino acid at position 3, 12, 14, 15, 16 or 24 in the amino acid sequence represented by SEQ ID NO: 3 or SEQ ID NO: 4.

The partial peptide of humanin does not include a peptide consisting of an amino acid sequence in positions 19 to 24, positions 5 to 24, positions 1 to 20, positions 5 to 20 or positions 5 to 21 in the amino acid sequence represented by SEQ ID NO: 5.

More preferable examples of the partial peptide of humanin include a peptide consisting of an amino acid sequence in positions 19 to 24, positions 5 to 24, positions 1 to 20, positions 5 to 20 or positions 5 to 21 in the amino acid sequence represented by SEQ ID NO: 3, SEQ ID NO: 4 or SEQ ID NO: 8.

Humanin or its partial peptides include those wherein a substituent on the side chain of an amino acid in the molecule is protected with a suitable protecting group, or conjugated proteins such as glycoproteins bound to sugar chains.

Humanin may occur not only as a monomer but also as a dimer, trimer, tetramer etc., and specifically there are cases where humanin molecules form a dimer, the partial peptides of the present invention form a dimer, and humanin and the partial peptide of the present invention form a dimer.

Humanin and its partial peptides (hereinafter referred to collectively as humanin) include those wherein an arbitrary extraneous peptide sequence (for example, FLAG, His tag, HA tag, HSV tag etc.) capable of serving as an epitope (antibody recognition site) is added to the N- or C-terminus thereof.

Humanin is represented in accordance with the conventional way of describing peptides, that is, the N-terminus (amino terminus) at the left hand and the C-terminus (carboxyl terminus) at the right hand. In humanin including the polypeptide comprising the amino acid sequence represented by SEQ ID NO: 3 or 4, the C-terminus is usually in the form of a carboxyl group (—COOH) or a carboxylate (—COO⁻) but may be in the form of an amide (—CONH$_2$) or an ester (—COOR), particularly preferably an amide (—CONH$_2$).

The ester group shown by R include, for example, a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl group such as a phenyl-$C_{1-2}$-alkyl group, e.g., benzyl, phenethyl, etc., or an α-naphthyl-$C_{1-2}$-alkyl group such as α-naphthylmethyl, etc. In addition, a pivaloyloxymethyl group or the like which is used widely as an ester for oral administration may also be used.

Where humanin has a carboxyl group (or a carboxylate) at a position other than the C-terminus, it may be amidated or esterified, and such an amide or ester is also included within humanin in the present specification. As the ester group herein, the same esters as those described with respect to the above C-terminal are used.

Furthermore, examples of humanin include variants of the above proteins, wherein the N-terminal amino group residue (e.g. methionine residue) thereof is protected with a protecting group (for example, a $C_{1-6}$ acyl group such as a $C_{1-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{1-6}$ alkanoyl group, e.g., formyl group, acetyl group, etc.), or conjugated proteins such as glycoproteins having sugar chains bound thereto.

Humanin is preferably a polypeptide wherein the amino group of N-terminal amino acid residue thereof is formylated, particularly preferably a polypeptide having a methionine residue at the N-terminus thereof wherein the amino group of the N-terminal methionine residue is formylated.

Specifically, polypeptides consisting of amino acid sequences having an N-terminal methionine residue whose amino group is formylated, which are represented by SEQ ID NO: 3, SEQ ID NO: 4, SEQ ID NO: 6, SEQ ID NO: 7, SEQ ID NO: 8 or SEQ ID NO: 9, are preferably used.

As salts of humanin, use is made of salts with physiologically acceptable acids (e.g., inorganic acids or organic acids) or bases (e.g., alkali metal salts), preferably physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

Hereinafter, humanin or salts thereof are referred to collectively as humanin.

Humanin may be manufactured from the human and other warm-blooded animal cells or tissues described above by a publicly known protein purification method, or may also be manufactured by the peptide synthesis method, which will be described below.

When humanin is manufactured from human and non-human mammalian tissues or cells, the human or non-human mammalian tissues or cells are homogenized, then extracted with an acid or the like, and the extract is isolated and purified by a combination of chromatography techniques such as reverse phase chromatography, ion exchange chromatography, and the like.

To synthesize humanin or amides thereof, commercially available resins that are used for polypeptide synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenylhydroxymethyl)phenoxy resin, 4-(2',4'-dimethoxyphenyl-Fmoc-aminoethyl) phenoxy resin, etc. Using these resins, amino acids in which α-amino groups and functional groups on the side chains are appropriately protected are condensed on the resin in the order of the sequence of the objective protein according to various condensation methods publicly known in the art. At the end of the reaction, the protein is cut out from the resin and at the same time, the protecting groups are removed. Then, intramolecular disulfide bond-forming reaction is performed in a highly diluted solution to obtain the objective polypeptide or its amides.

For condensation of the protected amino acids described above, a variety of activation reagents for polypeptide synthesis may be used, and carbodiimides are particularly preferable. Examples of such carbodiimides include DCC, N,N'-diisopropylcarbodiimide, N-ethyl-N'-(3-dimethylaminopropyl)carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be chosen from solvents known to be usable for polypeptide condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to polypeptide binding reactions and is usually selected in the range of approximately −20° C. to 50° C. The activated amino acid derivatives are used generally in an excess of 1.5 to 4 times. The condensation is examined by a test using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole to cancel any possible adverse effect on the subsequent reaction.

Examples of the protecting groups used to protect the amino groups of the starting compounds include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower ($C_{1-6}$) alkanoyl group, such as acetyl group, an aroyl group such as benzoyl group, and a group derived from carbonic acid, such as benzyloxycarbonyl group, ethoxycarbonyl group, etc. Examples of a group appropriately used for the etherification include benzyl group, tetrahydropyranyl group, t-butyl group, etc.

Examples of groups for protecting the phenolic hydroxyl group of tyrosine include Bzl, $C_{12}$-Bzl, 2-nitrobenzyl, Br-Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting compounds include the corresponding acid anhydrides, azides, activated esters (esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)). As the activated amino acids in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; acid treatment with anhydrous hydrogen fluoride, methanesulfonic acid, trifluoromethanesulfonic acid or trifluoroacetic acid, or a mixture solution of these acids; treatment with a base such as diisopropylethylamine, triethylamine, piperidine or piperazine; and reduction with sodium in liquid ammonia. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol or 1,2-ethanedithiol. Furthermore, 2,4-dinitrophenyl group used as the protecting group for the imidazole of histidine is removed by treatment with thiophenol. Formyl group used as the protecting group of the indole of tryptophan is eliminated by the aforesaid acid treatment in the presence of 1,2-ethanedithiol or 1,4-butanedithiol, as well as by treatment with an alkali such as a dilute sodium hydroxide solution and dilute ammonia.

Protection of functional groups that should not be involved in the reaction of the starting materials, protecting groups, elimination of the protecting groups and activation of functional groups involved in the reaction may be appropriately selected from publicly known groups and publicly known means.

In an alternative method for obtaining the amides of humanin, for example, the α-carboxyl group of the carboxy terminal amino acid is first protected by amidation, and the peptide (polypeptide) chain is then extended from the amino group side to a desired length. Thereafter, a polypeptide in which only the protecting group of the N-terminal α-amino group in the peptide chain has been eliminated from the polypeptide and a polypeptide in which only the protecting group of the C-terminal carboxyl group has been eliminated are prepared. The two polypeptide are condensed in a mixture of the solvents described above. The details of the condensation reaction are the same as described above. After the protected polypeptide obtained by the condensation is purified, all the protecting groups are eliminated by the method described above to give the desired crude polypeptide. This crude polypeptide is purified by various known purification means. Lyophilization of the major fraction gives the amide of desired humanin.

To prepare esterified humanin, for example, the α-carboxyl group of the carboxy terminal amino acid is condensed with a desired alcohol to prepare the amino acid ester, which is followed by procedure similar to the preparation of the amidated humanin above to give the ester form of the desired polypeptide.

Alternatively, humanin can be manufactured by publicly known methods for peptide synthesis. For the methods for peptide synthesis, for example, either solid phase synthesis or liquid phase synthesis may be used. That is, the partial peptide or amino acids that can construct humanin are condensed with the remaining part. Where the product contains protecting groups, these protecting groups are removed to give the desired peptide. Publicly known methods for condensation and elimination of the protecting groups are described in (1) to (5) below.

(1) M. Bodanszky & M. A. Ondetti: Peptide Synthesis, Interscience Publishers, New York (1966)
(2) Schroeder & Luebke: The Peptide, Academic Press, New York (1965)
(3) Nobuo Izumiya, et al.: Peptide Gosei-no-Kiso to Jikken (Basics and experiments of peptide synthesis), published by Maruzen Co. (1975)
(4) Haruaki Yajima & Shunpei Sakakibara: Seikagaku Jikken Koza (Biochemical Experiment) 1, Tanpakushitsu no Kagaku (Chemistry of Proteins) IV, 205 (1977)
(5) Haruaki Yajima, ed.: Zoku Iyakuhin no Kaihatsu (A sequel to Development of Pharmaceuticals), Vol. 14, Peptide Synthesis, published by Hirokawa Shoten After completion of the reaction, the product may be isolated and purified by a combination of conventional purification methods such as solvent extraction, distillation, column chromatography, liquid chromatography and recrystallization to give the partial peptide of the present invention. When the polypeptide obtained by the above methods is in a free form, the polypeptide can be converted into an appropriate salt by a publicly known method or a modification thereof; when the partial peptide is obtained in a salt form, it can be converted into a free form or another salt by a publicly known method or a modification thereof.

Humanin possesses an apoptosis inhibitory action, a cellular viability maintaining action etc., and thus the humanin receptor FPRL1 or FPRL2 of the present invention, the DNA encoding FPRL1 or FPRL2 (hereinafter sometimes referred to as the DNA of the present invention), the antibody to FPRL1 or FPRL2 (hereinafter sometimes referred to as the antibody of the present invention), the antisense DNA to the DNA of the present invention (hereinafter sometimes referred to as the antisense DNA of the present invention) have the following uses.

(1) Prophylactic and/Therapeutic Agent for Diseases Associated with Dysfunction of FPRL1 or FPRL2 of the Present Invention Humanin is known to occur in the living body and have an apoptosis inhibitory action, a cellular viability maintaining action etc. Therefore, where FPRL1 or FPRL2 of the present invention or the polynucleotide (for example, DNA etc.) encoding the same is abnormal or deficient, or where the expression level of FPRL1 or FPRL2 of the present invention is abnormally reduced or promoted, there occur a variety of diseases involving nerve degeneration, for example, nerve degeneration diseases (for example, Alzheimer's disease [familial Alzheimer's disease, early-onset Alzheimer's disease, sporadic Alzheimer's disease etc.], Parkinson's disease, Down's syndrome, amyotrophic lateral sclerosis, prion disease, Creutzfeldt-Jakob disease, Huntington's disease, diabetic neuropathy, multiple sclerosis etc.), brain function disorders (for example, cerebral infarction, cerebral hemorrhage, subarachnoid hemorrhage, ischemic cerebral disease, epidural hematoma, subdural hematoma etc.), cancers (for example, astrocytoma, oligodendrocytoma etc.), immune diseases, infection diseases (for example, meningitis, protozoan infection, rickettia infection, protozoa metazoan infection, bacterial or viral meningitis such as Boma disease, encephalitis after vaccine inoculation, dementia associated with AIDS, etc.), alimentary diseases, circulatory diseases, endocrine diseases etc.

Accordingly, when the physiological activity of the ligand humanin cannot be expected in a patient (deficiency of FPRL1 or FPRL2) due to a decrease in FPRL1 or FPRL2 of the present invention, the activity of the ligand can be exhibited by (i) administering FPRL1 or FPRL2 of the present invention to the patient thereby supplementing the amount of the FPRL1 or FPRL2 or (ii) by increasing the amount of FPRL1 or FPRL2 in the patient through i) administration of the DNA encoding FPRL1 or FPRL2 of the present invention to express the same in the patient or ii) insertion and expression of the DNA encoding FPRL1 or FPRL2 of the present invention in the objective cells to transplant the cells to the patient, whereby the activity of the ligand can be sufficiently exhibited.

Accordingly, a) FPRL1 or FPRL2 of the present invention or b) the DNA encoding FPRL1 or FPRL2 is useful as a safe and low toxic prophylactic/therapeutic agent for diseases associated with dysfunction of FPRL1 of the present invention.

Specifically, FPRL1 or FPRL2 of the present invention or the DNA of the present invention can be used for example as an apotosis inhibitor and as a low toxic and safe pharmaceutical preparation such as a prophylactic/therapeutic agent for diseases involving nerve degeneration, for example, nerve degeneration diseases (for example, Alzheimer's disease [familial Alzheimer's disease, early-onset Alzheimer's disease, sporadic Alzheimer's disease etc.], Parkinson's disease, Down's syndrome, amyotrophic lateral sclerosis, prion disease, Creutzfeldt-Jakob disease, Huntington's disease, diabetic neuropathy, multiple sclerosis etc.), brain function disorders (for example, cerebral infarction, cerebral hemorrhage, subarachnoid hemorrhage, ischemic cerebral disease, epidural hematoma, subdural hematoma etc.), cancers (for example, astrocytoma, oligodendrocytoma etc.), immune diseases, infection diseases (for example, meningitis, protozoan infection, rickettia infection, protozoa metazoan infection, bacterial or viral meningitis such as Borna disease, encephalitis after vaccine inoculation, dementia associated with AIDS, etc.), alimentary diseases, circulatory diseases, endocrine diseases etc., preferably as a prophylactic/therapeutic agent for nerve degeneration diseases and brain function disorders, more preferably as a prophylactic/therapeutic agent for Alzheimer's disease.

When FPRL1 or FPRL2 of the present invention is used as the prophylactic/therapeutic agents supra, FPRL1 or FPRL2 can be prepared into a pharmaceutical composition in a conventional manner.

On the other hand, where the DNA of the present invention is used as the prophylactic/therapeutic agents described above, the DNA itself is administered; alternatively, the DNA is inserted into an appropriate vector such as retrovirus vector, adenovirus vector, adenovirus-associated virus vector, etc. and then administered in a conventional manner. The DNA of the present invention may also be administered as naked DNA, or with adjuvants to assist its uptake by gene gun or through a catheter such as a catheter with a hydrogel.

For example, a) FPRL1. or FPRL2 of the present invention or b) DNA of the present invention can be used orally in the form of tablets which may be sugar coated if necessary and desired, capsules, elixirs, microcapsules etc., or parenterally in the form of injectable preparations such as a sterile solution and a suspension in water or with other pharmaceutically acceptable liquid. These preparations can be manufactured for example by mixing a) FPRL1 or FPRL2 of the present invention or b) DNA of the present invention with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin, alginic acid, etc., a lubricant such as magnesium stearate, a sweetening agent such as sucrose, lactose or saccharin, and a flavoring agent such as peppermint, akamono oil or cherry. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredient in a vehicle such as water for injection, with a naturally occurring vegetable oil such as sesame oil, coconut oil, etc. to prepare the pharmaceutical composition. Examples of an aqueous medium for injection include physiological saline and an isotonic solution containing glucose and other auxiliary agents (e.g., D-sorbitol, D-mannitol, sodium chloride, etc.) and may be used in combination with an appropriate solubilizer such as an alcohol (e.g., ethanol or the like), a polyalcohol (e.g., propylene glycol and polyethylene glycol), a nonionic surfactant (e.g., polysorbate 80™ and HCO-50), etc. Examples of the oily medium include sesame oil, soybean oil, etc., which may also be used in combination with a solubilizer such as benzyl benzoate, benzyl alcohol, etc.

The prophylactic/therapeutic agent may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

The thus obtained pharmaceutical preparation is safe and low toxic, and can thus be administered to, for example, humans and mammals (e.g., rat, mouse, rabbit, sheep, swine, bovine, cat, dog, monkey etc.).

The dose of FPRL1 or FPRL2 of the present invention may vary depending on subject to be administered, target organ, symptom, administration method, etc. When the protein is orally administered, the protein is administered to a patient with Alzheimer's disease (as 60 kg) generally in a daily dose of approximately 0.1 to 100 mg, preferably approximately 1.0 to 50 mg, more preferably approximately 1.0 to 20 mg. When the protein is parenterally administered, a single dose of the protein may vary depending on subject to be administered, target organ, symptom, administration method, etc. When the protein is administered in the form of an injection to a patient with Alzheimer's disease (as 60 kg), it is convenient to administer the protein by intravenous injection generally in a daily dose of approximately 0.01 to 30 mg, preferably approximately 0.1 to 20 mg, more preferably approximately 0.1 to 10 mg. For other animal species, the corresponding dose as converted per 60 kg weight can be administered.

The dose of the DNA of the present invention may vary depending on subject to be administered, target organ, symptom, administration method, etc. When the DNA is orally administered, the DNA is administered to a patient with Alzheimer's disease (as 60 kg) generally in a daily dose of approximately 0.1 to 100 mg, preferably approximately 1.0 to 50 mg, more preferably approximately 1.0 to 20 mg. When the DNA is parenterally administered, a single dose of the DNA may vary depending on subject to be administered, target organ, symptom, administration method, etc. When the DNA is administered in the form of an injection to a patient with Alzheimer's disease (as 60 kg), it is convenient to administer the protein by intravenous injection generally in a daily dose of approximately 0.01 to 30 mg, preferably approximately 0.1 to 20 mg, more preferably approximately 0.1 to 10 mg. For other animal species, the corresponding dose as converted per 60 kg weight can be administered.

(2) Gene Diagnostic Agent

By using the DNA or antisense DNA of the present invention as a probe, an abnormality (gene abnormality) of the DNA or mRNA encoding FPRL1 of the present invention or its partial peptide in humans or mammals (e.g., rat, mouse, rabbit, sheep, swine, bovine, cat, dog, monkey etc.) can be detected. Therefore, the DNA or antisense DNA of the present invention is useful as a gene diagnostic agent for detecting damages to the DNA or mRNA, its mutation, or decreased expression, increased expression, overexpression, etc. of the DNA or mRNA, and so on.

The gene diagnosis described above using the DNA or antisense DNA of the present invention can be performed by, for example, the publicly known Northern hybridization assay or the PCR-SSCP assay (Genomics, 5, 874–879 (1989); Proceedings of the National Academy of Sciences of the United States of America, 86, 2766–2770 (1989)), etc.

When decreased expression of FPRL1 or FPRL2 is detected, e.g., by the Northern hybridization or when DNA mutation is detected by the PCR-SSCP assay, it can be diagnosed that it is highly likely to suffer from diseases, for example, diseases involving nerve degeneration, for example, nerve degeneration diseases (for example, Alzheimer's disease [familial Alzheimer's disease, early-onset Alzheimer's disease, sporadic Alzheimer's disease etc.], Parkinson's disease, Down's syndrome, amyotrophic lateral sclerosis, prion disease, Creutzfeldt-Jakob disease, Huntington's disease, diabetic neuropathy, multiple sclerosis etc.), brain function disorders (for example, cerebral infarction, cerebral hemorrhage, subarachnoid hemorrhage, ischemic cerebral disease, epidural hematoma, subdural hematoma etc.), cancers (for example, astrocytoma, oligodendrocytoma etc.), immune diseases, infection diseases (for example, meningitis, protozoan infection, rickettia infection, protozoa metazoan infection, bacterial or viral meningitis such as Borna disease, encephalitis after vaccine inoculation, dementia associated with AIDS, etc.), alimentary diseases, circulatory diseases, endocrine diseases etc.

(3) Pharmaceutical Preparation Comprising a Compound or its Salt that Alters the Expression Amount of FPRL1 or FPRL2 of the Present Invention The DNA of the present invention can be used as a probe in screening of a compound or its salt that alters the expression amount of FPRL1 or FPRL2 of the present invention.

That is, the present invention provides, for example, a method of screening a compound or its salt that alters the expression amount of FPRL1 or FPRL2 of the present invention, which comprises measuring the amount of mRNA of FPRL1 or FPRL2 of the present invention in, for example, (i) a) blood, b) specific organs or c) tissues or cells isolated from organs in non-human mammals or (ii) transformants, etc.

Specifically, the amount of mRNA of FPRL1 or FPRL2 of the present invention is measured in the following manner.

(i) Normal or morbid non-human mammals (for example, mice, rats, rabbits, sheep, swine, bovine, cats, dogs, monkeys etc., specifically rats, mice, rabbits etc. with Alzheimer's disease) are given a chemical (for example, an immune regulator etc.) or physical stress (for example, water immersion stress, electrical shock, brightening/darkening, low temperature, etc.), and after a predetermined time, blood, a specific organ (for example, brain, liver, kidney, etc.) or tissues or cells isolated from organs are obtained.

The mRNA of FPRL1 or FPRL2 of the present invention contained in the resulting cells can be quantified by techniques such as, for example, TaQMan PCR of the mRNA extracted in a usual manner from the cells, and can be analyzed by Northern blotting by a means known per se.

(ii) The transformant expressing FPRL1 or FPRL2 of the present invention is prepared according to the method described above, and the mRNA of FPRL1 or FPRL2 of the present invention in the transformant can be quantified and analyzed in the same manner as described above.

Screening of the compound or its salt that alters the expression amount of FPRL1 or FPRL2 of the present invention can be carried out by:

(i) administering a test compound into normal or morbid non-human mammals before a predetermined time, that is, 30 minutes to 24 hours before, preferably 30 minutes to 12 hours before, more preferably 1 hour to 6 hours before giving chemical or physical stress to the mammals, or after a predetermined time, that is, 30 minutes to 3 days after, preferably 1 hour to 2 days after, more preferably 1 hour to 24 hours after giving chemical or physical stress, or simultaneously with the chemical or physical stress, and quantifying and analyzing the amount of mRNA of FPRL1 or FPRL2 of the present invention in the cells after a predetermined time, that is, 30 minutes to 3 days after, preferably 1 hour to 2 days after, more preferably 1 hour to 24 hours after the administration, or (ii) mixing a test compound with a medium for culturing the transformant in a usual manner and quantifying and analyzing the amount of mRNA of FPRL1 or FPRL2 of the present invention in the transformant after culture, that is, 1 to 7 days later, preferably 1 to 3 days later, more preferably 2 to 3 days later.

The test compound used includes, for example, peptides, proteins, non-peptide compounds, synthetic compounds, fermentation products, cell extracts, plant extracts, and animal tissue extracts. These compounds may be novel or known compounds.

The test compounds may form salts, and as salts of the test compounds, use is made of salts with physiologically acceptable acids (e.g., inorganic acids etc.) or bases (e.g., organic acids [sic] etc.), preferably physiologically acceptable acid addition salts. Examples of such salts are salts with inorganic acids (e.g., hydrochloric acid, phosphoric acid, hydrobromic acid, sulfuric acid etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid etc.) etc.

The compound or its salt obtained using the screening method of the present invention is a compound or its salt having an action of changing the expression level of FPRL1 or FPRL2 of the present invention, specifically (a) a compound or its salt that increases the expression level of FPRL1 or FPRL2 of the present invention thereby increasing the FPRL1- or FPRL2-mediated cell-stimulating activity or (b) a compound or its salt that reduces the expression level of FPRL1 or FPRL2 of the present invention thereby reducing the cell-stimulating activity.

The cell-stimulating activity includes, for example, activities that promote or suppress arachidonic acid release, acetylcholine release, intracellular $Ca^{2+}$ release, intracellular cAMP production, intracellular cGMP production, inositol phosphate production, changes in cell membrane potential, phosphorylation of intracellular proteins, activation of c-fos, pH reduction, etc., among which the activity that suppresses intracellular cAMP production is preferably used.

The compounds which are obtainable using the screening method include peptides, proteins, non-peptide compounds, synthetic compounds and fermentation products, and these compounds may be novel or known compounds.

As salts of the compounds obtainable using the screening method of the present invention, use is made of salts with physiologically acceptable acids (e.g., inorganic acids etc.) or bases (e.g., organic acids [sic] etc.), preferably physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid etc.) and the like.

The ligand of FPRL1 or FPRL2 of the present invention is humanin as described above. Accordingly, the compound or its salt obtained by the screening method described above is:

(1) a compound or its salt preventing/treating diseases associated with dysfunction of FPRL1 or FPRL2 of the present invention by increasing the expression level of FPRL1 or FPRL2 of the present invention, specifically a compound or its salt preventing/treating nerve degeneration diseases or brain functional disorders or a compound inhibiting apotosis, or (2) a compound or its salt preventing/treating diseases attributable to overexpression of FPRL1 or FPRL2 of the present invention by decreasing the expression level of FPRL1 or FPRL2 of the present invention.

Accordingly, the compound or its salt obtained by the screening method described above, which increases the expression level of FPRL1 or FPRL2 of the present invention, can be used for example as an apotosis inhibitor and as a low toxic and safe pharmaceutical preparation such as a prophylactic/therapeutic agent for diseases involving nerve degeneration, for example, nerve degeneration diseases (for example, Alzheimer's disease [familial Alzheimer's disease, early-onset Alzheimer's disease, sporadic Alzheimer's disease etc.], Parkinson's disease, Down's syndrome, amyotrophic lateral sclerosis, prion disease, Creutzfeldt-Jakob disease, Huntington's disease, diabetic neuropathy, multiple sclerosis etc.), brain function disorders (for example, cerebral infarction, cerebral hemorrhage, subarachnoid hemorrhage, ischemic cerebral disease, epidural hematoma, subdural hematoma etc.), cancers (for example, astrocytoma, oligodendrocytoma etc.), immune diseases, infection diseases (for example, meningitis, protozoan infection, rickettia infection, protozoa metazoan infection, bacterial or viral meningitis such as Boma disease, encephalitis after vaccine inoculation, dementia associated with AIDS, etc.), alimentary diseases, circulatory diseases, endocrine diseases etc., preferably as a prophylactic/therapeutic agent for nerve degeneration diseases and brain function disorders, more preferably as a prophylactic/therapeutic agent for Alzheimer's disease.

The compound or its salt that decreases the expression level of FPRL1 or FPRL2 of the present invention, which is obtained by the screening method described above, can be used as a pharmaceutical preparation such as a prophylactic/therapeutic agent for diseases associated with overexpression of FPRL1 or FPRL2 of the present invention.

When the compound or its salt obtainable by the screening method of the present invention is used in a pharmaceutical composition, the compound can be formulated by the conventional methods.

For example, the compound or its salt can be used orally, for example, in the form of tablets which may be sugar coated if necessary and desired, capsules, elixirs, microcapsules etc., or parenterally in the form of injectable preparations such as a sterile solution and a suspension in water or with other pharmaceutically acceptable liquid. These preparations can be manufactured for example by mixing the compound or its salt with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin, alginic acid, etc., a lubricant such as magnesium stearate, a sweetening agent such as sucrose, lactose or saccharin, and a flavoring agent such as peppermint, akamono oil or cherry. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil, coconut oil, etc. to prepare the pharmaceutical composition. Examples of an aqueous medium for injection include physiological saline and an isotonic solution containing glucose and other auxiliary agents (e.g., D-sorbitol, D-mannitol, sodium chloride, etc.) and may be used in combination with an appropriate solubilizer such as an alcohol (e.g., ethanol or the like), a polyalcohol (e.g., propylene glycol and polyethylene glycol), a nonionic surfactant (e.g., polysorbate 80™ and HCO-50), etc. Examples of the oily medium include sesame oil, soybean oil, etc., which may also be used in combination with a solubilizer such as benzyl benzoate, benzyl alcohol, etc.

The prophylactic/therapeutic agent described above may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

The thus obtained pharmaceutical preparation is safe and low toxic, and can thus be administered to, for example, human and mammals (e.g., rat, mouse, rabbit, sheep, swine, bovine, cat, dog, monkey, etc.).

The dose of the compound or its salt may vary depending on subject to be administered, target organ, symptom, administration method, etc. When the compound or its salt that increases the expression amount of FPRL1 or FPRL2 of the present invention is orally administered, the compound is administered to a patient with Alzheimer's disease (as 60 kg) generally in a daily dose of approximately 0.1 to 100 mg, preferably approximately 1.0 to 50 mg, more preferably approximately 1.0 to 20 mg. When the compound is parenterally administered, a single dose of the compound may vary depending on subject to be administered, target organ, symptom, administration method, etc. When the compound or its salt that increases the expression amount of FPRL1 or FPRL2 of the present invention is administered to a patient with Alzheimer's disease (as 60 kg) in the form of injection, it is convenient to administer the compound or its salt by intravenous injection, generally in a daily dose of approximately 0.01 to 30 mg, preferably approximately 0.1 to 20 mg, more preferably approximately 0.1 to 10 mg. For other animal species, the corresponding dose as converted per 60 kg weight can be administered.

(4) Diagnostic Method Using the Antibody of the Present Invention

The antibody of the present invention is capable of specifically recognizing FPRL1 or FPRL2 of the present invention and can thus be used for detection or neutralization of FPRL1 or FPRL2 of the present invention in a test sample fluid.

That is, the present invention provides:

(i) a method for quantification of FPRL1 or FPRL2 in a test sample fluid, which comprises competitively reacting the antibody of the present invention, a test sample fluid and a labeled form of FPRL1 or FPRL2, and measuring the ratio of the labeled FPRL1 or FPRL2 of the present invention bound to said antibody; and (ii) a method for quantification of FPRL1 or FPRL2 in a test sample fluid, which comprises reacting the test sample fluid simultaneously or continuously with the antibody of the present invention immobilized on a carrier and a labeled form of the antibody of the present invention, and then measuring the activity of the labeling agent on the insoluble carrier.

In the quantification method in the above-mentioned (ii); it is desirable that one antibody is an antibody recognizing the N-terminal region of FPRL1 or FPRL2, and the other antibody is an antibody reacting with the C-terminal region of FPRL1 or FPRL2.

The monoclonal antibody to FPRL1 or FPRL2 may be used to quantify FPRL1 or FPRL2. Besides, FPRL1 or FPRL2 may also be detected by means of tissue staining. For these purposes, the antibody molecule per se may be used, or F(ab')$_2$, Fab' or Fab fractions of the antibody molecule may be used as well.

There is no particular limitation to the method of quantifying FPRL1 or FPRL2 using the antibody of the present invention; any method may be used so far as it relates to a method in which the amount of antibody, antigen or antibody-antigen complex can be detected by a chemical or a physical means, depending on or corresponding to the amount of antigen (e.g., the amount of FPRL1 or FPRL2) in a test sample fluid to be assayed, and then calculated using a standard curve prepared by a standard solution containing the known amount of antigen. Advantageously used are, for example, nephrometry, competitive method, immunometric method and sandwich method; in terms of sensitivity and specificity, the sandwich method, which will be later described, is particularly preferred.

Examples of the labeling agent used in the assay method using the labeling substance are radioisotopes, enzymes, fluorescent substances, luminescent substances, etc. Examples of the radioisotope are [$^{125}$I], [$^{131}$I], [$^{3}$H], [$^{14}$C], etc. Preferred examples of the enzyme are those that are stable and have a high specific activity, which include β-galactosidase, β-glucosidase, alkaline phosphatase, per-oxidase, malate dehydrogenase, etc. Examples of the fluorescent substance are fluorescamine, fluorescein isothiocyanate, etc. Examples of the luminescent substance are luminol, a luminol derivative, luciferin, lucigenin, etc. Furthermore, the biotin-avidin system may also be used for binding of an antibody or antigen to a labeling agent.

In the immobilization of antigens or antibodies, physical adsorption may be used. Alternatively, chemical binding conventionally used for immobilization of FPRL1 or FPRL2 or enzymes may be used as well. Examples of the carrier include insoluble polysaccharides such as agarose, dextran and cellulose; synthetic resins such as polystyrene, polyacrylamide, silicone, etc.; glass; and the like.

In the sandwich method, a test sample fluid is reacted with an immobilized form of the monoclonal antibody of the present invention (primary reaction), then reacted with another labeled form of the monoclonal antibody of the present invention (secondary reaction) and the activity of the labeling agent on the insoluble carrier is assayed, whereby the amount of FPRL1 or FPRL2 in the test sample fluid can be quantified. The primary and secondary reactions may be carried out in a reversed order, simultaneously or sequentially with an interval. The type of the labeling agent and the method for immobilization may be effected by modifications of those described hereinabove. In the immunoassay by the sandwich method, it is not always necessary that the antibody used for the labeled antibody and for the solid phase should be one type or one species but a mixture of two or more antibodies may be used as well, for the purpose of improving the measurement sensitivity, etc.

In the method for assaying FPRL1 or FPRL2 by the sandwich method according to the present invention, preferred monoclonal antibodies of the present invention used for the primary and the secondary reactions are antibodies whose binding sites to FPRL1 or FPRL2 are different from one another. Thus, the antibodies used in the primary and the secondary reactions are those wherein when the antibody used in the secondary reaction recognizes the C-terminal region of FPRL1 or FPRL2, the antibody recognizing the site other than the C-terminal region, e.g., recognizing the N-terminal region, is preferably used in the primary reaction.

The monoclonal antibody of the present invention may be used in an assay system other than the sandwich method, such as a competitive method, an immunometric method, nephrometry, etc.

In the competitive method, an antigen in a test sample fluid and a labeled antigen are competitively reacted with an antibody, then the unreacted labeled antigen (F) and the labeled antigen bound to the antibody (B) are separated (i.e., B/F separation) and the labeled amount of either B or F is measured to determine the amount of the antigen in the test sample fluid. In the reactions for such a method, there are a liquid phase method in which a soluble antibody is used as the antibody and the B/F separation is effected by polyethylene glycol while a second antibody to the antibody described above is used, and a solid phase method in which an immobilized antibody is used as the first antibody or a soluble antibody is used as the first antibody while an immobilized antibody is used as the second antibody.

In the immunometric method, an antigen in a test sample fluid and an immobilized antigen are competitively reacted with a given amount of a labeled antibody followed by separating the solid phase from the liquid phase; or an antigen in a test sample fluid and an excess amount of labeled antibody are reacted, then an immobilized antigen is added to bind an unreacted labeled antibody to the solid phase, and the solid phase is separated from the liquid phase. Thereafter, the labeled amount of any of the phases is measured to determine the antigen amount in the test sample fluid.

In the nephrometry, the amount of insoluble sediment, which is produced as a result of the antigen-antibody reaction in a gel or in a solution, is measured. Even when the amount of an antigen in a test sample fluid is small and only a small amount of the sediment is obtained, laser nephrometry utilizing laser scattering can be suitably used.

In applying each of those immunoassays to the quantification method of the present invention, any special conditions or operations are not required to set forth. The assay system for FPRL1 of the present invention may be constructed in addition to conditions or operations conventionally used for each of the methods, taking the technical consideration by one skilled in the art into account. For the details of such conventional technical means, a variety of reviews, reference books, etc. may be referred to (for example, Hiroshi Irie (ed.): "Radioimmunoassay" (published by Kodansha, 1974); Hiroshi Irie (ed.): "Radioimmunoassay; Second Series" (published by Kodansha, 1979); Eiji Ishikawa, et al. (ed.): "Enzyme Immunoassay" (published by Igaku Shoin, 1978); Eiji Ishikawa, et al. (ed.): "Enzyme Immunoassay" (Second Edition) (published by Igaku Shoin, 1982); Eiji Ishikawa, et al. (ed.): "Enzyme Immunoassay" (Third Edition) (published by Igaku Shoin, 1987); "Methods in Enzymology" Vol. 70 (Immuochemical Techniques (Part A)); ibid., Vol. 73 (Immunochemical Techniques (Part B)); ibid., Vol. 74 (Immunochemical Techniques (Part C)); ibid., Vol. 84 (Immunochemical Techniques (Part D: Selected Immunoassays)); ibid., Vol. 92 (Immunochemical Techniques (Part E: Monoclonal Antibodies and General Immunoassay Methods)); ibid., Vol. 121 (Immunochemical Techniques (Part I: Hybridoma Technology and Monoclonal Antibodies)) (published by Academic Press); etc.)

As described above, FPRL1 of the present invention can be quantified with high sensitivity, using the antibody of the present invention.

Furthermore, when a decrease in the concentration of FPRL1 or FPRL2 is detected by quantifying the concentration of FPRL1 or FPRL2 using the antibody of the present invention, it can be diagnosed that it is highly likely to suffer from diseases, for example, diseases involving nerve degeneration, for example, nerve degeneration diseases (for example, Alzheimer's disease [familial Alzheimer's disease, early-onset Alzheimer's disease, sporadic Alzheimer's disease etc.], Parkinson's disease, Down's syndrome, amyotrophic lateral sclerosis, prion disease, Creutzfeldt-Jakob disease, Huntington's disease, diabetic neuropathy, multiple sclerosis etc.), brain function disorders (for example, cerebral infarction, cerebral hemorrhage, subarachnoid hemorrhage, ischemic cerebral disease, epidural hematoma, subdural hematoma etc.), cancers (for example, astrocytoma, oligodendrocytoma etc.), immune diseases, infection diseases (for example, meningitis, protozoan infection, rickettia infection, protozoa metazoan infection, bacterial or viral meningitis such as Boma disease, encephalitis after vaccine inoculation, dementia associated with AIDS, etc.), alimentary diseases, circulatory diseases, endocrine diseases etc.

When an increase in the concentration of FPRL1 or FPRL2 is detected, it can be diagnosed that for example a disease associated with overexpression of FPRL1 or FPRL2 is involved or it is highly likely to suffer from such a disease in the future.

(5) Determination of Agonists to FPRL1 or FPRL2 of the Present Invention

Upon binding humanin to FPRL1 or FPRL2, inhibition of intracellular cAMP formation is observed. Accordingly, FPRL1 or FPRL2 is useful as a reagent for searching and determining non-humanin agonists (including naturally occurring ligands) to FPRL1 or FPRL2 by using, as an indicator, an inhibitory activity on intracellular cAMP formation.

That is, the present invention provides a method for determining an agonist to FPRL1 or FPRL2, which comprises measuring an inhibitory activity on intracellular cAMP formation via FPRL1 or FPRL2, upon bringing a test compound into contact with a cell containing FPRL1 or FPRL2.

Examples of the test compound include publicly known ligands (e.g., angiotensin, bombesin, canavinoid, cholecystokinin, glutamine, serotonin, melatonin, neuropeptide Y, opioid, purines, vasopressin, oxytocin, PACAP (e.g., PACAP27, PACAP38), secretin, glucagon, calcitonin, adrenomedulin, somatostatin, GHRH, CRF, ACTH, GRP, PTH, VIP (vasoactive intestinal and related polypeptide), somatostatin, dopamine, motilin, amylin, bradykinin, CGRP (calcitonin gene-related peptide), leukotrienes, pancreastatin, prostaglandins, thromboxane, adenosine, adrenaline, a chemokine superfamily (e.g., CXC chemokine subfamily such as IL-8, GROα, GROβ, GROγ, NAP-2, ENA-78, GCP-2, PF4, IP10, Mig, PBSF/SDF-1, etc.; CC chemokine subfamily such as MCAF/MCP-1, MCP-2, MCP-3, MCP-4, eotaxin, RANTES, MIP1-α, MIP-1β, HCC-1, MIP-3α/LARC, MIP-3β/ELC, I-309, TARC, MIPF-1, MIPF-2/eotaxin-2, MDC, DC-CK1/PARC, SLC, etc.; C chemokine subfamily such as lymphotactin; and CX3C chemokine subfamily such as fractalkine, etc.), endothelin, enterogastrin, histamine, neurotensin, TRH, pancreatic polypeptide, galanin, lysophosphatidic acid (LPA), sphingosine 1-phosphate, etc.) as well as other substances, for example, tissue extracts and cell culture supernatants from humans or mammals (e.g., mice, rats, swine, bovine, sheep, monkeys, etc.). For example, the tissue extract or cell culture supernatant is added to FPRL1 or FPRL2 and fractionated while assaying the cellular stimulating activities, etc. to finally give a single ligand.

The test compounds may form salts, and as salts of the test compounds, use is made of salts with physiologically acceptable acids (e.g., inorganic acids etc.) or bases (e.g., organic acids [sic] etc.), preferably physiologically acceptable acid addition salts. Examples of such salts are salts with inorganic acids (e.g., hydrochloric acid, phosphoric acid, hydrobromic acid, sulfuric acid etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid etc.) and the like.

Specifically, the method of determining an agonist to FPRL1 or FPRL2 is a method which comprises determining a compound or its salt having an FPRL1- or FPRL2-mediated inhibitory activity on intracellular cAMP production in a receptor binding assay system using an expression system constructed using the recombinant FPRL1 or FPRL2 of the present invention.

More specifically, the present invention provides the following determination methods:

(1) a method of determining an agonist to FPRL1 or FPRL2, which comprises measuring the FPRL1- or FPRL2-mediated inhibitory activity on intracellular cAMP production upon bringing a test compound into contact with cells containing FPRL1 or FPRL2, and (2) a method of determining an agonist to FPRL1 or FPRL2, which comprises measuring the FPRL1- or FPRL2-mediated inhibitory activity on intracellular cAMP production upon bringing a test compound into contact with FPRL1 or FPRL2 expressed on a cell membrane induced by culturing a transformant harboring FPRL1 DNA or FPRL2 DNA.

The above test is conducted particularly preferably after it is confirmed that the test compound is bound to FPRL1 or FPRL2.

In the method of determining an agonist according to the present invention, when cells containing FPRL1 or FPRL2 are used, the cells may be fixed with glutaraldehyde, formalin, etc. The cells can be fixed by publicly known methods.

The cell membrane fraction containing FPRL1 or FPRL2 refers to a fraction abundant in cell membrane obtained by cell disruption and subsequent fractionation by a publicly known method. Cell disruption methods include cell squashing using a Potter-Elvehjem homogenizer, disruption using a Waring blender or Polytron (manufactured by Kinematica Inc.), disruption by ultrasonication, and disruption by cell spraying through thin nozzles under an increased pressure using a French press or the like. Cell membrane fractionation is effected mainly by fractionation using a centrifugal force, such as centrifugation for fractionation and density gradient centrifugation. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in FPRL1 or FPRL2 expressed and membrane components such as cell-derived phospholipids and membrane proteins.

The amount of FPRL1 or FPRL2 in the cells containing FPRL1 or FPRL2 and in the membrane fraction is preferably $10^3$ to $10^8$ molecules per cell, more preferably $10^5$ to $10^7$ molecules per cell. As the amount of expression increases, the ligand binding activity per unit of membrane fraction (specific activity) increases so that not only the highly sensitive screening system can be constructed but also large quantities of samples can be assayed with the same lot.

In the method for determination of an agonist according to the present invention, the inhibitory activity on intracellular cAMP formation via FPRL1 or FPRL2 may be determined by a publicly known method, or using an assay kit commercially available. Specifically, cells containing FPRL1 or FPRL2 are first cultured on a multi-well plate, etc. Prior to the agonist determination, the medium is replaced with fresh medium or with an appropriate non-cytotoxic buffer, followed by incubation for a given period of time in the presence of a test compound, etc. Subsequently, the cells are extracted or the supernatant is recovered and the resulting product is quantified by appropriate procedures. Where it is difficult to detect the production of the index substance (e.g., cAMP) for the cell-stimulating activity due to a degrading enzyme contained in the cells, an inhibitor against such a degrading enzyme may be added prior to the assay.

The kit for determination of an agonist according to the present invention comprises cells containing FPRL1 or FPRL2 or their cell membrane fraction.

By using the method for determination of an agonist according to the present invention, compounds that exhibit the inhibitory activity on intracellular cAMP production can be selected as the agonist to FPRL1 or FPRL2.

The thus determined agonist to FPRL1 or FPRL2 can be used for example as an apotosis inhibitor and as a low toxic and safe pharmaceutical preparation such as a prophylactic/therapeutic agent for diseases involving nerve degeneration, for example, nerve degeneration diseases (for example, Alzheimer's disease [familial Alzheimer's disease, early-onset Alzheimer's disease, sporadic Alzheimer's disease etc.], Parkinson's disease, Down's syndrome, amyotrophic lateral sclerosis, prion disease, Creutzfeldt-Jakob disease, Huntington's disease, diabetic neuropathy, multiple sclerosis etc.), brain function disorders (for example, cerebral infarction, cerebral hemorrhage, subarachnoid hemorrhage, ischemic cerebral disease, epidural hematoma, subdural hematoma etc.), cancers (for example, astrocytoma, oligodendrocytoma etc.), immune diseases, infection diseases (for example, meningitis, protozoan infection, rickettia infection, protozoa metazoan infection, bacterial or viral meningitis such as Boma disease, encephalitis after vaccine inoculation, dementia associated with AIDS, etc.), alimentary diseases, circulatory diseases, endocrine diseases etc., preferably as a prophylactic/therapeutic agent for nerve degeneration diseases and brain function disorders, more preferably as a prophylactic/therapeutic agent for Alzheimer's disease.

(6) Methods of Screening Compounds or their Salts (Agonists, Antagonists, or the Like) that Alter the Binding Property or Signal Transduction Between FPRL1 or FPRL2 of the Present Invention and Humanin, and Pharmaceuticals Comprising Compounds or their Salts that Alter the Binding Property or Signal Transduction Between FPRL1 or FPRL2 of the Present Invention and Humanin Using FPRL1 or FPRL2 of the present invention, or using the receptor binding assay system of the expression system constructed using the recombinant FPRL1 or FPRL2, compounds (e.g., peptides, proteins, non-peptide compounds, synthetic compounds, fermentation products, etc.) or salt forms thereof that alter the binding property or signal transduction between the ligand humanin and FPRL1 or FPRL2 of the present invention can be efficiently screened.

Such compounds include (a) compounds that have the FPRL1- or FPRL2-mediated cell-stimulating activity (so-called agonists to FPRL1 or FPRL2 of the present invention), (b) compounds that inhibit the FPRL1- or FPRL2-mediated cell-stimulating activity (so-called antagonists to FPRL1 or FPRL2 of the present invention), (c) compounds that potentiate the binding affinity between humanin and FPRL1 or FPRL2 of the present invention, and (d) compounds that reduce the binding affinity between humanin and FPRL1 or FPRL2 of the present invention.

That is, the present invention provides methods of screening compounds or their salts that alter the binding property or signal transduction between humanin and FPRL1 or FPRL2 of the present invention, which comprises comparing (i) the case wherein FPRL1 or FPRL2 of the present invention is brought into contact with humanin, with (ii) the case wherein FPRL1 or FPRL2 of the present invention is brought into contact with humanin and a test compound.

The screening methods of the present invention are characterized by assaying, for example, the amount of humanin bound to FPRL1 or FPRL2, the cell-stimulating activity, etc., and comparing the property between (i) and (ii).

The cell-stimulating activity includes, for example, activities that promote or suppress arachidonic acid release, acetylcholine release, intracellular $Ca^{2+}$ release, intracellular cAMP production, intracellular cGMP production, inositol phosphate production, changes in cell membrane potential, phosphorylation of intracellular proteins, activation of c-fos, pH reduction, etc., among which the activity that suppresses intracellular cAMP production is preferably used.

More specifically, the present invention provides the following screening methods:

a) A method of screening a compound or its salt that alters the binding property or signal transduction between humanin and FPRL1 or FPRL2 of the present invention, which comprises measuring and comparing the amount of labeled humanin bound to FPRL1 or FPRL2, when the labeled humanin is brought into contact with FPRL1 or FPRL2 of the present invention and when the labeled humanin and a test compound are brought into contact with FPRL1 or FPRL2 of the present invention;

b) A method of screening a compound or its salt that alters the binding property or signal transduction between humanin and FPRL1 or FPRL2 of the present invention, which comprises measuring and comparing the amount of labeled humanin bound to cells or the membrane fraction of the cells, when the labeled humanin is brought into contact with the cells or cell membrane fraction containing FPRL1 or FPRL2 of the present invention and when the labeled humanin and a test compound are brought into contact with the cells or cell membrane fraction containing FPRL1 or FPRL2 of the present invention;

c) A method of screening a compound or its salt that alters the binding property or information transduction between humanin and FPRL1 or FPRL2 of the present invention, which comprises measuring and comparing the amount of labeled humanin to FPRL1 or FPRL2, when the labeled humanin is brought into contact with FPRL1 or FPRL2 expressed on the cell membrane induced by culturing a transformant containing the DNA of the present invention and when the labeled humanin and a test compound are brought into contact with FPRL1 or FPRL2 of the present invention expressed on the cell membrane induced by culturing a transformant containing the DNA of the present invention;

d) A method of screening a compound or its salt that alters the binding property or information transduction between humanin and FPRL1 or FPRL2 of the present invention, which comprises measuring and comparing the FPRL1- or FPRL2-mediated cell-stimulating activity, when a compound or its salt (e.g., humanin) that activates FPRL1 or FPRL2 of the present invention is brought into contact with cells containing FPRL1 or FPRL2 of the present invention and when the compound that activates FPRL1 or FPRL2 of the present invention and a test compound are brought into contact with cells containing FPRL1 or FPRL2 of the present invention; and e) A method of screening a compound or its salt that alters the binding property or information transduction between humanin and FPRL1 or FPRL2 of the present invention, which comprises measuring and comparing the FPRL1- or FPRL2-mediated cell-stimulating activity, when a compound or its salt (e.g., humanin) that activates FPRL1 or FPRL2 of the present invention is brought into contact with FPRL1 or FPRL2 of the present invention expressed on the cell membrane induced by culturing a transformant containing the DNA of the present invention and when the compound that activates FPRL1 or FPRL2 of the present invention and a test compound are brought into contact with FPRL1 or FPRL2 of the present invention expressed on the cell membrane induced by culturing a transformant containing the DNA of the present invention.

As the ligand, a compound or its salt that alters the binding property between humanin and FPRL1 or FPRL2 can be used in place of humanin. The compound or its salt that alters the binding property between humanin and FPRL1 or FPRL2 can be obtained for example by performing the screening methods of the present invention described later. In the following screening methods, humanin and compounds or their salts that alter the binding property between humanin and FPRL1 or FPRL2 are referred to collectively as humanin.

Hereinafter, the screening methods of the present invention are described more specifically.

As FPRL1 or FPRL2 of the present invention used in the screening methods of the present invention, any substance may be used so long as it comprises FPRL1 or FPRL2 of the present invention described above. The cell membrane fraction from mammalian organs containing FPRL1 or FPRL2 of the present invention is preferred. However, it is very difficult to obtain human organs, and thus human-derived FPRL1 or FPRL2 or the like, produced by large-scale expression using recombinants, is preferably used in screening.

FPRL1 or FPRL2 of the present invention can be manufactured by the method described above, preferably by expressing the DNA of the present invention in mammalian or insect cells. As DNA fragments encoding the desired portion of the protein, complementary DNA is generally used but not necessarily limited thereto. For example, gene fragments or synthetic DNA may also be used. For introducing a DNA fragment encoding FPRL1 or FPRL2 of the present invention into host animal cells and efficiently expressing the same, it is preferred to insert the DNA fragment downstream a polyhedrin promoter of nuclear polyhedrosis virus (NPV), which is a baculovirus having insect hosts, an SV40-derived promoter, a retrovirus promoter, a metallothionein promoter, a human heat shock promoter, a cytomegalovirus promoter, an SRα promoter or the like. The amount and quality of the receptor expressed can be determined by a publicly known method. For example, this determination can be made by the method described in the literature (Nambi, P., et al., J. Biol. Chem., 267, 19555–19559 (1992)).

Accordingly, the subject containing FPRL1 or FPRL2 of the present invention in the screening method of the present invention may be FPRL1 or FPRL2 purified by publicly known methods, cells containing FPRL1 or FPRL2, or membrane fractions of such cells.

Where cells containing FPRL1 or FPRL2 of the present invention are used in the screening method of the present invention, the cells may be fixed using glutaraldehyde, formalin, etc. The fixation can be made by a publicly known method.

The cells containing FPRL1 or FPRL2 of the present invention are host cells that have expressed the FPRL1 or FPRL2, and the host cells include *Escherichia coli, Bacillus subtilis*, yeast, insect cells, animal cells, and the like.

The cell membrane fraction refers to a fraction abundant in cell membrane obtained by cell disruption and subsequent fractionation by a publicly known method. Cell disruption methods include cell squashing using a Potter-Elvehjem homogenizer, disruption using a Waring blender or Polytron (manufactured by Kinematica Inc.), disruption by ultrasonication, and disruption by cell spraying through thin nozzles under an increased pressure using a French press or the like. Cell membrane fractionation is effected mainly by fractionation using a centrifugal force, such as centrifugation for fractionation and density gradient centrifugation. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in FPRL1 or FPRL2 expressed and membrane components such as cell-derived phospholipids and membrane proteins.

The amount of FPRL1 or FPRL2 in the cells containing FPRL1 or FPRL2 and in the membrane fraction is preferably $10^3$ to $10^8$ molecules per cell, more preferably $10^5$ to $10^7$ molecules per cell. As the amount of expression increases, the ligand binding activity per unit of membrane fraction (specific activity) increases so that not only the highly sensitive screening system can be constructed but also large quantities of samples can be assayed with the same lot.

To perform the above-mentioned a) to c) for screening the compounds or salts thereof that alter the binding property or signal transduction between humanin and FPRL1 or FPRL2 of the present invention, for example, an appropriate FPRL1 or FPRL2 fraction and labeled humanin are necessary.

The FPRL1 or FPRL2 fraction is preferably a fraction of naturally occurring FPRL1 or FPRL2 or a recombinant FPRL1 or FPRL2 fraction having an activity equivalent to that of natural FPRL1 or FPRL2. Herein, the equivalent activity is intended to mean a ligand binding activity, a signal information transduction activity or the like that is equivalent to that possessed by naturally occurring FPRL1 or FPRL2.

As labeled humanin, for example humanin labeled with [$^3$H], [$^{125}$I], [$^{14}$C], [$^{35}$S] or the like is used.

Specifically, to screen the compounds that alter the binding property or signal transmission between humanin and FPRL1 or FPRL2 of the present invention, first, an FPRL1 or FPRL2 standard is prepared by suspending cells or cell membrane fraction containing FPRL1 or FPRL2 of the present invention in a buffer appropriate for the screening. As the buffer, any buffer that does not interfere with the binding between humanin and FPRL1 or FPRL2 is usable and examples of such a buffer are phosphate buffer, Tris-hydrochloride buffer, etc., having pH of 4 to 10 (preferably pH of 6 to 8). To minimize non-specific binding, a surfactant such as CHAPS, Tween-80™ (Kao-Atlas Co.), digitonin, deoxycholate, etc. may be added to the buffer. To inhibit degradation of the receptor and humanin by proteases, protease inhibitors such as PMSF, leupeptin, E-64 (manufactured by Peptide Research Laboratory, Co.), and pepstatin may be added. To 0.01 to 10 ml of the receptor solution, a given amount (5,000 to 500,000 cpm) of labeled humanin is added, and $10^{-4}$ M to $10^{-10}$ M of a test compound is simultaneously added to be co-present. To examine non-specific binding (NSB), a reaction tube containing unlabeled humanin in a large excess is also prepared. The reaction is carried out at approximately 0 to 50° C., preferably about 4 to 37° C. for about 20 minutes to about 24 hours, preferably about 30 minutes to about 3 hours. After completion of the reaction, the reaction mixture is filtrated through glass fiber filter paper, etc. and washed with an appropriate volume of the same buffer. The residual radioactivity on the glass fiber filter paper is then measured by means of a liquid scintillation counter or γ-counter. Assuming that the count obtained by subtracting the amount of non-specific binding (NSB) from the count obtained in the absence of any competitive substance ($B_0$) is 100%, the test compound by which the amount of specific binding (B-NSB) is reduced to e.g. 50% or less can be selected as a candidate substance having a potential of competitive inhibition.

To perform the methods d) to e) supra of screening the compounds that alter the binding property and signal transduction between humanin and FPRL1 or FPRL2 of the present invention, the FPRL1- or FPRL2-mediated cell-stimulating activity can be measured using publicly known methods or commercially available kits.

Specifically, the cells containing FPRL1 or FPRL2 of the present invention are first cultured on a multi-well plate, etc. Prior to screening, the medium is replaced with fresh medium or with an appropriate non-cytotoxic buffer, followed by incubation for a given period of time in the presence of a test compound, etc. Subsequently, the cells are extracted or the supernatant is recovered and the resulting product is quantified by appropriate procedures. Where it is difficult to detect the production of the index substance (e.g., cAMP, arachidonic acid etc.) for the cell-stimulating activity due to a degrading enzyme contained in the cells, an inhibitor against such a degrading enzyme may be added prior to the assay. For detecting activities such as the cAMP production suppression activity, the baseline production in the cells is increased by forskolin or the like and the suppressing effect on the increased baseline production may then be detected.

Screening by assaying the cell-stimulating activity requires cells that have expressed appropriate FPRL1 or FPRL2. For the cells that have expressed FPRL1 or FPRL2 of the present invention, the cell strain possessing naturally occurring FPRL1 or FPRL2 of the present invention, the cell strain expressing the recombinant FPRL1 or FPRL2 described above and the like are desirable.

For the test compound, for example, peptides, proteins, non-peptide compounds, synthetic compounds, fermentation products, cell extracts, plant extracts, and animal tissue extracts are used. These compounds may be novel or known compounds.

The test compounds may form salts, and as salts of the test compounds, use is made of salts with physiologically acceptable acids (e.g., inorganic acids etc.) or bases (e.g., organic acids [sic] etc.), preferably physiologically acceptable acid addition salts. Examples of such salts are salts with inorganic acids (e.g., hydrochloric acid, phosphoric acid, hydrobromic acid, sulfuric acid etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid etc.) and the like.

The test compound used is preferably a compound which on the basis of the atomic coordinates of an FPRL1or FPRL2 active site and the position of a ligand binding pocket, is designed to bind to the ligand binding pocket. The atomic coordinates of the FPRL1 or FPRL2 active site and the position of the ligand binding pocket can be measured by a known method or a modification thereof.

Whether the compound or its salt that alters the binding property between humanin and FPRL1 or FPRL2 is an agonist or antagonist can be confirmed by the above-described method of screening an agonist to FPRL1 or FPRL2.

The kit for screening the compounds or salts thereof that alter the binding property or signal transduction between humanin and FPRL1 or FPRL2 of the present invention comprises FPRL1 or FPRL2 of the present invention, cells containing FPRL1 or FPRL2 of the present invention, or a membrane fraction of cells containing FPRL1 or FPRL2 of the present invention.

For example, the screening kit of the present invention includes:

1. Screening Reagents a) Buffer for Measurement and Washing

Hanks' balanced salt solution (manufactured by Gibco Co.) supplemented with 0.05% bovine serum albumin (manufactured by Sigma Co.).

The solution is sterilized by filtration through a 0.45 μm filter, and stored at 4° C. or may be prepared at use.

b) FPRL1 Standard or FPRL2 Standard

CHO cells expressing FPRL1 or FPRL2 of the present invention are passaged in a 12-well plate at a density of $5 \times 10^5$ cells/well followed by culturing at 37° C. under 5% $CO_2$ and 95% air for 2 days.

c) Labeled Humanin

Aqueous solutions of humanin labeled with commercially available [$^3$H], [$^{125}$I], [$^{14}$C], [$^{35}$S], etc. are stored at 4° C. or −20° C., and diluted to 1 μM with the measurement buffer just before use.

d) Standard Humanin Solution

Humanin is dissolved in and adjusted to 1 mM with PBS containing 0.1% bovine serum albumin (manufactured by Sigma Co.) and stored at −20° C.

2. Measurement Method a) CHO cells expressing FPRL1 or FPRL2 of the present invention are cultured in a 12-well culture plate and washed twice with 1 ml of the measurement buffer, and 490 μl of the measurement buffer is added to each well.

b) After adding 5 μl of $10^{-3}$ to $10^{-10}$ M test compound solution, 5 μl of labeled humanin is added to the mixture, and the cells are incubated at room temperature for 1 hour. To determine the amount of the non-specific binding, 5 of $10^{-3}$ M humanin is added in place of the test compound.

c) The reaction solution is removed, and the wells are washed 3 times with 1 ml of the washing buffer. The labeled humanin bound to the cells is dissolved in 0.2 N NaOH-1% SDS, and mixed with 4 ml of liquid scintillator A (manufactured by Wako Pure Chemical Industries, Ltd.).

d) The radioactivity is measured using a liquid scintillation counter (manufactured by Beckman Co.), and the percent maximum binding (PMB) is calculated by the equation below.

$$PMB = [(B - NSB)/(B_0 - NSB)] \times 100$$

PMB: Percent maximum binding
B: Value obtained in the presence of a test compound
NSB: Non-specific binding
$B_0$: Maximum binding The compounds or their salts, which are obtainable using the screening methods or the screening kits of the present invention, are the compounds that alter the binding property or signal transduction between humanin and FPRL1 or FPRL2 of the present invention. Specifically, these compounds include (a) compounds that have the FPRL1- or FPRL2-mediated cell-stimulating activity, activity that promotes or inhibits pH reduction, etc. (so-called agonists to FPRL1 or FPRL2 of the present invention), (b) compounds having no cell stimulating-activity (so-called antagonists to FPRL1 or FPRL2 of the present invention), (c) compounds that increase the binding affinity between humanin and FPRL1 or FPRL2 of the present invention, and (d) compounds that reduce the binding affinity between humanin and FPRL1 or FPRL2 of the present invention.

The compounds which are obtainable using the screening methods or the screening kits of the present invention include peptides, proteins, non-peptide compounds, synthetic compounds and fermentation products, and may be novel or known compounds.

As salts of the compounds, use is made of salts with physiologically acceptable acids (e.g., inorganic acids etc.) or bases (e.g., organic acids [sic] etc.), preferably physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid etc.) and the like.

Since agonists to FPRL1 or FPRL2 of the present invention have the same physiological activities as those of humanin, the agonists are useful as safe and low toxic pharmaceuticals, correspondingly to the physiological activities of humanin.

Since antagonists to FPRL1 or FPRL2 of the present invention can suppress the physiological activities of humanin, the antagonists are useful as safe and low toxic pharmaceuticals that inhibit the physiological activities of humanin.

The compounds or their salts that increase the binding affinity between humanin and FPRL1 or FPRL2 of the present invention are useful as safe and low toxic pharmaceuticals to potentiate the physiological activities of humanin.

The compounds that reduce the binding affinity between humanin and FPRL1 or FPRL2 of the present invention are useful as safe and low toxic pharmaceuticals that decrease the physiological activities of humanin.

Specifically, the agonist or the compound or its salt obtainable using the screening method or screening kit of the present invention, which enhances the binding property between humanin and FPRL1 or FPRL2 of the present invention, can be used for example as an apotosis inhibitor and as a low toxic and safe pharmaceutical preparation such as a prophylactic/therapeutic agent for diseases involving nerve degeneration, for example, nerve degeneration diseases (for example, Alzheimer's disease [familial Alzheimer's disease, early-onset Alzheimer's disease, sporadic Alzheimer's disease etc.], Parkinson's disease, Down's syndrome, amyotrophic lateral sclerosis, prion disease, Creutzfeldt-Jakob disease, Huntington's disease, diabetic neuropathy, multiple sclerosis etc.), brain function disorders (for example, cerebral infarction, cerebral hemorrhage, subarachnoid hemorrhage, ischemic cerebral disease, epidural hematoma, subdural hematoma etc.), cancers (for example, astrocytoma, oligodendrocytoma etc.), immune diseases, infection diseases (for example, meningitis, protozoan infection, rickettia infection, protozoa metazoan infection, bacterial or viral meningitis such as Borna disease, encephalitis after vaccine inoculation, dementia associated with AIDS, etc.), alimentary diseases, circulatory diseases, endocrine diseases etc., preferably as a prophylactic/therapeutic agent for nerve degeneration diseases and brain function disorders, more preferably as a prophylactic/therapeutic agent for Alzheimer's disease.

On the other hand, the antagonist or the compound or its salt obtainable using the screening method of the present invention, which reduces the binding property between humanin and FPRL1 or FPRL2 of the present invention, can be used as a pharmaceutical preparation such as a prophylactic/therapeutic agent for diseases caused by overexpression of FPRL1 or FPRL2 of the present invention.

Among the antagonists obtained by the screening method described above, those inhibiting the binding between β-amyloid (1-42) and FPRL1 can be used for example as an apotosis inhibitor and as a low toxic and safe pharmaceutical for example as an apotosis inhibitor and as a low toxic and safe pharmaceutical preparation such as a prophylactic/therapeutic agent for diseases involving nerve degeneration, for example, nerve degeneration diseases (for example, Alzheimer's disease [familial Alzheimer's disease, early-onset Alzheimer's disease, sporadic Alzheimer's disease etc.], Parkinson's disease, Down's syndrome, amyotrophic lateral sclerosis, prion disease, Creutzfeldt-Jakob disease, Huntington's disease, diabetic neuropathy, multiple sclerosis etc.), brain function disorders (for example, cerebral infarction, cerebral hemorrhage, subarachnoid hemorrhage, ischemic cerebral disease, epidural hematoma, subdural hematoma etc.), cancers (for example, astrocytoma, oligodendrocytoma etc.), immune diseases, infection diseases (for example, meningitis, protozoan infection, rickettia infection, protozoa metazoan infection, bacterial or viral meningitis such as Borna disease, encephalitis after vaccine inoculation, dementia associated with AIDS, etc.), alimentary diseases, circulatory diseases, endocrine diseases etc., preferably as a prophylactic/therapeutic agent for nerve degeneration diseases and brain function disorders, more preferably as a prophylactic/therapeutic agent for Alzheimer's disease.

When the compound or its salt obtainable using the screening method or screening kit of the present invention is used as the pharmaceutical composition supra, it can be prepared into a pharmaceutical composition in a conventional manner.

For example, the compound or its salt can be used orally, for example, in the form of tablets which may be sugar coated if necessary and desired, capsules, elixirs, microcapsules etc., or parenterally in the form of injectable preparations such as a sterile solution and a suspension in water or with other pharmaceutically acceptable liquid. These preparations can be manufactured for example by mixing the compound or its salt with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin, alginic acid, etc., a lubricant such as magnesium stearate, a sweetening agent such as sucrose, lactose or saccharin, and a flavoring agent such as peppermint, akamono oil or cherry. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil, coconut oil, etc. to prepare the pharmaceutical composition. Examples of an aqueous medium for injection include physiological saline and an isotonic solution containing glucose and other auxiliary agents (e.g., D-sorbitol, D-mannitol, sodium chloride, etc.) and may be used in combination with an appropriate solubilizer such as an alcohol (e.g., ethanol), a polyalcohol (e.g., propylene glycol and polyethylene glycol), a nonionic surfactant (e.g., polysorbate 80™ and HCO-50), etc. Examples of the oily medium include sesame oil, soybean oil, etc., which may also be used in combination with a solubilizer such as benzyl benzoate, benzyl alcohol, etc.

The prophylactic/therapeutic agent described above may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

The thus obtained pharmaceutical preparation is safe and low toxic, and can thus be administered to, for example, human and mammals (e.g., rat, mouse, rabbit, sheep, swine, bovine, cat, dog, monkey, etc.).

The dose of the compound or its salt may vary depending on subject to be administered, target organ, symptom, administration method, etc. In oral administration, the agonist to FPRL1 or FPRL2 is administered to a patient with Alzheimer's disease (as 60 kg) generally in a daily dose of approximately 0.1 to 100 mg, preferably approximately 1.0 to 50 mg, more preferably approximately 1.0 to 20 mg. In parenteral administration, a single dose of the agonist to FPRL1 or FPRL2 may vary depending on subject to be administered, target organ, symptom, administration method, etc. In administration in the form of an injection to e.g. a patient with Alzheimer's disease (as 60 kg), it is convenient to administer the agonist to FPRL1 or FPRL2 by intravenous injection generally in a daily dose of approximately 0.01 to 30 mg, preferably approximately 0.1 to 20 mg, more preferably approximately 0.1 to 10 mg. For other animal species, the corresponding dose as converted per 60 kg weight can be administered.

(7) Method of Elucidating the Working Mechanism of Various Chemicals

By using FPRL1 or FPRL2, it can be confirmed whether various chemicals exhibit pharmacological effects via FPRL1 or FPRL2.

That is, the present invention provides:

(1) a method of confirming that (i) an apotosis inhibitor, (ii) a prophylactic/therapeutic agent for diseases involving nerve degeneration, for example, nerve degeneration diseases (for example, Alzheimer's disease [familial Alzheimer's disease, early-onset Alzheimer's disease, sporadic Alzheimer's disease etc.], Parkinson's disease, Down's syndrome, amyotrophic lateral sclerosis, prion disease, Creutzfeldt-Jakob disease, Huntington's disease, diabetic neuropathy, multiple sclerosis etc.), brain function disorders (for example, cerebral infarction, cerebral hemorrhage, subarachnoid hemorrhage, ischemic cerebral disease, epidural hematoma, subdural hematoma etc.), cancers (for example, astrocytoma, oligodendrocytoma etc.), immune diseases, infection diseases (for example, meningitis, protozoan infection, rickettia infection, protozoa metazoan infection, bacterial or viral meningitis such as Borna disease, encephalitis after vaccine inoculation, dementia associated with AIDS, etc.), alimentary diseases, circulatory diseases, endocrine diseases etc., or (iii) a prophylactic/therapeutic agent for diseases caused by overexpression of FPRL1 or FPRL2 of the present invention, is bound to FPRL1 or FPRL2, said method comprising use of FPRL1 or FPRL2, (2) a method of confirming that (i) an apotosis inhibitor or (ii) a prophylactic/therapeutic agent for diseases involving nerve degeneration, for example, nerve degeneration diseases (for example, Alzheimer's disease [familial Alzheimer's disease, early-onset Alzheimer's disease, sporadic Alzheimer's disease etc.], Parkinson's disease, Down's syndrome, amyotrophic lateral sclerosis, prion disease, Creutzfeldt-Jakob disease, Huntington's disease, diabetic neuropathy, multiple sclerosis etc.), brain function disorders (for example, cerebral infarction, cerebral hemorrhage, subarachnoid hemorrhage, ischemic cerebral disease, epidural hematoma, subdural hematoma etc.), cancers (for example, astrocytoma, oligodendrocytoma etc.), immune diseases, infection diseases (for example, meningitis, protozoan infection, rickettia infection, protozoa metazoan infection, bacterial or viral meningitis such as Borna disease, encephalitis after vaccine inoculation, dementia associated with AIDS, etc.), alimentary diseases, circulatory diseases, endocrine diseases etc., is an agonist to FPRL1 or FPRL2, said method comprising use of FPRL1 or FPRL2, (3) a method of confirming that the prophylactic/therapeutic agent for diseases caused by overexpression of FPRL1 or FPRL2 of the present invention is an antagonist to FPRL1 or FPRL2, said method comprising use of FPRL1 or FPRL2, and (4) the screening method according to the above-mentioned (1) to (3), which comprises measuring the amount of FPRL1 or FPRL2 bound to each reagent upon bringing each reagent into contact with FPRL1 or FPRL2.

This confirmation method can be carried out by the above-described method of screening a compound that alters the binding property between humanin and FPRL1 or FPRL2, wherein the above chemical is used in place of a test compound.

The kit for kit for the confirmation method of the present invention comprises the above chemical in place of a test compound in the above-described kit for screening a compound that alters the binding property between humanin and FPRL1 or FPRL2.

By using the confirmation method of the present invention in this manner, it can be confirmed that a wide variety of chemicals commercially available or under development exhibit pharmacological effects via FPRL1 or FPRL2.

(8) Pharmaceutical Preparation Comprising a Compound or its Salt that Alters the Amount of FPRL1 or FPRL2 of the Present Invention in Cell Membranes The antibody of the present invention can specifically recognize FPRL1 or FPRL2 of the present invention, and can thus be used in screening a compound or its salt that alters the amount of FPRL1 or FPRL2 of the present invention in cell membranes.

That is, the present invention provides, for example:

(i) a method of screening a compound or its salt that alters the amount of FPRL1 or FPRL2 of the present invention in cell membranes, which comprises disrupting a) blood, b) specific organs, or c) tissues or cells isolated from organs, then isolating a cell membrane fraction and quantifying FPRL1 or FPRL2 of the present invention contained in the cell membrane fraction;

(ii) a method of screening a compound or its salt that alters the amount of FPRL1 or FPRL2 of the present invention in cell membranes, which comprises disrupting e.g. an transformant expressing FPRL1 or FPRL2 of the present invention, then isolating a cell membrane fraction and quantifying FPRL1 or FPRL2 of the present invention contained in the cell membrane fraction;

(iii) a method of screening a compound or its salt that alters the amount of FPRL1 or FPRL2 of the present invention in cell membranes, which comprises preparing a section of a) blood, b) specific organs, or c) tissues or cells of organs isolated from a non-human mammal and quantifying the degree of staining of the receptor protein on a cell surface layer by immune staining thereby confirming the protein on the cell surface layer; and iv) a method of screening a compound or its salt that alters the amount of FPRL1 or FPRL2 of the present invention in cell membranes, which comprises preparing a section of e.g. a transformant expressing FPRL1 or FPRL2 of the present invention and quantifying the degree of staining of the receptor protein on a cell surface layer by immune staining thereby confirming the protein on the cell surface layer.

Specifically, FPRL1 or FPRL2 of the present invention contained in the cell membrane fraction is quantified as follows:

(i) Normal or morbid non-human mammals (for example, mice, rats, rabbits, sheep, swine, bovine, cats, dogs, monkeys etc., specifically rats, mice, rabbits etc. with Alzheimer's disease) are given a chemical (for example, an immune regulator etc.) or physical stress (for example, water immersion stress, electrical shock, brightening/darkening, low temperature, etc.), and after a predetermined time, blood, a specific organ (for example, brain, liver, kidney, etc.) or tissues or cells isolated from organs are obtained. The resulting organ, tissues or cells are suspended for example in a suitable buffer (for example, Tris-HCl buffer, phosphate buffer, HEPES buffer etc.) and the organ, tissues or cells are disrupted therein, and a cell membrane fraction is obtained with a surfactant (for example, Triton X100™, Tween 20™ etc.) by techniques such as centrifugation, column fractionation, etc.

The cell membrane fraction is a fraction abundant in cell membrane obtained by cell disruption and subsequent fractionation by a publicly known method. Cell disruption methods include cell squashing using a Potter-Elvehjem homogenizer, disruption using a Waring blender or Polytron (manufactured by Kinematica Inc.), disruption by ultrasonication, and disruption by cell spraying through thin nozzles under an increased pressure using a French press or the like. Cell membrane fractionation is effected mainly by fractionation using a centrifugal force, such as centrifugation for fractionation and density gradient centrifugation. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in FPRL1 or FPRL2 expressed and in membrane components such as cell-derived phospholipids and membrane proteins.

FPRL1 or FPRL2 of the present invention contained in the cell membrane fraction can be quantified by, for example, sandwich immunoassays using the antibody of the present invention, Western blotting analysis, etc.

The sandwich immunoassays can be performed in the same manner as in the method described above, and Western blotting can be performed by a means known per se.

(ii) The transformant expressing FPRL1 or FPRL2 of the present invention is created according to the method descried above, and FPRL1 or FPRL2 of the present invention contained in its cell membrane fraction can be quantified.

Screening of the compound or its salt that alters the amount of FPRL1 or FPRL2 of the present invention in the cell membrane can be carried out by:

(i) administering a test compound into normal or morbid non-human mammals before a predetermined time, that is, 30 minutes to 24 hours before, more preferably 30 minutes to 12 hours before, still more preferably 1 hour to 6 hours before giving chemical or physical stress to the mammals, or after a predetermined time, that is, 30 minutes to 3 days after, preferably 1 hour to 2 days after, more preferably 1 hour to 24 hours after giving chemical or physical stress, or simultaneously with the chemical or physical stress, and quantifying and analyzing the amount of FPRL1 or FPRL2 of the present invention in a cell membrane after a predetermined time, that is, 30 minutes to 3 days after, preferably 1 hour to 2 days after, more preferably 1 hour to 24 hours after the administration, or (ii) mixing a test compound with a medium for culturing the transformant in a usual manner and quantifying and analyzing the amount of FPRL1 or FPRL2 of the present invention in a cell membrane of the transformant after culture, that is, 1 to 7 days later, preferably 1 to 3 days later, more preferably 2 to 3 days later.

Specifically, FPRL1 or FPRL2 of the present invention contained in the cell membrane fraction is confirmed in the following manner.

(iii) Normal or morbid non-human mammals (for example, mice, rats, rabbits, sheep, swine, bovine, cats, dogs, monkeys etc., specifically rats, mice, rabbits etc. with Alzheimer's disease) are given a chemical (for example, an immune regulator etc.) or physical stress (for example, water immersion stress, electrical shock, brightening/darkening, low temperature, etc.), and after a predetermined time, blood, a specific organ (for example, brain, liver, kidney, etc.) or tissues or cells isolated from organs are obtained. The resulting organ, tissues or cells are formed in a usual manner into a tissue section which is then subjected to immune staining with the antibody of the present invention. The degree of staining of the receptor protein in the cell surface layer is quantified to confirm the protein on the cell membrane, whereby the amount of FPRL1 or FPRL2 of the present invention on the cell membrane can be quantitatively or qualitatively confirmed.

(iv) FPRL1 or FPRL2 of the present invention can also be confirmed in an analogous manner by using e.g. the transformant expressing FPRL1 or FPRL2 of the present invention.

Examples of the test compounds include peptides, proteins, non-peptide compounds, synthetic compounds, fermentation products, cell extracts, plant extracts, animal tissue extracts, etc. and these compounds may be novel compounds or publicly known compounds.

The test compounds may form salts, and as salts of the test compounds, use is made of salts with physiologically acceptable acids (e.g., inorganic acids etc.) or bases (e.g., organic acids [sic] etc.), preferably physiologically acceptable acid addition salts. Examples of such salts are salts with inorganic acids (e.g., hydrochloric acid, phosphoric acid, hydrobromic acid, sulfuric acid etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid etc.) and the like.

The compound or its salt obtained using the screening method of the present invention is a compound or its salt having an action of changing the expression level of FPRL1 or FPRL2 of the present invention in the cell membrane, specifically (a) a compound or its salt that increases the expression level of FPRL1 or FPRL2 of the present invention in the cell membrane thereby increasing the FPRL1- or FPRL2-mediated cell-stimulating activity or (b) a compound or its salt that reduces the expression level of FPRL1 or FPRL2 of the present invention in the cell membrane thereby reducing the cell-stimulating activity.

The compounds obtainable by the screening methods of the present invention include peptides, proteins, non-peptide compounds, synthetic compounds and fermentation products, and may be novel compounds or publicly known compounds.

The compounds obtainable by the screening methods of the present invention may form salts, and as salts of the test compounds, use is made of salts with physiologically acceptable acids (e.g., inorganic acids etc.) or bases (e.g., organic acids [sic] etc.), preferably physiologically acceptable acid addition salts. Examples of such salts are salts with inorganic acids (e.g., hydrochloric acid, phosphoric acid, hydrobromic acid, sulfuric acid etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid etc.) and the like.

The compound or its salt that enhances the cell-stimulating activity by increasing the amount of FPRL1 or FPRL2 of the present invention in the cell membrane can be used as a pharmaceutical preparation such as a prophylactic/therapeutic agent for diseases associated with dysfunction of FPRL1 or FPRL2 of the present invention. Specifically, the compound or its salt can be used for example as an apotosis inhibitor and as a low toxic and safe pharmaceutical preparation such as a prophylactic/therapeutic agent for diseases involving nerve degeneration, for example, nerve degeneration diseases (for example, Alzheimer's disease [familial Alzheimer's disease, early-onset Alzheimer's disease, sporadic Alzheimer's disease etc.], Parkinson's disease, Down's syndrome, amyotrophic lateral sclerosis, prion disease, Creutzfeldt-Jakob disease, Huntington's disease, diabetic neuropathy, multiple sclerosis etc.), brain function disorders (for example, cerebral infarction, cerebral hemorrhage, subarachnoid hemorrhage, ischemic cerebral disease, epidural hematoma, subdural hematoma etc.), cancers (for example, astrocytoma, oligodendrocytoma etc.), immune diseases, infection diseases (for example, meningitis, protozoan infection, rickettia infection, protozoa metazoan infection, bacterial or viral meningitis such as Borna disease, encephalitis after vaccine inoculation, dementia associated with AIDS, etc.), alimentary diseases, circulatory diseases, endocrine diseases etc., preferably as a prophylactic/therapeutic agent for nerve degeneration diseases and brain function disorders, more preferably as a prophylactic/therapeutic agent for Alzheimer's disease.

The compound or its salt that reduces the cell-stimulating activity by decreasing the amount of FPRL1 or FPRL2 of the present invention in the cell membrane is useful as a pharmaceutical preparation such as a prophylactic/therapeutic agent for diseases caused by overexpression of FPRL1 or FPRL2 of the present invention.

When the compound or its salt obtainable using the screening kit of the present invention is used as the pharmaceutical composition supra, it can be prepared into a pharmaceutical composition in a conventional manner.

For example, the compound or its salt can be used orally, for example, in the form of tablets which may be sugar coated if necessary and desired, capsules, elixirs, microcapsules etc., or parenterally in the form of injectable preparations such as a sterile solution and a suspension in water or with other pharmaceutically acceptable liquid. These preparations can be manufactured for example by mixing the compound or its salt with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose or saccharin, and a flavoring agent such as peppermint, akamono oil or cherry. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil, coconut oil, etc. to prepare the pharmaceutical composition. Examples of an aqueous medium for injection include physiological saline and an isotonic solution containing glucose and other auxiliary agents (e.g., D-sorbitol, D-mannitol, sodium chloride, etc.) and may be used in combination with an appropriate solubilizer such as an alcohol (e.g., ethanol), a polyalcohol (e.g., propylene glycol and polyethylene glycol), a nonionic surfactant (e.g., polysorbate 80™ and HCO-50), etc. Examples of the oily medium include sesame oil, soybean oil, etc., which may also be used in combination with a solubilizer such as benzyl benzoate, benzyl alcohol, etc.

The prophylactic/therapeutic agent described above may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

The thus obtained pharmaceutical preparation is safe and low toxic, and can thus be administered to, for example, humans and mammals (e.g., rat, mouse, rabbit, sheep, swine, bovine, cat, dog, monkey, etc.).

The dose of the compound or its salt may vary depending on subject to be administered, target organ, symptom, administration method, etc. When the compound or its salt that increases the amount of FPRL1 or FPRL2 of the present invention in the cell membrane is orally administered, the compound or its salt is administered to a patient with Alzheimer's disease (as 60 kg) generally in a daily dose of approximately 0.1 to 100 mg, preferably approximately 1.0 to 50 mg, more preferably approximately 1.0 to 20 mg. When the compound or its salt is parenterally administered, a single dose of the compound or its salt may vary depending on subject to be administered, target organ, symptom, administration method, etc. When the compound or its salt that increases the amount of FPRL1 or FPRL2 of the present invention in the cell membrane is administered to a patient with Alzheimer's disease (as 60 kg) in the form of injection, it is convenient to administer the compound or its salt by intravenous injection, generally in a daily dose of approximately 0.01 to 30 mg, preferably approximately 0.1 to 20 mg, more preferably approximately 0.1 to 10 mg. For other animal species, the corresponding dose as converted per 60 kg weight can be administered.

(9) Pharmaceutical Preparation Comprising the Antibody to FPRL1 or FPRL2 of the Present Invention The neutralizing activity of the antibody to FPRL1 or FPRL2 of the present invention refers to an activity of inactivating the signal transduction function in which FPRL1 or FPRL2 is involved. Therefore, when the antibody has the neutralizing activity, the antibody can inactivate the signal transduction in which FPRL1 or FPRL2 is involved, for example, inactivate the FPRL1- or FPRL2-mediated cell-stimulating activity (e.g., activity that promotes or inhibits arachidonic acid release, acetylcholine release, intracellular $Ca^{2+}$ release, intracellular cAMP production, suppression of intracellular cAMP production, intracellular cGMP production, inositol phosphate production, changes in cell membrane potential, phosphorylation of intracellular proteins, activation of c-fos, pH reduction, particularly suppression of intracellular cAMP production).

Therefore, the antibody FPRL1 or FPRL2 of the present invention (for example, the neutralizing antibody) can be used as a prophylactic/therapeutic agent for diseases caused by overexpression of FPRL1 or FPRL2 or an excess of humanin.

The prophylactic/therapeutic agent can be produced and used in the same manner as for the pharmaceutical preparation comprising FPRL1 or FPRL2 of the present invention described above.

(10) Pharmaceutical Preparation Comprising the Antisense DNA of the Present Invention The antisense DNA of the present invention can be used as a prophylactic/therapeutic agent for diseases attributable to overexpression of FPRL1 or FPRL2 or an excess of humanin.

Where the antisense DNA for example is used, the antisense DNA itself is inserted into an appropriate vector such as retrovirus vector, adenovirus vector, adenovirus-associated virus vector, etc. and then administered in a conventional manner. The antisense DNA itself is administered; alternatively, the antisense DNA is inserted into an appropriate vector such as retrovirus vector, adenovirus vector, adenovirus-associated virus vector, etc. and then administered in a conventional manner. The antisense DNA of the present invention may also be administered as naked DNA, or with adjuvants to assist its uptake by gene gun or through a catheter such as a catheter with a hydrogel.

Further, the antisense DNA can also be used as a diagnostic oligonucleotide probe for examining the presence of the DNA of the present invention in tissues or cells or its expression.

(11) Creation of an Animal Having the DNA of the Present Invention Introduced into it The present invention provides a non-human mammal having the DNA encoding the protein of the present invention, which is exogenous (hereinafter simply referred to as the exogenous DNA of the present invention) or its mutant DNA (sometimes simply referred to as the exogenous mutant DNA of the present invention).

Thus, the present invention provides:

[1] a non-human mammal having the exogenous DNA of the present invention or its mutant DNA;

[2] the mammal according to [1], wherein the non-human mammal is a rodent;

[3] the mammal according to [2], wherein the rodent is a mouse or rat; and

[4] a recombinant vector comprising the exogenous DNA of the present invention or its mutant DNA and capable of expression in a mammal.

The non-human mammal having the exogenous DNA of the present invention or its mutant DNA (hereinafter simply referred to as the DNA transgenic animal of the present invention) can be created by transfecting the desired DNA into an unfertilized egg, a fertilized egg, a spermatozoon, a germinal cell containing a primordial germinal cell thereof, or the like, preferably in the embryogenic stage in the development of a non-human mammal (more preferably in the single cell or fertilized cell stage and generally before the 8-cell phase) by standard means such as the calcium phosphate method, the electric pulse method, the lipofection method, the agglutination method, the microinjection method, the particle gun method, the DEAE-dextran method, etc. Also, it is possible to transfect the exogenous DNA of the present invention into a somatic cell, a living organ, a tissue cell or the like, by the DNA transfection methods, and utilize the transformant for cell culture, tissue culture, etc. In addition, these cells may be fused with the above-described germinal cell by a publicly known cell fusion method to create the transgenic animal of the present invention.

Examples of the non-human mammal that can be used include bovine, swine, sheep, goat, rabbits, dogs, cats, guinea pigs, hamsters, mice, rats and the like. Above all, preferred are rodents, especially mice (e.g., C57BL/6 strain, DBA2 strain, etc. for a pure line and for a cross line, B6C3F$_1$ strain, BDF$_1$ strain, B6D2F$_1$ strain, BALB/c strain, ICR strain, etc.) or rats (Wistar, SD, etc.) and the like, since they are relatively short in ontogeny and life cycle from a standpoint of creating model disease animals, and are easy in breeding.

"Mammals" in a recombinant vector that can be expressed in mammals include human etc. in addition to the aforesaid non-human mammals.

The exogenous DNA of the present invention refers to the DNA of the present invention that is once isolated and extracted from mammals, not the DNA of the present invention inherently possessed by the non-human mammals.

The mutant DNA of the present invention includes mutants resulting from variation (e.g., mutation, etc.) in the nucleotide sequence of the original DNA of the present invention, specifically DNAs resulting from base addition, deletion, substitution with other bases, etc. and further including abnormal DNA.

The abnormal DNA is intended to mean the DNA that expresses abnormal FPRL1 or FPRL2 of the present invention and exemplified by such a DNA that expresses FPRL1 or FPRL2 suppressing the functions of normal FPRL1 or FPRL2 of the present invention, or the like.

The exogenous DNA of the present invention may be any one of those derived from a mammal of the same species as, or a different species from, the mammal as the target animal. In transfecting the DNA of the present invention to the target animal, it is generally advantageous to use the DNA as a DNA construct in which the DNA is ligated downstream from a promoter capable of expressing the DNA in the target animal. For example, in the case of transfecting the human DNA of the present invention, a DNA transgenic mammal that expresses the DNA of the present invention to a high level can be prepared by microinjecting a DNA construct (e.g., vector, etc.) ligated with the human DNA of the present invention into a fertilized egg of the target mammal, e.g., a fertilized egg of mouse, downstream from the various promoters capable of expressing the DNA derived from various mammals (e.g., rabbits, dogs, cats, guinea pigs, hamsters, rats, mice, etc.) having the DNA of the present invention highly homologous to the human DNA.

As expression vectors for FPRL1 or FPRL2 of the present invention, there are *Escherichia coli*-derived plasmids, *Bacillus subtilis*-derived plasmids, yeast-derived plasmids, bacteriophages such as λ phage, etc., retroviruses such as Moloney leukemia virus, etc., animal viruses such as vaccinia virus, baculovirus, etc. Of these vectors, *Escherichia coli*-derived plasmids, *Bacillus subtilis*-derived plasmids, yeast-derived plasmids, etc. are preferably used.

Examples of these promoters for regulating the DNA expression include (i) promoters for DNA derived from viruses (e.g., simian virus, cytomegalovirus, Moloney leukemia virus, JC virus, breast cancer virus, poliovirus, etc.), and (ii) promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein glutathione S-transferase, platelet-derived growth factor β, keratins K1, K10 and K14, collagen types I and II, cyclic AMP-dependent protein kinase βI subunit, dystrophin, tartarate-resistant alkaline phosphatase, atrial natriuretic factor, endothelial receptor tyrosine kinase (generally abbreviated as Tie2), sodium-potassium adenosine triphosphorylase (Na, K-ATPase), neurofilament light chain, metallothioneins I and IIA, metalloproteinase 1 tissue inhibitor, MHC class I antigen (H-2L), H-ras, renin, dopamine β-hydroxylase, thyroid peroxidase (TPO), polypeptide chain elongation factor 1α (EF-1α), β actin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle a actin, preproencephalin A, vasopressin, etc. Among them, cytomegalovirus promoters, human peptide elongation factor 1α (EF-1α) promoters, human and chicken β actin promoters etc., which can achieve high expression in the whole body, are preferred.

It is preferred that the vectors described above have a sequence for terminating the transcription of the desired messenger RNA in the DNA transgenic animal (generally called a terminator); for example, a sequence of each DNA derived from viruses and various mammals. SV40 terminator of the simian virus, etc. are preferably used.

In addition, for the purpose of increasing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The normal translational region of FPRL1 or FPRL2 of the present invention can be prepared as the whole or a part of genomic DNA from DNA derived from liver, kidney, thyroid cells, fibroblasts etc. derived from humans or mammals (for example, rabbit, dog, cat, guinea pig, hamster, rat, mouse etc.) and a wide variety of commercial DNA libraries, or from complementary DNA as a starting material prepared by a known method from RNA derived from liver, kidney, thyroid cells, fibroblasts etc. As the extraneous abnormal DNA, a translational region can be prepared by point mutation of the normal translational region of FPRL1 or FPRL2 obtained from the above cells or tissues.

The translational region can be prepared, as a DNA construct capable of being expressed in the transgenic animal, by a conventional DNA engineering technique, in which the DNA is ligated downstream from the aforesaid promoter and if desired, upstream from the translation termination site.

The exogenous DNA of the present invention is transfected at the fertilized egg cell stage in a manner such that the DNA is certainly present in all the germinal cells and somatic cells of the target mammal. The fact that the exogenous DNA of the present invention is present in the germinal cells of the animal prepared by DNA transfection means that all offspring of the prepared animal will maintain the exogenous DNA of the present invention in all of the germinal cells and somatic cells thereof. The offspring of the animal that inherits the exogenous DNA of the present invention also have the exogenous DNA of the present invention in all of the germinal cells and somatic cells thereof.

The non-human mammal, in which the normal exogenous DNA of the present invention has been transfected, can be passaged as the DNA-bearing animal under ordinary rearing environment, by confirming that the exogenous DNA is stably retained by mating.

By the transfection of the exogenous DNA of the present invention at the fertilized egg cell stage, the DNA is retained to be excess in all of the germinal and somatic cells of the target mammal. The fact that the exogenous DNA of the present invention is excessively present in the germinal cells of the prepared animal after transfection means that all of the offspring of the animal prepared have the exogenous DNA of the present invention excessively in all of the germinal cells and somatic cells thereof. The offspring of the animal of this kind that inherits the exogenous DNA of the present invention excessively have the DNA of the present invention in all of the germinal cells and somatic cells thereof.

By obtaining a homozygotic animal having the transfected DNA in both of homologous chromosomes and mating a male and female of the animal, all offspring can be passaged to excessively retain the DNA.

In a non-human mammal bearing the normal DNA of the present invention, the normal DNA of the present invention is expressed to a high level, and may eventually develop the hyperfunction of FPRL1 or FPRL2 of the present invention by promoting the functions of endogenous normal DNA. Therefore, the animal can be utilized as a pathologic model animal for such a disease. Specifically, using the normal DNA transgenic animal of the present invention, it becomes possible to elucidate the hyperfunction of FPRL1 or FPRL2 of the present invention and to clarify the pathological mechanism of the disease associated with FPRL1 or FPRL2 of the present invention and to determine how to treat these diseases.

Furthermore, since a mammal transfected with the exogenous normal DNA of the present invention exhibits an increasing symptom of FPRL1 or FPRL2 of the present invention, the animal is usable for screening of therapeutic agents for the disease associated with FPRL1 or FPRL2 of the present invention.

On the other hand, non-human mammal having the exogenous abnormal DNA of the present invention can be passaged under normal breeding conditions as the DNA-bearing animal by confirming the stable retaining of the exogenous DNA via crossing. In addition, the objective exogenous DNA can be utilized as a starting material by inserting the objective exogenous DNA into the plasmid described above. The DNA construct with a promoter can be prepared using conventional DNA engineering techniques. The transfection of the abnormal DNA of the present invention at the fertilized egg cell stage is preserved to be present in all of the germinal and somatic cells of the mammals to be targeted. The fact that the abnormal DNA of the present invention is present in the germinal cells of the animal after DNA transfection means that all of the offspring of the prepared animal have the abnormal DNA of the present invention in all of the germinal and somatic cells. The offspring of such an animal that inherits the exogenous DNA of the present invention has the abnormal DNA of the present invention in all the germinal and somatic cells. A homozygous animal having the introduced DNA on both of homologous chromosomes can be acquired and then by mating these male and female animals, all the offspring can be bred to have the DNA.

Since the non-human mammal having the abnormal DNA of the present invention expresses the abnormal DNA of the present invention at a high level, the animal may cause the function inactive type inadaptability of FPRL1 or FPRL2 of the present invention by inhibiting the functions of the endogenous normal DNA, and can be utilized as its disease model animal. For example, using the abnormal DNA-transferred animal of the present invention, it is possible to elucidate the mechanism of the function inactive type inadaptability of FPRL1 or FPRL2 of the present invention and to study a method for treatment of this disease.

In its specific applicability, the transgenic animal of the present invention expressing the abnormal DNA of the present invention to a high level is also expected to serve as a model for the elucidation of the mechanism of the functional inhibition (dominant negative effect) of normal FPRL1 or FPRL2 by abnormal FPRL1 or FPRL2 of the present invention in the function inactive type inadaptability of FPRL1 or FPRL2 of the present invention.

A mammal bearing the abnormal exogenous DNA of the present invention is also expected to serve for screening a candidate drug for the treatment of the function inactive type inadaptability of FPRL1 or FPRL2 of the present invention, since FPRL1 or FPRL2 of the present invention is increased in such an animal.

Other potential applications of two kinds of the DNA transgenic animals of the present invention described above further include:

(1) Use as a cell source for tissue culture, (2) Elucidation of the relation to FPRL1 or FPRL2 that is specifically expressed or activated by FPRL1 or FPRL2 of the present invention, by direct analysis of DNA or RNA in tissues of the DNA transgenic animal of the present invention or by analysis of the FPRL1 or FPRL2 tissues expressed by the DNA, (3) Research on the function of cells derived from tissues that are usually cultured only with difficulty, using cells in tissues bearing the DNA cultured by a standard tissue culture technique, (4) Screening a drug that enhances the functions of cells using the cells described in (3) above, and (5) Isolation and purification of mutant FPRL1 or FPRL2 of the present invention and preparation of an antibody thereto.

Furthermore, clinical conditions of a disease associated with FPRL1 or FPRL2 of the present invention, including the function inactive type inadaptability to FPRL1 or FPRL2 of the present invention, can be examined by using the DNA transgenic animal of the present invention. Also, pathological findings on each organ in a disease model associated with FPRL1 or FPRL2 of the present invention can be obtained in more detail, leading to the development of a new method for treatment as well as the research and therapy of any secondary diseases associated with the disease.

It is also possible to obtain a free DNA-transfected cell by withdrawing each organ from the DNA transgenic animal of the present invention, mincing the organ and degrading with a proteinase such as trypsin, etc., followed by establishing the line of culturing or cultured cells. Furthermore, the DNA transgenic animal of the present invention can serve to identify cells capable of producing FPRL1 or FPRL2 of the present invention, and to study in association with apoptosis, differentiation or propagation or on the mechanism of signal transduction in these properties to inspect any abnormality therein. Thus, the DNA transgenic animal can provide an effective research material for FPRL1 or FPRL2 of the present invention and for investigation of the function and effect thereof.

To develop a drug for the treatment of diseases associated with FPRL1 or FPRL2 of the present invention, including the function inactive type inadaptability to FPRL1 or FPRL2 of the present invention, using the DNA transgenic animal of the present invention, an effective and rapid method for screening a drug for the treatment of the diseases can be provided by using the method for inspection, the method for quantification etc. described above. It is also possible to investigate and develop a method for DNA therapy for the treatment of diseases associated with FPRL1 or FPRL2 of the present invention, using the DNA transgenic animal of the present invention or a vector capable of expressing the exogenous DNA of the present invention.

(12) Knockout Animal

The present invention provides a non-human mammal embryonic stem cell bearing the DNA of the present invention inactivated and a non-human mammal deficient in expressing the DNA of the present invention.

Thus, the present invention provides:

[1] a non-human mammal embryonic stem cell in which the DNA of the present invention is inactivated;

[2] the embryonic stem cell according to [1], wherein the DNA is inactivated by introducing a reporter gene (e.g., β-galactosidase gene derived from *Escherichia coli*);

[3] the embryonic stem cell according to [1], which is resistant to neomycin;

[4] the embryonic stem cell according to [1], wherein the non-human mammal is a rodent;

[5] an embryonic stem cell according to [4], wherein the rodent is a mouse;

[6] a non-human mammal deficient in expressing the DNA of the present invention, wherein the DNA of the present invention is inactivated;

[7] the non-human mammal according to [6], wherein the DNA is inactivated by inserting a reporter gene (e.g., β-galactosidase derived from *Escherichia coli*) therein and the reporter gene is capable of being expressed under the control of a promoter for the DNA of the present invention;

[8] the non-human mammal according to [6], which is a rodent;

[9] the non-human mammal according to [8], wherein the rodent is a mouse; and

[10] a method for screening a compound or its salt that promotes or inhibits the promoter activity for the DNA of the present invention, which comprises administering a test compound to the animal of [7] and detecting expression of the reporter gene.

The non-human mammalian embryonic stem cell, in which the DNA of the present invention is inactivated, refers to a non-human mammalian embryonic stem cell that suppresses the ability of the non-human mammalian to express the DNA by artificially mutating the DNA of the present invention possessed in the non-human mammal, or the DNA has no substantial ability to express FPRL1 or FPRL2 of the present invention (hereinafter sometimes referred to as the knockout DNA of the present invention) by substantially inactivating the activities of FPRL1 or FPRL2 of the present invention encoded by the DNA (hereinafter merely referred to as ES cell).

As the non-human mammalian, the same examples as described above apply.

Techniques for artificially mutating the DNA of the present invention include deletion of a part or all of the DNA sequence and insertion of, or substitution with, other DNA, e.g., by genetic engineering. By these mutations, the knockout DNA of the present invention may be prepared, for example, by shifting the reading frame of a codon or by destroying the function of a promoter or exon.

Specifically, the non-human mammalian embryonic stem cell in which the DNA of the present invention is inactivated (hereinafter merely referred to as the ES cell with the DNA of the present invention inactivated or the knockout ES cell of the present invention) can be obtained by, for example, isolating the DNA of the present invention possessed by the target non-human mammal, inserting a DNA strand (hereinafter simply referred to as targeting vector) having a DNA sequence constructed so as to eventually destroy the gene by inserting into its exon site a chemical resistant gene such as a neomycin resistant gene or a hygromycin resistant gene, or a reporter gene such as lacZ (β-galactosidase gene) or cat (chloramphenicol acetyltransferase gene), etc. thereby destroying the functions of exon, or by inserting into the intron site between exons a DNA sequence which terminates gene transcription (e.g., polyA-added signal, etc.) thereby disabling the synthesis of complete messenger RNA, into a chromosome of the animal cells by, e.g., homologous recombination. The thus obtained ES cells are analyzed by the Southern hybridization using as a probe a DNA sequence on or near the DNA of the present invention, or by PCR using as primers a DNA sequence on the targeting vector and another DNA sequence near the DNA of the present invention which is not included in the targeting vector, and the knockout ES cell of the present invention is selected.

The parent ES cells to inactivate the DNA of the present invention by homologous recombination, etc. may be of a strain already established as described above, or may be originally established in accordance with a modification of the known method by Evans and Kaufman. For example, in the case of mouse ES cells, currently it is common practice to use ES cells of the 129 strain. However, since their immunological background is obscure, the C57BL/6 mouse or the BDF$_1$ mouse (F$_1$ hybrid between C57BL/6 and DBA/2), wherein the low ovum collection per C57BL/6 mouse or C57BL/6 has been improved by crossing with DBA/2, may be preferably used, instead of obtaining a pure line of ES cells with the clear immunological genetic background. The BDF$_1$ mouse is advantageous in that when a pathologic model mouse is generated using ES cells obtained therefrom, the genetic background can be changed to that of the C57BL/6 mouse by back-crossing with the C57BL/6 mouse, since its background is of the C57BL/6 mouse, as well as being advantageous in that ovum availability per animal is high and ova are robust.

In establishing ES cells, blastocytes of 3.5 days after fertilization are commonly used. A large number of early stage embryos may be acquired more efficiently, by collecting the embryos of the 8-cell stage and using the same after culturing until the blastocyte stage.

Although the ES cells used may be of either sex, male ES cells are generally more convenient for generation of a germ cell line chimera and are therefore preferred. It is desirable to identify sexes as soon as possible also in order to save painstaking culture time.

As an example of the method for sex identification of the ES cell, mention may be made of a method in which a gene in the sex-determining region on the Y-chromosome is amplified by PCR and detected. When this method is used, ES cells (about 50 cells) corresponding to almost 1 colony are sufficient, whereas karyotype analysis hitherto required about $10^6$ cells; therefore, the first selection of ES cells at the early stage of culture can be based on sex identification, and male cells can be selected early, which saves a significant amount of time at the early stage of culture.

Second selection can be achieved by, for example, chromosome number confirmation by the G-banding method. It is usually desirable that the chromosome number of the obtained ES cells be 100% of the normal number. However, when it is difficult to obtain the cells having the normal number of chromosomes due to physical operation etc. in cell establishment, it is desirable that the ES cell be again cloned to a normal cell (e.g., in mouse cells having the number of chromosomes being 2n=40) after the gene of the ES cells is rendered knockout.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably about 5% carbon dioxide and about 95% air, or about 5% oxygen, about 5% carbon dioxide and about 90% air) in the presence of LIF (1–10000 U/ml) on appropriate feeder cells such as STO fibroblasts, treated with a trypsin/EDTA solution (normally about 0.001 to about 0.5% trypsin/about 0.1 to 5 mM EDTA, preferably about 0.1% trypsin/about 1 mM EDTA) at the time of passage to obtain separate single cells, which are then seeded on freshly prepared feeder cells. This passage is normally conducted every 1 to 3 days; it is desirable that cells be observed at passage and cells found to be morphologically abnormal in culture, if any, be abandoned.

By allowing ES cells to reach a high density in monolayers or to form cell aggregates in suspension under appropriate conditions, it is possible to differentiate them to various cell types, for example, parietal and visceral muscles, cardiac muscle or the like [M. J. Evans and M. H. Kaufman, Nature, 292, 154, 1981; G R. Martin, Proc. Natl. Acad. Sci. U.S.A., 78, 7634, 1981; T. C. Doetschman et al., Journal of Embryology Experimental Morphology, 87, 27, 1985]. The cells deficient in expression of the DNA of the present invention, which are obtainable from the differentiated ES cells of the present invention, are useful for studying the functions of FPRL1 or FPRL2 of the present invention or FPRL1 or FPRL2 of the present invention in vitro cytologically or molecular biologically.

The non-human mammal deficient in expression of the DNA of the present invention can be identified from a normal animal by measuring the amount of mRNA in the subject animal by a publicly known method, and indirectly comparing the levels of expression.

As the non-human mammal, the same examples supra apply.

With respect to the non-human mammal deficient in expression of the DNA of the present invention, the DNA of the present invention can be made knockout by transfecting a targeting vector, prepared as described above, to mouse embryonic stem cells or mouse oocytes thereof, and conducting homologous recombination in which a targeting vector DNA sequence, wherein the DNA of the present invention is inactivated by the transfection, is replaced with the DNA of the present invention on a chromosome of a mouse embryonic stem cell or mouse oocyte.

The cells with the DNA of the present invention in which the DNA of the present invention is rendered knockout can be identified by the Southern hybridization analysis using as a probe a DNA sequence on or near the DNA of the present invention, or by PCR analysis using as primers a DNA sequence on the targeting vector and another DNA sequence which is not included in the DNA of the present invention derived from mouse, which is used as the targeting vector. When non-human mammalian embryonic stem cells are used, the cell line wherein the DNA of the present invention is inactivated is cloned by homologous recombination; the resulting cloned cell line is injected to, e.g., a non-human mammalian embryo or blastocyte, at an appropriate stage such as the 8-cell stage. The resulting chimeric embryos are transplanted to the uterus of the pseudo-pregnant non-human mammal. The resulting animal is a chimeric animal composed of both cells having the normal locus of the DNA of the present invention and those having an artificially mutated locus of the DNA of the present invention.

When some germ cells of the chimeric animal have a mutated locus of the DNA of the present invention, an individual in which all tissues are composed of cells having an artificially mutated locus of the DNA of the present invention can be selected from a series of offspring obtained by crossing between such a chimeric animal and a normal animal, e.g., by coat color identification, etc. The individuals thus obtained are normally deficient in heterozygous expression of FPRL1 or FPRL2 of the present invention. The individuals deficient in homozygous expression of FPRL1 or FPRL2 of the present invention can be obtained from offspring of the intercross between the heterozygotes.

When an oocyte is used, a DNA solution may be injected, e.g., to the prenucleus by microinjection thereby obtaining a transgenic non-human mammal having a targeting vector introduced into its chromosome. From such transgenic non-human mammals, those having a mutation at the locus of the DNA of the present invention can be obtained by selection based on homologous recombination.

As described above, individuals wherein the DNA of the present invention is rendered knockout permit passage rearing under ordinary rearing conditions, after it is confirmed that in the animal individuals obtained by their crossing, the DNA has been knockout.

Furthermore, the genital system may be obtained and maintained by conventional methods. That is, by crossing male and female animals each having the inactivated DNA, homozygote animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammalian embryonic stem cell, in which the DNA of the present invention is inactivated, is very useful for preparing a non-human mammal deficient in expression of the DNA of the present invention.

Since the non-human mammal, in which the DNA of the present invention fails to express, lacks various biological activities induced by FPRL1 or FPRL2 of the present invention, such an animal can be a disease model suspected of inactivated biological activities of FPRL1 or FPRL2 of the present invention and thus, offers an effective study to investigate causes for and therapy for these diseases.

(12a) Method for Screening of Compounds Having Therapeutic/Prophylactic Effects for Diseases Caused by Deficiency, Damages, etc. of the DNA of the Present Invention The non-human mammal deficient in expression of the DNA of the present invention can be used to screen compounds having therapeutic/prophylactic effects for diseases caused by deficiency, damages, etc. of the DNA of the present invention.

That is, the present invention provides a method for screening of a compound or its salt having therapeutic/prophylactic effects for diseases caused by deficiency, damages, etc. of the DNA of the present invention, which comprises administering a test compound to the non-human mammal deficient in expression of the DNA of the present invention, and observing and measuring a change having occurred in the animal.

As the non-human mammal deficient in expression of the DNA of the present invention used for the screening method, the same examples as given hereinabove apply.

Examples of the test compounds include peptides, proteins, non-peptide compounds, synthetic compounds, fermentation products, cell extracts, plant extracts, animal tissue extracts, blood plasma, etc. and these compounds may be novel compounds or publicly known compounds.

The test compounds may form salts, and as salts of the test compounds, use is made of salts with physiologically acceptable acids (e.g., inorganic acids etc.) or bases (e.g., organic acids [sic] etc.), preferably physiologically acceptable acid addition salts. Examples of such salts are salts with inorganic acids (e.g., hydrochloric acid, phosphoric acid, hydrobromic acid, sulfuric acid etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid etc.) and the like.

Specifically, the non-human mammal deficient in the expression of the DNA of the present invention is treated with a test compound, comparison is made with an intact animal for control and a change in each organ, tissue, disease conditions, etc. of the animal is used as an indicator to assess the therapeutic/prophylactic effects of the test compound.

For treating an animal to be tested with a test compound, for example, oral administration, intravenous injection, etc. are applied and the treatment is appropriately selected depending upon conditions of the test animal, properties of the test compound, etc. Furthermore, the amount of a test compound administered can be appropriately selected depending on administration route, nature of the test compound, or the like.

In the screening method, when the Alzheimer's disease symptom of a test animal is ameliorated by about 10% or more, preferably about 30% or more, more preferably about 50% or more by administering a test compound to the test animal, the test compound can be selected as a compound or its salt that has therapeutic/prophylactic effects on the disease.

The compound or its salt obtained by the screening method is a compound or its salt selected from the test compounds, and can be used for example as a low toxic and safe pharmaceutical preparation such as a prophylactic/therapeutic agent for diseases caused by deficiency in or damage to FPRL1 or FPRL2 of the present invention (for example, diseases involving nerve degeneration, for example, nerve degeneration diseases (for example, Alzheimer's disease [familial Alzheimer's disease, early-onset Alzheimer's disease, sporadic Alzheimer's disease etc.], Parkinson's disease, Down's syndrome, amyotrophic lateral sclerosis, prion disease, Creutzfeldt-Jakob disease, Huntington's disease, diabetic neuropathy, multiple sclerosis etc.), brain function disorders (for example, cerebral infarction, cerebral hemorrhage, subarachnoid hemorrhage, ischemic cerebral disease, epidural hematoma, subdural hematoma etc.), cancers (for example, astrocytoma, oligodendrocytoma etc.), immune diseases, infection diseases (for example, meningitis, protozoan infection, rickettia infection, protozoa metazoan infection, bacterial or viral meningitis such as Borna disease, encephalitis after vaccine inoculation, dementia associated with AIDS, etc.), alimentary diseases, circulatory diseases, endocrine diseases etc.). Further, a compound derived from the compound obtained by the screening can also be similarly used.

The compound obtained by the screening method may form a salt, and as the salts of the compound, there may be used salts with physiologically acceptable acids (e.g., inorganic acids or organic acids) or bases (e.g., alkali metals), preferably physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

A pharmaceutical preparation comprising the compound or salts thereof obtained by the above screening method may be manufactured in a manner similar to the above-described method for preparing the pharmaceutical preparation comprising the compound or a salt thereof changing the binding property or signal transduction between FPRL1 or FPRL2 of the present invention and humanin.

Since the pharmaceutical preparation thus obtained is safe and low toxic, it can be administered to humans or other mammals (e.g., rat, mouse, guinea pig, rabbit, sheep, swine, bovine, horse, cat, dog, monkey, etc.).

The dose of the above compound or its salt may vary depending on target disease, subject to be administered, route for administration, etc. When the compound is orally administered, the compound is administered to a patient with Alzheimer's disease (as 60 kg) generally in a daily dose of approximately 0.1 to 100 mg, preferably approximately 1.0 mg to 50 mg, more preferably approximately 1.0 to 20 mg. When the compound is parenterally administered, a single dose of the compound may vary depending on subject to be administered, target disease, etc. When the compound is administered in the form of an injection to a patient with Alzheimer's disease (as 60 kg), it is convenient to administer the compound by intravenous injection generally in a daily dose of approximately 0.01 to 30 mg, preferably approximately 0.1 to 20 mg, more preferably approximately 0.1 to 10 mg. For other animal species, the corresponding dose as converted per 60 kg weight can be administered.

(12b) Method of Screening a Compound that Promotes or Inhibits the Activities of a Promoter for the DNA of the Present Invention The present invention provides a method of screening a compound or its salt that promotes or inhibits the activities of a promoter for the DNA of the present invention, which comprises administering a test compound to a non-human mammal deficient in expression of the DNA of the present invention and detecting expression of the reporter gene.

In the screening method described above, the non-human mammal deficient in expression of the DNA of the present invention is selected from the aforesaid non-human mammals deficient in expression of the DNA of the present invention in which the DNA of the present invention is inactivated by introducing a reporter gene and the reporter gene can be expressed under the control of a promoter for the DNA of the present invention.

The same examples given above for the test compound apply to the test compound.

As the reporter gene, the same specific examples given above apply to the reporter gene, with β-galactosidase (lacZ), soluble alkaline phosphatase gene, luciferase gene, etc. being preferred.

In the non-human mammal deficient in expression of the DNA of the present invention wherein the DNA of the present invention is replaced by a reporter gene, the reporter gene is present under the control of a promoter for the DNA of the present invention. Thus, the activity of the promoter can be detected by tracing the expression of a substance encoded by the reporter gene.

For example, when a part of the DNA region encoding FPRL1 or FPRL2 of the present invention is replaced by, e.g., β-galactosidase gene (lacZ) derived from *Escherichia coli*, β-galactosidase is expressed in a tissue where FPRL1 or FPRL2 of the present invention should originally be expressed, in place of FPRL1 or FPRL2 of the present invention. Thus, the expression state of FPRL1 or FPRL2 of the present invention can be readily observed in vivo in an animal, by staining with a reagent, e.g., 5-bromo-4-chloro-3-indolyl-β-galactopyranoside (X-gal), which is a substrate for β-galactosidase. Specifically, a mouse deficient in FPRL1 or FPRL2 of the present invention, or its tissue section, is fixed with glutaraldehyde, etc. After washing with phosphate buffered saline (PBS), the system is reacted with a staining solution containing X-gal at room temperature or about 37° C. for approximately 30 minutes to 1 hour. After the β-galactosidase reaction is terminated by washing the tissue preparation with 1 mM EDTA/PBS solution, the color formed is observed. Alternatively, mRNA encoding lacZ may be detected in a conventional manner.

The compound or salts thereof obtained using the screening methods supra are compounds (or their salts) selected from the test compounds described above, which promote or inhibit the promoter activity for the DNA of the present invention.

As the salts of the compounds obtained by the screening methods, use is made of salts with physiologically acceptable acids (e.g., inorganic acids) or bases (e.g., organic acids [sic]), and physiologically acceptable acid addition salts are preferred. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The compound or its salt that promotes the promoter activity for the DNA of the present invention can promote the expression of FPRL1 or FPRL2 of the present invention to promote the functions of the FPRL1 or FPRL2, and can thus be used as a pharmaceutical preparation such as a prophylactic/therapeutic agent for diseases associated with dysfunction of FPRL1 or FPRL2 of the present invention. Specifically, the compound or its salt can be used for example as an apotosis inhibitor and as a low toxic and safe pharmaceutical preparation such as a prophylactic/therapeutic agent for diseases involving nerve degeneration, for example, nerve degeneration diseases (for example, Alzheimer's disease [familial Alzheimer's disease, early-onset Alzheimer's disease, sporadic Alzheimer's disease etc.], Parkinson's disease, Down's syndrome, amyotrophic lateral sclerosis, prion disease, Creutzfeldt-Jakob disease, Huntington's disease, diabetic neuropathy, multiple sclerosis etc.), brain function disorders (for example, cerebral infarction, cerebral hemorrhage, subarachnoid hemorrhage, ischemic cerebral disease, epidural hematoma, subdural hematoma etc.), cancers (for example, astrocytoma, oligodendrocytoma etc.), immune diseases, infection diseases (for example, meningitis, protozoan infection, rickettia infection, protozoa metazoan infection, bacterial or viral meningitis such as Borna disease, encephalitis after vaccine inoculation, dementia associated with AIDS, etc.), alimentary diseases, circulatory diseases, endocrine diseases etc., preferably as a prophylactic/therapeutic agent for nerve degeneration diseases and brain function disorders, more preferably as a prophylactic/therapeutic agent for Alzheimer's disease.

The compound or its salt that inhibits the promoter activity for the DNA of the present invention can inhibit the expression of FPRL1 or FPRL2 of the present invention to inhibit the functions of the FPRL1 or FPRL2, and is thus useful as a pharmaceutical preparation such as a prophylactic/therapeutic agent for diseases associated with excessive secretion of FPRL1 or FPRL2 of the present invention.

Further, a compound derived from the compound obtained in the above screening can also be used similarly.

The pharmaceutical preparation comprising the compound or its salt obtained by the screening method can be produced in a manner similar to the method for preparing the pharmaceutical preparation comprising the compound changing the binding property between FPRL1 or FPRL2 of the present invention and humanin described hereinabove.

The thus obtained pharmaceutical preparation is safe and low toxic, and can thus be administered to, for example, humans and mammals (e.g., rat, mouse, guinea pig, rabbit, sheep, swine, bovine, horse, cat, dog, monkey, etc.).

The dose of the compound or its salt may vary depending on target disease, subject to be administered, route for administration, etc. When the compound promoting the promoter activity for the DNA of the present invention is orally administered, the compound is administered to a patient with Alzheimer's disease (as 60 kg) generally in a daily dose of approximately 0.1 to 100 mg, preferably approximately 1.0 mg to 50 mg, more preferably approximately 1.0 to 20 mg. When the compound is parenterally administered, a single dose of the compound may vary depending on subject to be administered, target disease, etc. When the compound (or its salt) promoting the promoter activity for the DNA of the present invention is administered in the form of an injection to a patient with Alzheimer's disease (as 60 kg), it is convenient to administer the compound or its salt by intravenous injection in a daily dose of approximately 0.01 to 30 mg, preferably approximately 0.1 to 20 mg, more preferably approximately 0.1 to 10 mg. For other animal species, the corresponding dose as converted per 60 kg weight can be administered.

Thus, the non-human mammal deficient in expression of the DNA of the present invention is extremely useful in screening a compound or its salt that promotes or inhibits the activity of a promoter for the DNA of the present invention, and can contribute significantly to elucidation of causes for various diseases attributable to deficient expression of the DNA of the present invention or development of a prophylactic/therapeutic agent for the diseases.

Further, genes encoding various proteins are ligated downstream from DNA containing a promoter region for FPRL1 or FPRL2 of the present invention and injected into a fertilized egg of an animal to create a transgenic animal by which FPRL1 or FPRL2 of the present invention can be specifically synthesized and examined for its action in the living body. When a suitable reporter gene is ligated to the promoter region to establish a cell strain expressing the same, the cell strain can be used as a system of searching for a low-molecular compound having an action of specifically promoting or suppressing the ability of the cell strain to produce FPRL1 or FPRL2 of the present invention in vivo.

In the specification and drawings, the codes of bases and amino acids are denoted in accordance with the IUPAC-IUB Commission on Biochemical Nomenclature or by the common codes in the art, examples of which are shown below. For amino acids that may have the optical isomer, L form is presented unless otherwise indicated.

DNA: deoxyribonucleic acid
cDNA: complementary deoxyribonucleic acid
A: adenine
T: thymine
G: guanine
C: cytosine
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediaminetetraacetic acid
SDS: sodium dodecyl sulfate
Gly: glycine
Ala: alanine
Val: valine
Leu: leucine
Ile: isoleucine
Ser: serine
Thr: threonine
Cys: cysteine
Met: methionine
Glu: glutamic acid
Asp: aspartic acid
Lys: lysine
Arg: arginine
His: histidine
Phe: phenylalanine
Tyr: tyrosine
Trp: tryptophan
Pro: proline
Asn: asparagine
Gln: glutamine
pGlu: pyroglutamic acid
*: termination codon
Me: methyl
Et: ethyl
Bu: butyl
Ph: phenyl
TC: thiazolidine-4(R)-carboxamide The substituents, protective groups and reagents, which are frequently used throughout the specification, are shown by the following abbreviations.

Tos: p-toluenesulfonyl
CHO: formyl
Bzl: benzyl
Cl$_2$Bzl: 2,6-benzyloxycarbonyl
Bom: benzyloxymethyl
Z: benzyloxycarbonyl
Cl-Z: 2-chlorobenzyloxycarbonyl
Br-Z: 2-bromobenzyloxycarbonyl
Boc: t-butoxycarbonyl
DNP: dinitrophenol
Trt: trityl
Bum: t-butoxymethyl
Fmoc: N-9-fluorenylmethoxycarbonyl
HOBt: 1-hydroxybenztriazole
HOOBt: 3,4-dihydro-3-hydroxy-4-oxo-1,2,3-benzotriazine
HONB: 1-hydroxy-5-norbornene-2,3-dicarboxyimide
DCC: N,N'-dicyclohexylcarbodiimide The sequence identification numbers in the sequence listing of the present specification indicate the following sequences, respectively.

SEQ ID NO: 1 shows the amino acid sequence of human-derived FPRL1.

SEQ ID NO: 2 shows the nucleotide sequence of cDNA encoding human-derived FPRL1.

SEQ ID NO: 3 shows the amino acid sequence of human humanin (1-24).

SEQ ID NO: 4 shows the amino acid sequence of [Gly$^{14}$]-human humanin (1-24).

SEQ ID NO: 5 shows the amino acid sequence of a humanin analogous peptide.

SEQ ID NO: 6 shows the amino acid sequence of human humanin (1-21).

SEQ ID NO: 7 shows the amino acid sequence of rat humanin (1-38).

SEQ ID NO: 8 shows the amino acid sequence of rat humanin (1-24).

SEQ ID NO: 9 shows the amino acid sequence of rat humanin (1-21).

SEQ ID NO: 10 shows the amino acid sequence of rat-derived FPRL1.

SEQ ID NO: 11 shows the nucleotide sequence of cDNA encoding rat-derived FPRL1.

SEQ ID NO: 12 shows the amino acid sequence of mouse-derived FPRL2 (FPRL1).

SEQ ID NO: 13 shows the nucleotide sequence of cDNA encoding mouse-derived FPRL2 (FPRL1).

SEQ ID NO: 14 shows the amino acid sequence of human-derived FPRL2.

SEQ ID NO: 15 shows the nucleotide sequence of cDNA encoding human-derived FPRL2.

SEQ ID NO: 16 shows the nucleotide sequence of primer 1 used in Reference Example 1.

SEQ ID NO: 17 shows the nucleotide sequence of primer 2 used in Reference Example 1.

SEQ ID NO: 18 shows the nucleotide sequence of primer 3 used in Reference Example 2.

SEQ ID NO: 19 shows the nucleotide sequence of primer 4 used in Reference Example 2.

SEQ ID NO: 20 shows the nucleotide sequence of primer 5 used in Reference Example 2.

SEQ ID NO: 21 shows the nucleotide sequence of primer 6 used in Reference Example 2.

SEQ ID NO: 22 shows the nucleotide sequence of primer 7 used in Reference Example 2.

SEQ ID NO: 23 shows the nucleotide sequence of primer 8 used in Reference Example 2.

SEQ ID NO: 24 shows the amino acid sequence of W-Peptide.

The transformant *Escherichia coli* JM 109/pCU 18-rF-PRL1 obtained in Reference Example 2 described below has been deposited since Jan. 10, 2003 under Accession No. FERM BP-8274 with International Patent Organisms Depository, National Institute of Advanced Industrial Science and Technology, located at Central 6, 1-1-1 Higashi, Tsukuba, Ibaraki Prefecture, 305-8566, Japan.

EXAMPLES

Hereinafter, the present invention is described in more detail by reference to the Examples, which however are not intended to limit the scope of the present invention. The gene manipulation procedures using *Escherichia coli* were performed according to the methods described in the Molecular Cloning.

Reference Example 1

Cloning of cDNA Encoding Mouse Spleen-Derived FPRL2 and Construction of an Expression Vector Using mouse spleen-derived cDNA (Marathon-Ready™ cDNA, Clontech) as a template and two primers designed on the basis of the sequence information of mouse FPRL2 (Accession #071180, NCBI), namely, primer 1 (SEQ ID NO: 16) and primer 2 (SEQ ID NO: 17), PCR was carried out. Using Pyrobest DNA polymerase (Takara Shuzo CO., LTD), the PCR reaction was carried out by (1) reaction at 98° C. for 1 minute, (2) 35 cycles each consisting of reaction at 98° C. for 10 seconds, at 55° C. for 30 seconds and at 72° C. for 60 seconds, and (3) extension reaction at 72° C. for 2 minutes. After the reaction, the amplified product was cleaved with restriction enzymes Sal I and Xba I and then inserted into plasmid vector pAKKO-111H to construct an expression vector. As a result of analysis of the nucleotide sequence thereof, a cDNA sequence (SEQ ID NO: 13) encoding mouse FPRL2 consisting of the amino acid sequence represented by SEQ ID NO: 12 was obtained.

Reference Example 2

Cloning of cDNA Encoding Rat Spleen-Derived FPRL1, Determination of its Nucleotide Sequence, and Construction of an Expression Vector From rat spleen mRNA, cDNA was synthesized by using Marathon™ cDNA Amplification Kit (Clontech), and an adapter was added to the terminal thereof. Using this cDNA as a template and two primers, namely, primer 3 (SEQ ID NO: 18) and primer 4 (SEQ ID NO: 19), PCR was carried out. Using Advantage 2 Polymerase mix (Clontech), the PCR reaction was carried out by (1) reaction at 96° C. for 1 minute, (2) 5 cycles each consisting of reaction at 96° C. for 10 seconds and at 72° C. for 2 minutes, (3) 5 cycles each consisting of reaction at 96° C. for 10 seconds and at 70° C. for 2 minutes, (4) 25 cycles each consisting of reaction at 96° C. for 10 seconds and at 68° C. for 2 minutes, and (5) extension reaction at 72° C. for 5 minutes. After the reaction, the amplified product was inserted into plasmid vector pCR2.1 TOPO (Invitrogen, Inc.) according to a protocol of TOPO TA Cloning Kit (Invitrogen, Inc.), and the resulting vector was cloned into *Escherichia coli* JM109 (Takara Shuzo CO., LTD). As a result of analysis for sequence of each clone, a cDNA sequence encoding a part of the novel G protein-coupled receptor protein was obtained. On the basis of this sequence information, two primers, namely, primer 5 (SEQ ID NO: 20) and primer 6 (SEQ ID NO: 21) were designed. Using the primers and the above cDNA as a template synthesized from rat spleen mRNA, 5'-RACE and 3'-RACE were carried out respectively according to a protocol of Marathon™ cDNA Amplification Kit (Clontech). The PCR was carried out in the same manner as above, and after the reaction, the amplified product was inserted into plasmid vector pCR2.1 TOPO (Invitrogen, Inc.) according to a protocol of TOPO TA Cloning Kit (Invitrogen, Inc.), and the resulting vector was cloned into *Escherichia coli* JM109 (Takara Shuzo CO., LTD). As a result of analysis for sequence of each clone, a cDNA sequence encoding a part of the novel G protein-coupled receptor protein was obtained. On the basis of this sequence information, two primers, namely, primer 7 (SEQ ID NO: 22) and primer 8 (SEQ ID NO: 23) were designed. Using the primers and the above cDNA as a template synthesized from rat spleen mRNA, PCR was carried out. Using Pyrobest DNA Polymerase (Takara Shuzo Co., Ltd.), the PCR reaction was carried out by (1) reaction at 96° C. for 1 minute, (2) 35 cycles each consisting of reaction at 98° C. for 10 seconds, at 55° C. for 30 seconds and at 72° C. for 60 seconds, and (3) extension reaction at 72° C. for 2 minutes. After the reaction, the amplified product was cleaved with restriction enzymes Sal I and Xba I and then inserted into plasmid vector pAKKO-111H to construct an expression vector. The inserted fragment was cut off by cleaving the expression vector with restriction enzymes Sal I and Nhe I and then inserted into plasmid vector pUC 119. As a result of analysis for its nucleotide sequence, a cDNA sequence encoding the novel rat G protein-coupled receptor protein consisting of the amino acid sequence represented by SEQ ID NO: 10 was obtained (SEQ ID NO: 11). The novel protein comprising the amino acid sequence (SEQ ID NO: 10) derived from the cDNA was designated rat FPRL1. The transformant harboring this plasmid was designated *Escherichia coli* JM109/pUC119-rFPRL1.

Reference Example 3

Preparation of a Plasmid Harboring cDNA Encoding Rat Spleen-Derived FPRL1

The expression vector obtained in Reference Example 2 was cleaved with restriction enzymes Sal I and Nhe I to cut off the inserted fragment which was then inserted into plasmid vector pUC18. As a result of analysis for its nucleotide sequence, it could be confirmed that this sequence, similar to the cDNA sequence in Reference Example 2, is a cDNA sequence (SEQ ID NO: 11) encoding the novel rat G protein-coupled receptor protein consisting of the amino acid sequence represented by SEQ ID NO: 10. A transformant harboring this plasmid was designated *Escherichia coli* JM109/pUC18-rFPRL1.

Example 1

Inhibition, by Humanin, of the Amount of Intracellular cAMP Increased by Addition of Forskolin in CHO Cells Expressing FPRL1-GFP CHO cells expressing FPRL1-GFP were washed with an assay medium (HBSS (GibcoBRL) supplemented with 0.1% bovine serum albumin and 0.2 mM IBMX) and then cultured at 37° C. in 5% $CO_2$ for 30 minutes. Humanin (Peptide Research Laboratory, Co.) or related substances diluted at each concentration with the assay buffer were added thereto, and then forskolin was added at a final concentration of 1 µM. The cells were cultured at 37° C. in 5% $CO_2$ for 30 minutes. The culture supernatant was discarded, and the amount of cAMP in the cells was measured with a plate reader (ARVO sx multi-label counter, manufactured by Wallac) according to a protocol of a cAMP screen kit (Applied Biosystems).

As humanin and relates substances, the following compounds were used.
(1) fMLF.
(2) Humanin: human humanin (1-24) consisting of the amino acid sequence represented by SEQ ID NO: 3.

(3) [Gly$^{14}$] humanin: [Gly$^{14}$]-human humanin (1-24) consisting of the amino acid sequence represented by SEQ ID NO: 4.

Figure 2:
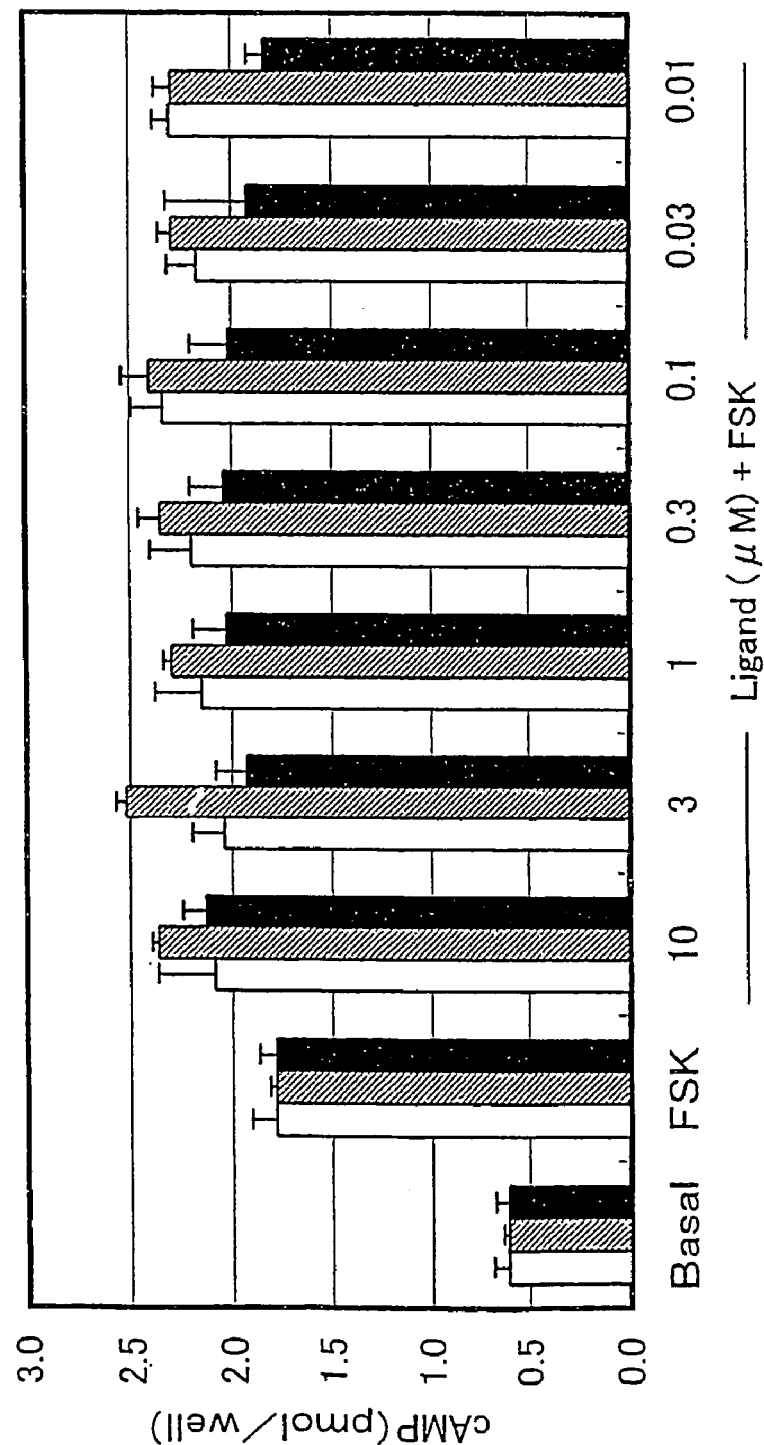
FIG. 2 shows the dose dependence of the activity (in terms of the amount of intracellular cAMP) of a ligand specific to CHO cells (mock) not expressing FPRL1-GFP receptor by measuring an amount of intracellular cAMP. The amount of intracellular cAMP is compared after the cells were incubated in the state (Basal) not stimulated with forskolin or in the presence of 1 μM forskolin and fMLF, humanin or [Gly$^{14}$] humanin at a predetermined concentration shown in the graph. The white column shows the case where fMLF was added. The shaded column shows the case where human humanin (1-24) consisting of the amino acid sequence represented by SEQ ID NO: 3 was added. The black column shows the case where [Gly$^{14}$]-human humanin (1-24) consisting of the amino acid sequence represented by SEQ ID NO: 4 was added. Basal shows the case where forskolin (FSK) and the ligand were not added. FSK shows the case where forskolin was added. Ligand (μM)+FSK shows the case where each ligand and forskolin were added. The number on the abscissa shows the concentration (μM) of each ligand. cAMP (pmol/well) on the ordinate shows the amount of intracellular cAMP (pmol/well).

The result indicated that the dose-dependent and specific decrease, by humanin, of the amount of intracellular cAMP increased by addition of forskolin was detected specifically in the CHO cells into which the FPRL1-GFP gene had been introduced (FIG. 1), as compared with the CHO cells (mock) into which the vector only had been introduced (FIG. 2).

Example 2

Synthesis of Formylated Humanin

The N-terminus of a protected peptide obtained by the known peptide synthesis described above was formylated according to the method described by J. C. Sheehan and D. D. H. Young in J. Amer. Chem. Soc. 80, 1154 (1958) and then deprotected thereby synthesizing the following compounds:
(1) formyl-Humanin: human humanin (1-24) consisting of the amino acid sequence represented by SEQ ID NO: 6, wherein Met at the N-terminus thereof is formylated.
(2) mt-formyl-Humanin: human humanin (1-21) consisting of the amino acid sequence represented by SEQ ID NO: 6, wherein Met at the N-terminus thereof is formylated.
(3) mt-formyl-rattin: rat humanin (1-21) consisting of the amino acid sequence represented by SEQ ID NO: 9, wherein Met at the N-terminus thereof is formylated.

Example 3

Inhibition, by each Agonist, of the Amount of Intracellular cAMP Increased by Addition of Forskolin in Human FPRL1-Expressing CHO Cells (No. 14), Human FPRL1-Expressing CHO Cells (No. 8), Human FPRL2-Expressing CHO Cells (No. 17), mouse FPRL2-Expressing CHO Cells (No. 15) and Rat FPRL1-Expressing CHO Cells (No. 15), CHO cells expressing each receptor were washed with an assay medium (HBSS (GibcoBRL) supplemented with 0.1% bovine serum albumin and 0.2 mM IBMX) and then cultured at 37° C. in 5% $CO_2$ for 30 minutes. Humanin (Peptide Research Laboratory, Co.) or related substances diluted at each concentration with the assay buffer were added thereto, and then forskolin was added at a final concentration of 1 µM. The cells were cultured at 37° C. in 5% $CO_2$ for 30 minutes. The culture supernatant was discarded, and the amount of cAMP in the cells was measured with a plate reader (ARVO sx multi-label counter, manufactured by Wallac) according to a protocol of a cAMP screen kit (Applied Biosystems). Assuming that the amount of cAMP produced in the cells to which 1 µM forskolin had been added was 100% and the amount of cAMP produced in the cells to which forskolin had not been added was 0%, the amount of cAMP upon addition of each agonist is shown in %. The concentration at which the amount of cAMP produced was inhibited by 50% ($EC_{50}$) was calculated from logit-log plotting. As a result, it was found that human and [Gly$^{14}$]-humanin react not only with hFPRL1 but also strongly with hFPRL2 and also with mFPRL2 and rFPRL1. It was further found that the formylated humanin-related peptides, that is, formyl-Humanin, mt-formyl-Humanin and mt-formyl-rattin react not only strongly with hFPRL1 but also with mFPRL2 and rFPRL1 (FIG. 3).

INDUSTRIAL APPLICABILITY

FPRL1 and FPRL2 of the present invention, a partial peptide thereof or a salt thereof, or DNA encoding FPRL1 and FPRL2 of the present invention or a partial peptide thereof can be used for example as an apotosis inhibitor and as a low toxic and safe pharmaceutical preparation such as a prophylactic/therapeutic agent for diseases involving nerve degeneration, for example, nerve degeneration diseases (for example, Alzheimer's disease), brain function disorders, cancers, immune diseases, infection diseases, alimentary diseases, circulatory diseases, endocrine diseases etc.

By using FPRL1 or FPRL2 of the present invention, a partial peptide thereof or a salt thereof and humanin, compounds altering the binding property between humanin and FPRL1 or FPRL2 of the present invention or a salt thereof can be efficiently screened.

The invention claimed is:

1. A method of screening a compound or its salt that alters the binding property or signal transduction between (1) a G protein-coupled receptor protein comprising the amino acid sequence represented by SEQ ID NO: 1 or a salt thereof and (2) humanin or a salt thereof, which comprises:

comparing the case (i) where the receptor protein or a salt thereof is brought into contact with humanin or a salt thereof and the case (ii) where the receptor protein or a salt thereof is contacted with humanin or a salt thereof and a test compound.

2. The screening method according to claim 1, wherein the humanin is:

(1) a polypeptide comprising the amino acid sequence represented by SEQ ID NO: 3 or a salt thereof, (2) a peptide consisting of consecutive 6 to 20 amino acids in the amino acid sequence represented by SEQ ID NO: 3 or a salt thereof, or (3) a polypeptide comprising the amino acid sequence represented by SEQ ID NO: 7 or a salt thereof.

3. The screening method according to claim 1, wherein the humanin is:

(1) a polypeptide or its salt consisting of a) the amino acid sequence represented by SEQ ID NO: 3, b) an amino acid sequence represented by SEQ ID NO: 3 wherein 1 to 10 amino acids are deleted, c) an amino acid sequence represented by SEQ ID NO: 3 to which 1 to 10 amino acids are added, d) an amino acid sequence represented by SEQ ID NO: 3 wherein 1 to 5 amino acids are substituted by other amino acids, or e) an amino acid sequence consisting of the above amino acid sequence with a combination of deletion, addition and substitution mentioned above, (2) a polypeptide or its salt consisting of a) the amino acid sequence represented by SEQ ID NO: 4, b) an amino acid sequence represented by SEQ ID NO: 4 wherein 1 to 10 amino acids are deleted, c) an amino acid sequence represented by SEQ ID NO: 4 to which 1 to 10 amino acids are added, d) an amino acid sequence represented by SEQ ID NO: 4 wherein 1 to 5 amino acids are substituted by other amino acids, or e) an amino acid sequence consisting of the above amino acid sequence with a combination of deletion, addition and substitution mentioned above, (3) a polypeptide or its salt consisting of a) the amino acid sequence represented by SEQ ID NO: 8, b) an amino acid sequence represented by SEQ ID NO: 8 wherein 1 to 10 amino acids are deleted, c) an amino acid sequence represented by SEQ ID NO: 8 to which 1 to 10 amino acids are added, d) an amino acid sequence represented by SEQ ID NO: 8 wherein 1 to 5 amino acids are substituted by other amino acids, or e) an amino acid sequence consisting of the above amino acid sequence with a combination of deletion, addition and substitution mentioned above, (4) a peptide wherein the number of amino acids is 6 to 20, or its salt, consisting of a) an amino acid sequence in positions 19 to 24, positions 5 to 24, positions 1 to 20, positions 5 to 20 or positions 5 to 21 in the amino acid sequence represented by SEQ ID NO: 3, SEQ ID NO: 4 or SEQ ID NO: 8, b) an amino acid sequence comprising the above amino acid sequence wherein 1 to 6 amino acids are deleted, c) an amino acid sequence comprising the above amino acid sequence wherein 1 to 6 amino acids are added, d) an amino acid sequence comprising the above amino acid sequence wherein 1 to 6 amino acids are substituted by other amino acids, and e) an amino acid sequence comprising the above amino acid sequence with a combination of deletion, addition and substitution mentioned above, provided that the peptide does not include a peptide consisting of an amino acid sequence in positions 19 to 24, positions 5 to 24, positions 1 to 20, positions 5 to 20 or positions 5 to 21 in the amino acid sequence represented by SEQ ID NO: 5, or (5) a polypeptide or its salt consisting of a) the amino acid sequence represented by SEQ ID NO: 7, b) an amino acid sequence represented by SEQ ID NO: 7 wherein 1 to 10 amino acids are deleted, c) an amino acid sequence represented by SEQ ID NO: 7 to which 1 to 10 amino acids are added, d) an amino acid sequence represented by SEQ ID NO: 7 wherein 1 to 10 amino acids are substituted by other amino acids, or e) an amino acid sequence consisting of the above amino acid sequence with a combination of deletion, addition and substitution mentioned above.

4. The screening method according to claim 1, wherein the humanin is:
(1) a polypeptide consisting of the amino acid sequence represented by SEQ ID NO: 3 or a salt thereof,
(2) a polypeptide consisting of the amino acid sequence represented by SEQ ID NO: 4 or a salt thereof,
(3) a polypeptide consisting of the amino acid sequence represented by SEQ ID NO: 6 or a salt thereof,
(4) a polypeptide consisting of the amino acid sequence represented by SEQ ID NO: 7 or a salt thereof,
(5) a polypeptide consisting of the amino acid sequence represented by SEQ ID NO: 8 or a salt thereof,
(6) a polypeptide consisting of the amino acid sequence represented by SEQ ID NO: 9 or a salt thereof, or
(7) a peptide or its salt consisting of a) an amino acid sequence in positions 19 to 24, positions 5 to 24, positions 1 to 20, positions 5 to 20 or positions 5 to 21 in the amino acid sequence represented by SEQ ID NO: 3, SEQ ID NO: 4 or SEQ ID NO: 8.

5. The screening method according to claim 1, wherein the amino group of an N-terminus methionine residue of humanin is formylated.

6. The screening method according to claim 1, wherein the humanin is a polypeptide, or its salt, consisting of the amino acid sequence represented by SEQ ID NO: 3, SEQ ID NO: 4, SEQ ID NO: 6, SEQ ID NO: 7, SEQ ID NO: 8 or SEQ ID NO: 9, wherein the amino group of an N-terminal methionine residue thereof is formylated.

7. The screening method according to claim 1, which comprises measuring and comparing the amount of labeled humanin or a salt thereof bound to the receptor protein or a salt thereof between the case (i) where labeled humanin or a salt thereof is brought into contact with the receptor protein or a salt thereof and the case (ii) where labeled humanin or a salt thereof and a test sample are brought into contact with the receptor protein or a salt thereof.

8. The screening method according to claim 1, which comprises measuring and comparing the amount of labeled humanin or a salt thereof bound to cells containing the receptor protein between the case (i) where labeled humanin or a salt thereof is brought into contact with the cells and the case (ii) where labeled humanin or a salt thereof and a test compound are brought into contact with the cells.

9. The screening method according to claim 1, which comprises measuring and comparing the amount of labeled humanin or a salt thereof bound to a cell membrane fraction containing the receptor protein between the case (i) where labeled humanin or a salt thereof is brought into contact with the cell membrane fraction and the case (ii) where labeled humanin or a salt thereof and a test compound are brought into contact with the cell membrane fraction.

10. The screening method according to claim 1, which comprises measuring and comparing the amount of labeled humanin or a salt thereof bound to the receptor protein between the case (i) where labeled humanin or a salt thereof is brought into contact with the receptor protein expressed on a cell membrane of a cultured transformant transformed with a recombinant vector comprising DNA comprising DNA encoding the receptor protein and the case (ii) labeled humanin or a salt thereof and a test compound are brought into contact with the receptor protein expressed on a cell membrane of the transformant.

11. The screening method according to claim 1, which comprises measuring and comparing a cell-stimulating activity mediated by the receptor protein between the case (1) where a compound or its salt that activates the receptor protein is brought into contact with cells containing the receptor protein and the case (2) where a compound or its salt that activates the receptor protein, and a test compound, are brought into contact with cells containing the receptor protein.

12. The screening method according to claim 1, which comprises measuring and comparing a cell-stimulating activity mediated by the receptor protein between the case where a compound or its salt that activates the receptor protein is brought into contact with the receptor protein expressed on a cell membrane of a cultured transformant transformed with a recombinant vector comprising DNA comprising DNA encoding the receptor protein and the case where a compound or its salt that activates the receptor protein, and a test compound, are brought into contact with the receptor protein expressed on a cell membrane of the transformant.

13. A kit for screening a compound or its salt that alters the binding property or signal transduction between (1) a G protein-coupled receptor protein comprising the amino acid sequence represented by SEQ ID NO: 1, or a salt thereof and (2) humanin or a salt thereof, which comprises the receptor protein, or a salt thereof and humanin or a salt thereof.

14. A method of screening an agonist or antagonist to a G protein-coupled receptor protein comprising the amino acid sequence represented by SEQ ID NO: 1, or to a salt thereof, which comprises:
measuring an inhibitory activity on intracellular cAMP formation upon bringing a test compound into contact with cells containing the receptor protein.

* * * * *